(12) United States Patent
Ogita et al.

(10) Patent No.: US 7,960,566 B2
(45) Date of Patent: Jun. 14, 2011

(54) ANTHRACENE DERIVATIVE AND LIGHT-EMITTING DEVICES, ELECTRONIC DEVICES, AND LIGHTING DEVICE USING THE ANTHRACENE DERIVATIVE

(75) Inventors: Kaori Ogita, Kanagawa (JP); Sachiko Kawakami, Kanagawa (JP); Tsunenori Suzuki, Kanagawa (JP); Satoshi Seo, Kanagawa (JP)

(73) Assignee: Semiconductor Energy Laboratory Co., Ltd., Kanagawa-Ken (JP)

( * ) Notice: Subject to any disclaimer, the term of this patent is extended or adjusted under 35 U.S.C. 154(b) by 0 days.

(21) Appl. No.: 12/576,016

(22) Filed: Oct. 8, 2009

(65) Prior Publication Data
US 2010/0099890 A1   Apr. 22, 2010

(30) Foreign Application Priority Data

Oct. 17, 2008   (JP) ................................ 2008-269097
Feb. 12, 2009   (JP) ................................ 2009-030140

(51) Int. Cl.
*C07D 209/86* (2006.01)
*C07D 209/82* (2006.01)
*B32B 19/02* (2006.01)

(52) U.S. Cl. .................... 548/445; 548/440; 428/690
(58) Field of Classification Search .................. None
See application file for complete search history.

(56) References Cited

U.S. PATENT DOCUMENTS

| 2005/0260442 A1 | 11/2005 | Yu et al. |
| 2007/0075632 A1* | 4/2007 | Kawakami et al. ............ 313/504 |
| 2007/0152572 A1 | 7/2007 | Kawakami et al. |
| 2007/0267969 A1 | 11/2007 | Nakashima et al. |
| 2008/0268284 A1 | 10/2008 | Kawakami et al. |
| 2010/0096981 A1* | 4/2010 | Seo et al. ...................... 313/504 |

FOREIGN PATENT DOCUMENTS

| JP | 09-310066 | 12/1997 |
| WO | WO 2006/104221 A1 | 10/2006 |
| WO | WO 2007/013537 A1 | 2/2007 |

OTHER PUBLICATIONS

Shi et al., "Anthracene Derivatives for Stable Blue-Emitting Organic Electroluminescence Devices", Appl. Phys. Lett. (Applied Physics Letters), Apr. 29, 2002, vol. 80, No. 17, pp. 3201-3203.

* cited by examiner

*Primary Examiner* — Kamal A Saeed
*Assistant Examiner* — Nyeemah Grazier
(74) *Attorney, Agent, or Firm* — Nixon Peabody LLP; Jeffrey L. Costellia

(57) ABSTRACT

An anthracene derivative is disclosed, and a light-emitting element, a light-emitting device, an electronic device, and a lighting device using the anthracene derivatives are demonstrated. The structure of the anthracene derivative is described in detail in the specification. The use of the anthracene derivative enables the production of a blue emissive light-emitting element having high emission efficiency, excellent purity of emission color, and a long lifetime, which contributes to the production of a high-performance light-emitting device, electronic device, and lighting device.

20 Claims, 30 Drawing Sheets

ANTHRACENE DERIVATIVE AND LIGHT-EMITTING DEVICES, ELECTRONIC DEVICES, AND LIGHTING DEVICE USING THE ANTHRACENE DERIVATIVE

BACKGROUND OF THE INVENTION

1. Field of the Invention

The present invention relates to anthracene derivatives, and light-emitting devices, electronic devices, and lighting devices in which the anthracene derivatives are used.

2. Description of the Related Art

A light-emitting element utilizing a light-emitting organic compound has a structure in which a layer containing the organic compound is interposed between a pair of electrodes. Such a light-emitting element is characterized in that a thin and lightweight light-emitting element can be fabricated, light is emitted by applying direct current, and response is faster compared to liquid crystal displays, and the like. Moreover, the light-emitting devices in which such light-emitting elements are arranged in matrix form, i.e., passive matrix type light-emitting devices and active matrix type light-emitting devices, are superior to conventional liquid crystal displays in terms of wide viewing angle and excellent visibility. From these reasons, the light-emitting elements are expected to be applied to next-generation flat panel displays. In some cases, these light-emitting elements are referred to as electroluminescent elements or EL elements.

In the light-emitting elements, electrons are injected from a cathode into a layer containing an organic compound interposed between a pair of electrodes, and at the same time, holes are injected from an anode into the layer containing the organic compound, whereby a light-emitting element is driven. The electrons injected from the cathode and the holes injected from the anode are recombined with each other in the layer containing the organic compound to form molecular excitons. The molecular excitons release energy in relaxing to a ground state. When the energy is released as visible light, light emission can be observed. Excited states of organic compounds include a singlet excited state and a triplet excited state, and light can be emitted from both of the excited states.

An emission wavelength of the light-emitting element is determined by the energy gap between the ground state and the excited state formed by the recombination, i.e., a band gap. Therefore, a structure of a molecule that serves for emitting light is selected or modified as appropriate, whereby desired emission color of light can be obtained. A full color light-emitting device can be manufactured by using the light-emitting elements capable of emitting light of red, blue, and green colors that are three primary colors of light.

In order to manufacture a high performance full-color light-emitting device, red, green, and blue emissive light-emitting elements having a long lifetime, high emission efficiency, and excellent color purity are required. As a result of recent development of materials, as for the red and green emissive light-emitting elements, excellent characteristics have been attainable. However, as for a blue emissive light-emitting element, sufficient characteristics have not been obtained. For example, in Nonpatent Document 1 (J. Shi et al., Applied Physics Letters, 2002, Vol. 80, No. 17, pp. 3201-3203), a blue emissive light-emitting element with relatively high reliability is reported. However, sufficient emission efficiency and color purity are not realized. [Non-Patent Document 1]

SUMMARY OF THE INVENTION

In view of the foregoing problems, an object of an embodiment of the present invention is to provide novel anthracene derivatives.

It is another object to provide a light-emitting element having a long lifetime. It is still another object to provide a light-emitting element having high emission efficiency. Further, another object is to provide a light-emitting element that emits blue light with high color purity.

Another object of an embodiment of the present invention is to provide a light-emitting device, an electronic device, and a lighting device with reduced power consumption.

As a result of intensive study, the inventors have found that the problems can be solved with an anthracene derivative represented by a general formula (G1) given below. Thus, one embodiment of the present invention is an anthracene derivative represented by the following general formula (G1).

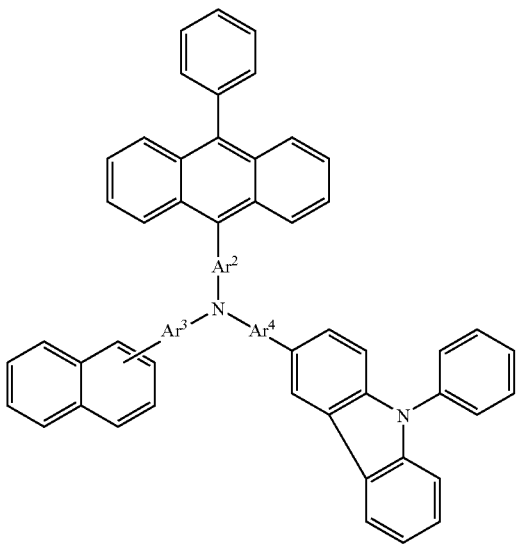

(G1)

In the above general formula (G1), $Ar^2$, $Ar^3$, and $Ar^4$ each independently represent a phenylene group or a biphenyl-4,4'-diyl group.

Further, an embodiment of the present invention is an anthracene derivative represented by a following general formula (G1-1).

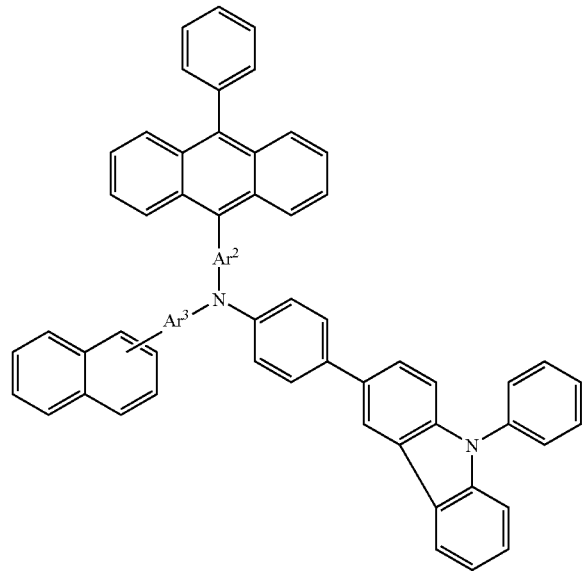

(G1-1)

In the above general formula (G1-1), $Ar^2$ and $Ar^3$ each independently represent a phenylene group or a biphenyl-4,4'-diyl group.

Further, an embodiment of the present invention is an anthracene derivative represented by the following general formula (G1-2).

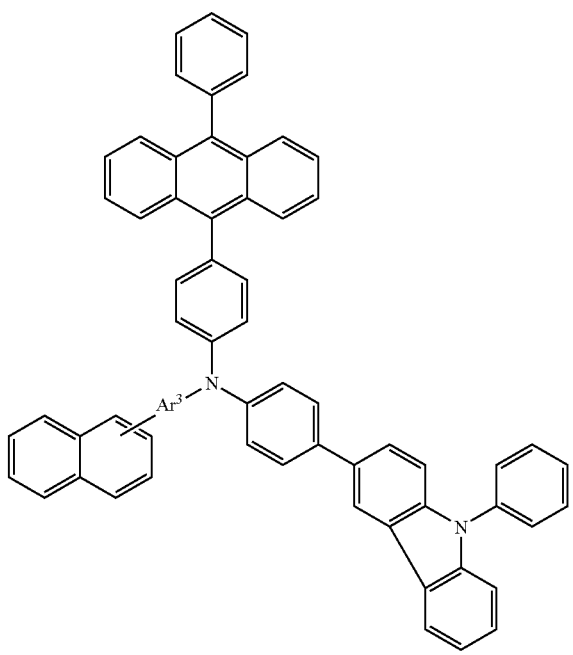

(G1-2)

In the general formula (G1-2), $Ar^3$ represents a phenylene group or a biphenyl-4,4'-diyl group.

Further, an embodiment of the present invention is an anthracene derivative represented by the following structural formula (101).

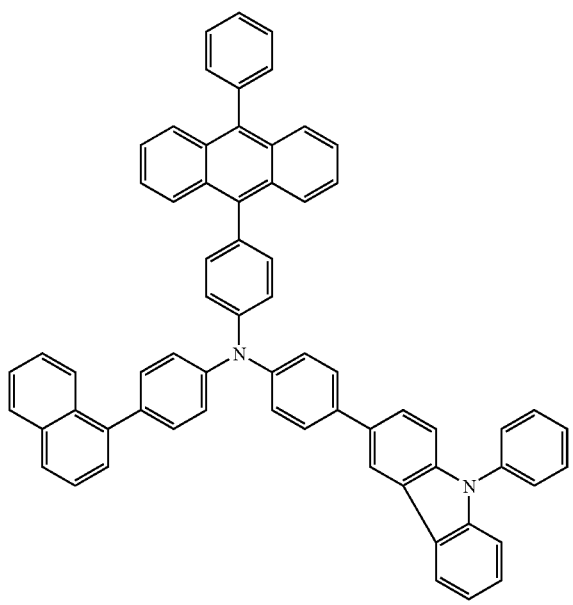

(101)

Furthermore, an embodiment of the present invention is an anthracene derivative represented by the following structural formula (103).

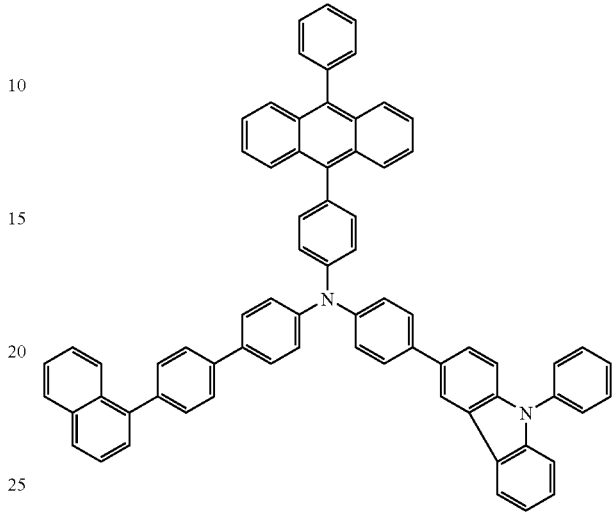

(103)

Another embodiment of the present invention is a light-emitting element including any of the above anthracene derivatives. In other words, an embodiment of the present invention is a light-emitting element including any of the above anthracene derivatives between a pair of electrodes.

Since the above anthracene derivatives have high emission efficiency, it is preferred to use the anthracene derivatives in a light-emitting layer. Thus, one embodiment of the present invention is a light-emitting element that includes a light-emitting layer between a pair of electrodes, where the light-emitting layer contains any of the above-described anthracene derivatives.

The light-emitting element of the present invention obtained in this manner exhibits a long lifetime, and thus, a light-emitting device (e.g., an image display device) in which such a light-emitting element is utilized also shows a long lifetime. Thus, an embodiment of the present invention also includes the light-emitting device and an electronic device each of which uses the light-emitting element according to the present invention.

The light-emitting device of the embodiments of the present invention includes a light-emitting element including any of the above-described anthracene derivatives and a control circuit configured to control light emission from the light-emitting element. Note that the light-emitting device in this specification includes a light-emitting device such as an image display device using a light-emitting element. Further, the category of the light-emitting device includes: a module including a light-emitting element to which a connector such as an anisotropic conductive film, TAB (tape automated bonding) tape, or a TCP (tape carrier package) is added; a module in which the top of a TAB tape or a TCP is provided with a printed wire board; a module in which an IC (integrated circuit) is directly mounted on a light-emitting element by a COG (chip on glass) technique; and the like. Moreover, a light-emitting device used in a lighting device or the like is also included.

Further, an electronic device using the light-emitting element of the embodiments of the invention in a display portion is also included in the scope of the invention. Accordingly, an embodiment of the present invention is an electronic device which includes a display portion provided with the above-described light-emitting element and a control circuit which controls light emission of the light-emitting element.

Furthermore, since the organic compounds used for the synthesis of the anthracene derivatives of the embodiments of the present invention are novel materials, they are also included in the present invention. Therefore, one embodiment of the present invention is an organic compound represented by the following general formula (G2).

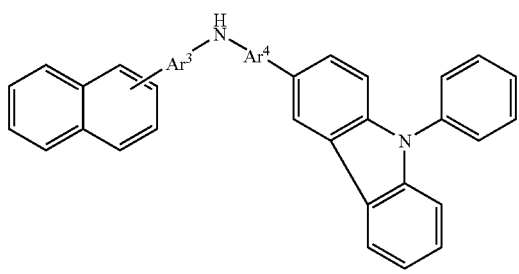

(G2)

In the above general formula (G2), $Ar^3$ and $Ar^4$ each independently represent a phenylene group or a biphenyl-4,4'-diyl group.

Another embodiment of the present invention is an organic compound represented by the following general formula (G2-1).

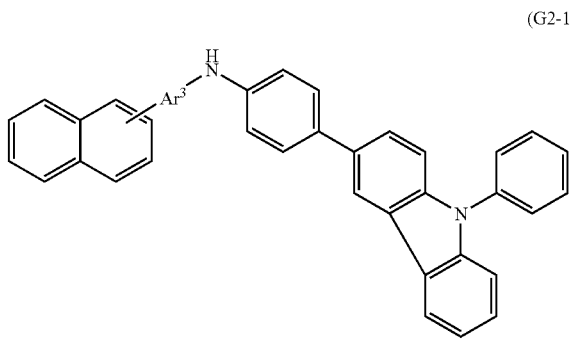

(G2-1)

In the above general formula (G2-1), $Ar^3$ represents a phenylene group or a biphenyl-4,4'-diyl group.

Moreover, one embodiment of the present invention is an organic compound represented by the following structural formula (301).

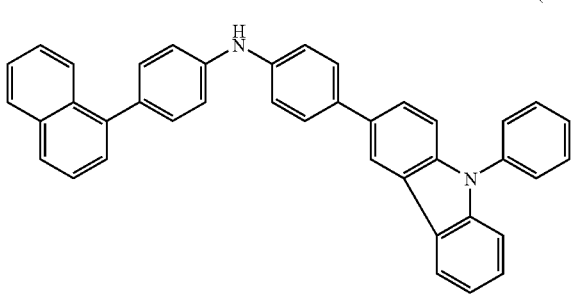

(301)

Additionally, another embodiment of the present invention is an organic compound represented by the following structural formula (302).

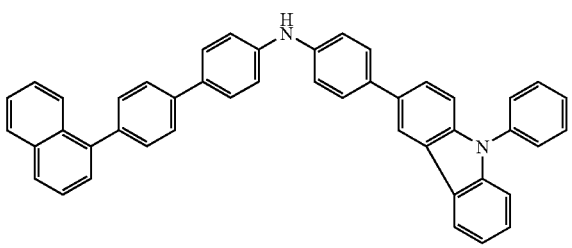

(302)

The anthracene derivatives of the embodiments of the present invention have high emission efficiency. Furthermore, the anthracene derivatives of the embodiments of the present invention can emit blue light with high color purity. Moreover, the anthracene derivatives of the embodiments of the present invention are electrochemically stable and highly resistant to repetitive oxidation and reduction.

Also, by the use of the anthracene derivatives of the embodiments of the present invention, a light-emitting element with high emission efficiency can be obtained. Further, a light-emitting element that emits blue light with high color purity can also be obtained. Moreover, a blue emissive light-emitting element having a long lifetime can be obtained.

Further, the use of the anthracene derivatives of the embodiments of the present invention allows the production of a light-emitting device, an electronic device, and a lighting device with reduced power consumption.

DETAILED DESCRIPTION OF THE INVENTION

Figure 1A:
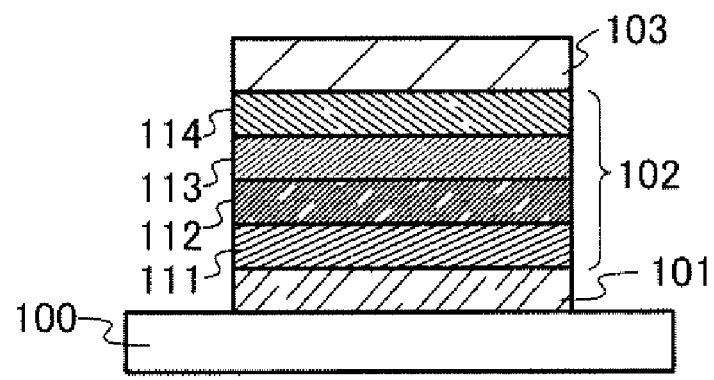
FIGS. 1A and 1B are diagrams explaining a light-emitting element according to an embodiment of the present invention.

Hereinafter, the embodiments of the present invention will be described in detail with reference to the accompanying drawings. However, the present invention is not limited to the following description, and various changes and modifications for the modes and details thereof will be apparent to those skilled in the art unless such changes and modifications depart from the spirit and scope of the invention. Therefore, the present invention is not construed as being limited to the description of the embodiments and examples given below.

Embodiment 1

In the present embodiment, explanation is given for an anthracene derivative of an embodiment of the present invention and for an organic compound used for the synthesis of the anthracene derivative.

The anthracene derivative shown in the present embodiment is represented by the general formula (G1) shown below.

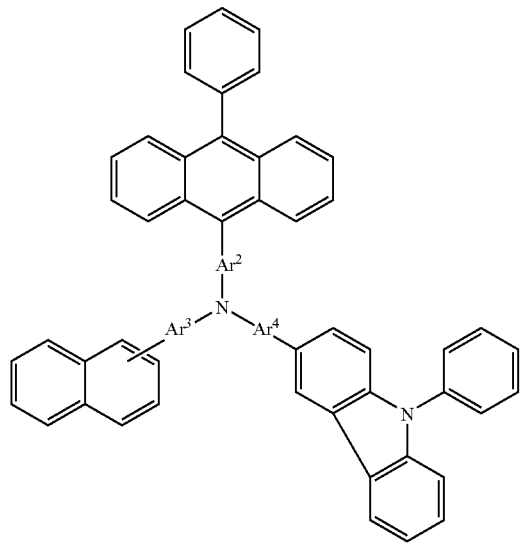

(G1)

In the above-described general formula (G1), $Ar^2$, $Ar^3$, and $Ar^4$ each independently represent a phenylene group or a biphenyl-4,4'-diyl group.

The anthracene derivative shown by the general formula (G1) is characterized by having a naphthyl group at a terminal of an amine skeleton. Specifically, the anthracene derivative is characterized by having the naphthyl group which is directly bonded to $Ar^3$. Introduction of the naphthyl group at the terminal of the amine skeleton allows the anthracene derivative represented by the general formula (G1) to efficiently emit light and exhibit high electrochemical stability.

As the phenylene group and the biphenyl-4,4'-diyl group which are referred to as $Ar^2$, $Ar^3$, or $Ar^4$ in the above-described general formula (G1), the structures represented by the formulae (2-1) to (2-4) are provided as examples. Although an ortho-phenylene group, a meta-phenylene group, and a para-phenylene group are exemplified as the phenylene group, the para-phenylene group is preferred because of the facility in synthesis. Further, the biphenyl-4,4'-diyl group in which two para-phenylene groups are bonded to each other is also preferred since it is readily synthesized.

(2-1)

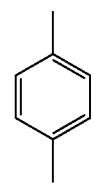

(2-2)

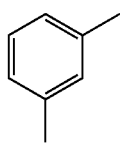

(2-3)

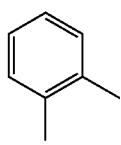

(2-4)

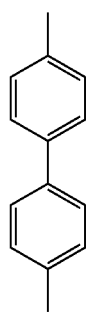

(G1-1)

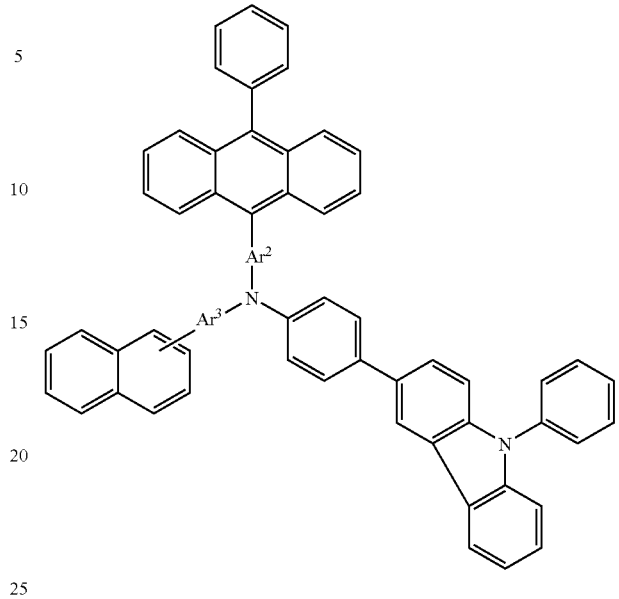

In the above-described general formula (G1-1), $Ar^2$ and $Ar^3$ each independently represent a phenylene group or a biphenyl-4,4'-diyl group.

In the anthracene derivative represented by the general formula (G1-1), $Ar^2$ is preferably a para-phenylene group for ease of synthesis. That is, a preferable anthracene derivative is represented by a general formula (G1-2).

(G1-2)

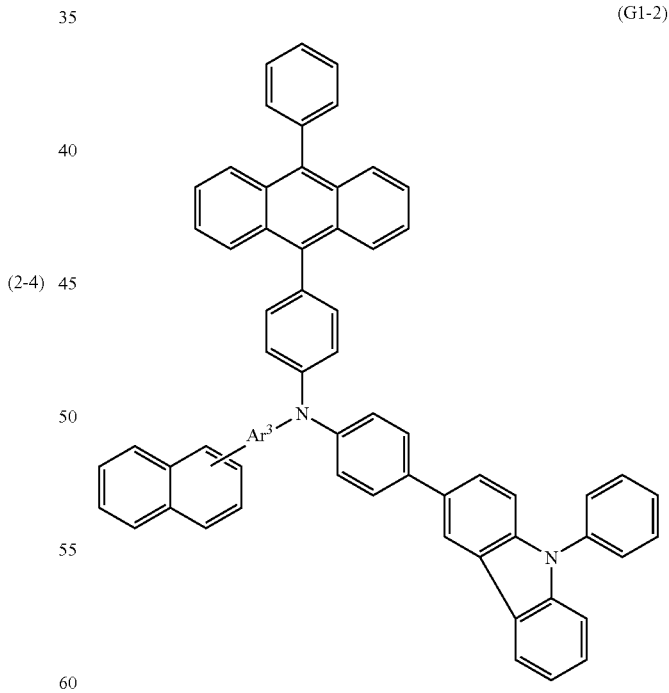

In the above-described general formula (G1-2), $Ar^3$ represents a phenylene group or a biphenyl-4,4'-diyl group.

In the anthracene derivative represented by the general formula (G1), $Ar^4$ is preferably a para-phenylene group for ease of synthesis. That is, a preferable anthracene derivative is represented by the general formula (G1-1).

As the examples of these anthracene derivatives, the anthracene derivatives represented by the structural formulae (101) to (114) and (201) to (214) are exemplified. However, the present invention is not limited thereto.

(101)
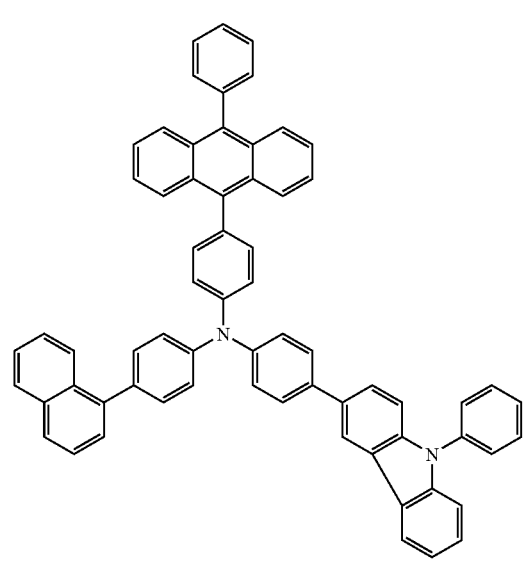
(102)
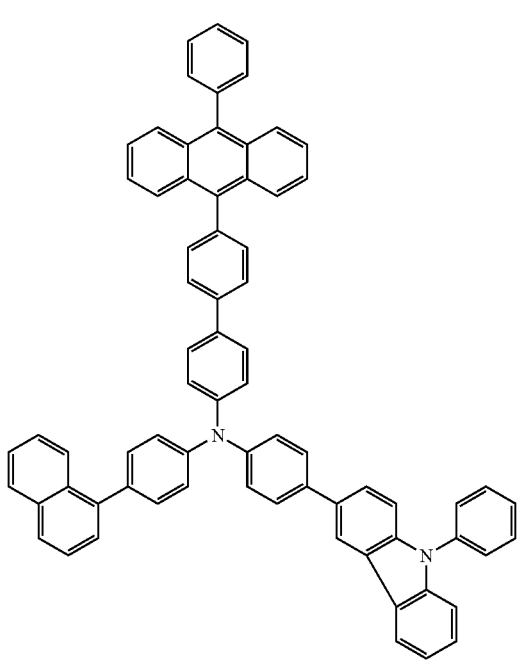
(103)
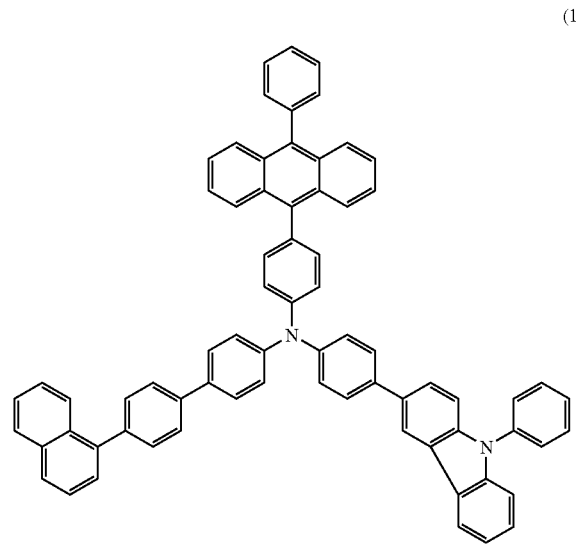
(104)
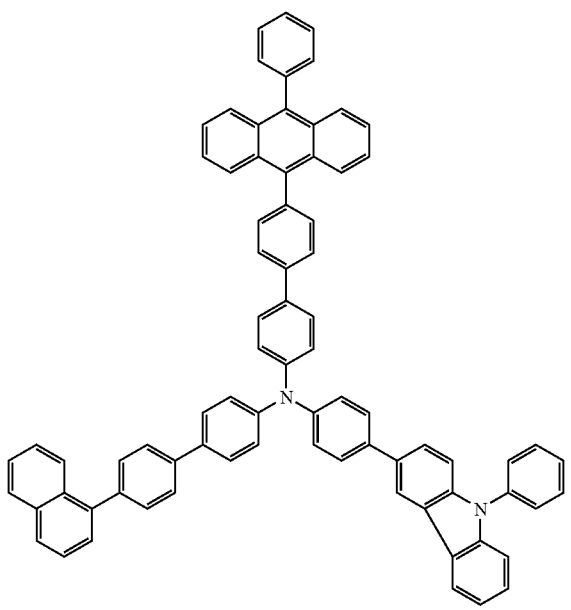

(105)
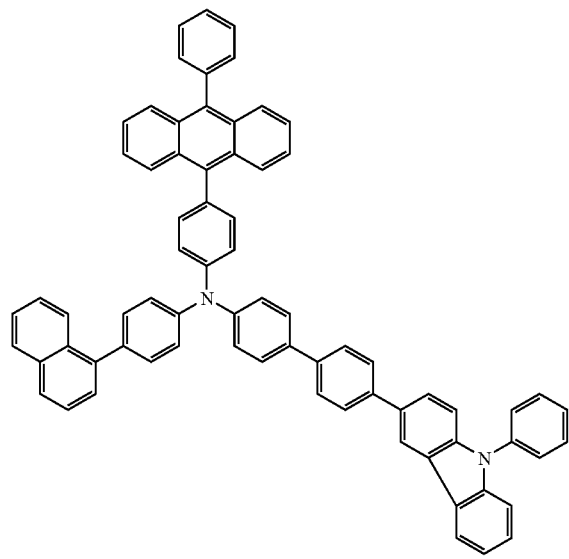
(106)
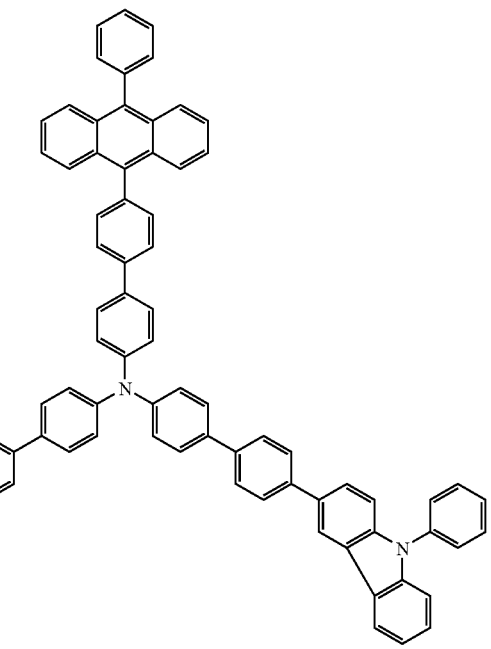
(107)
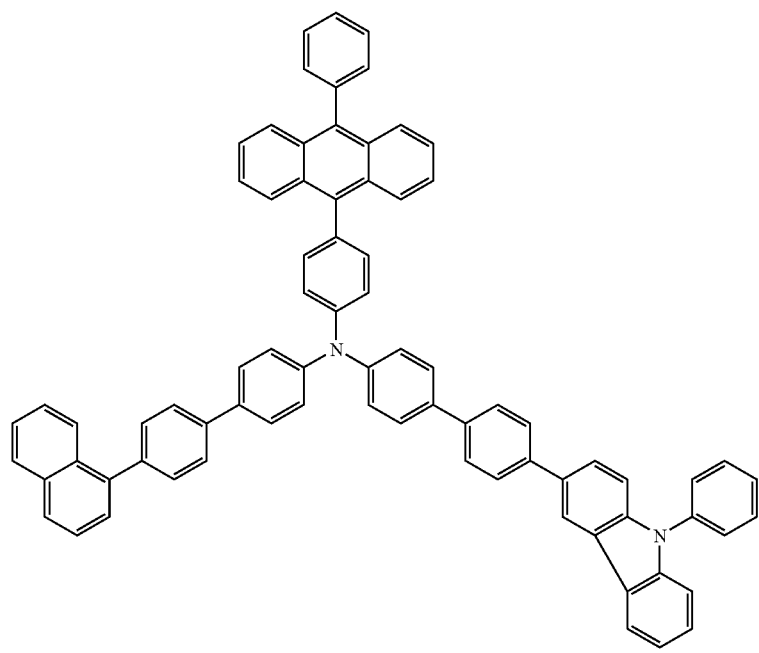

(108)
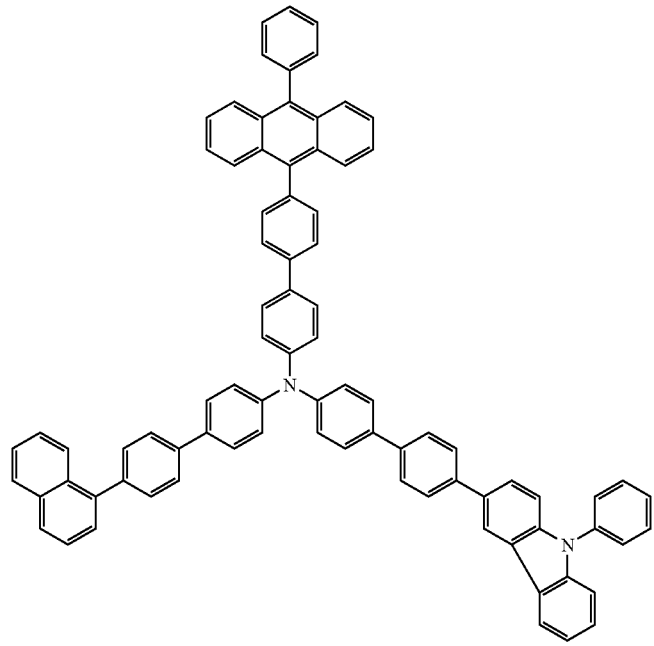
(109)
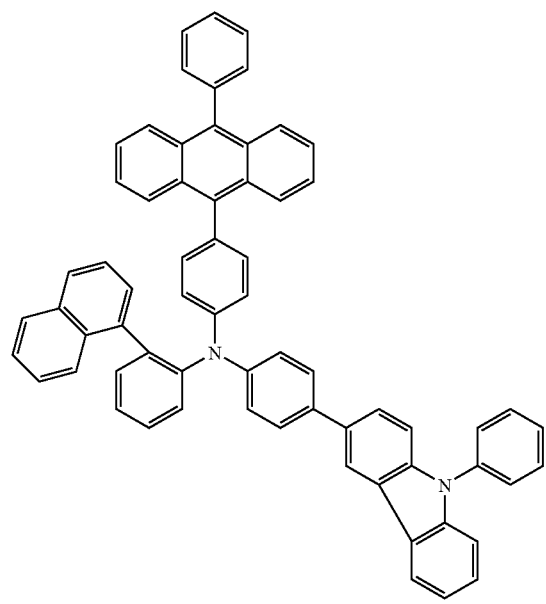
(110)
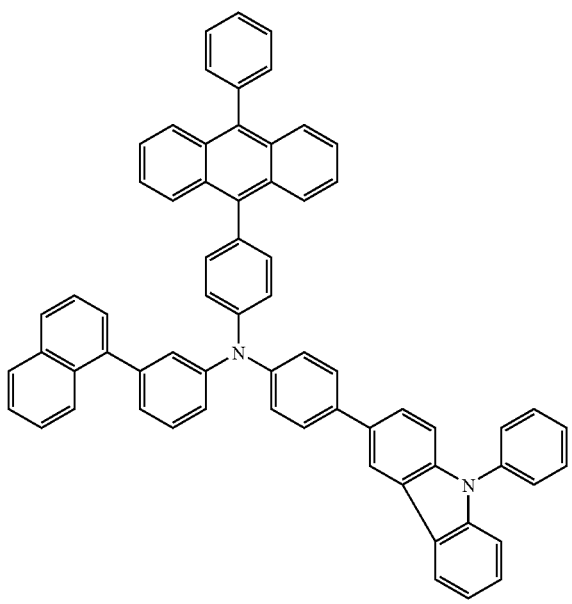

-continued
(111)
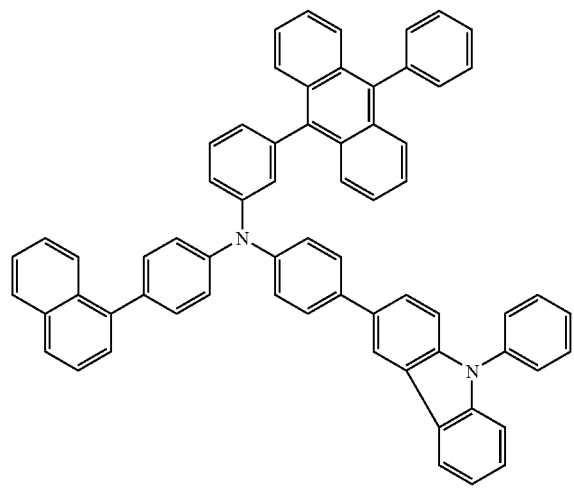
(112)
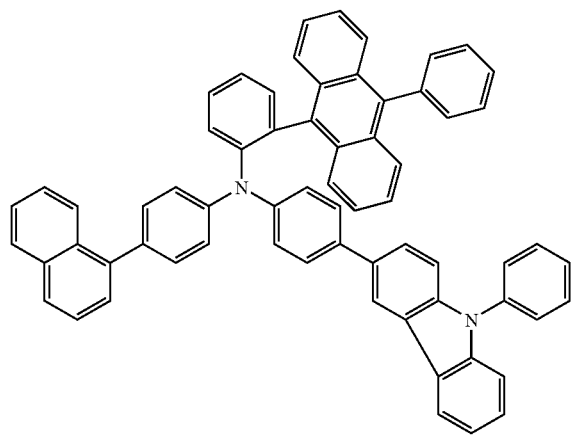
(113)
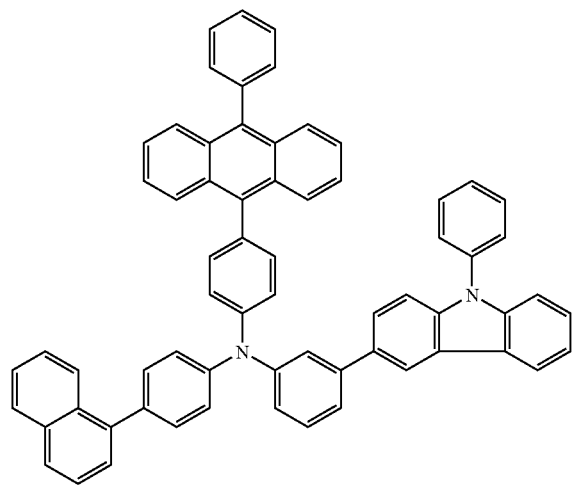
(114)
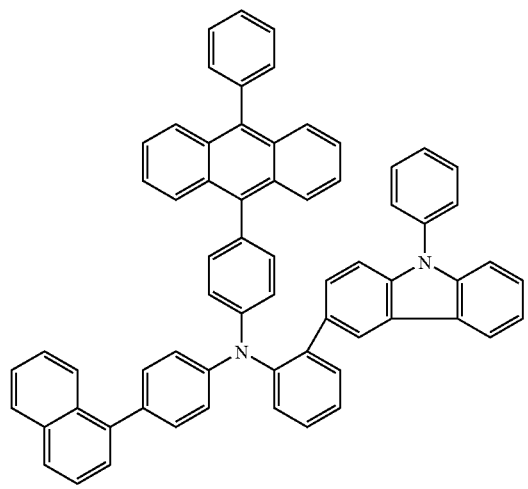
(201)
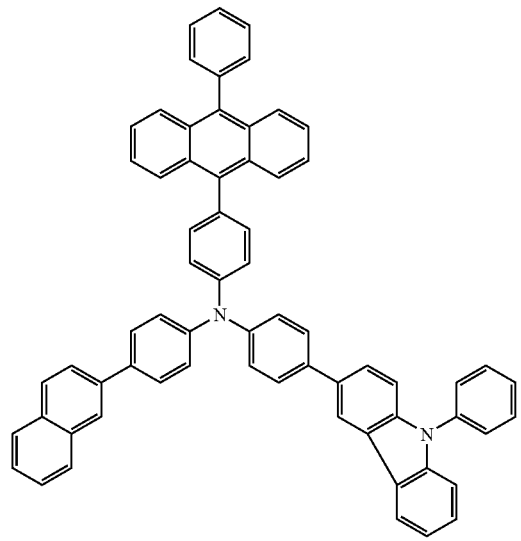
(202)
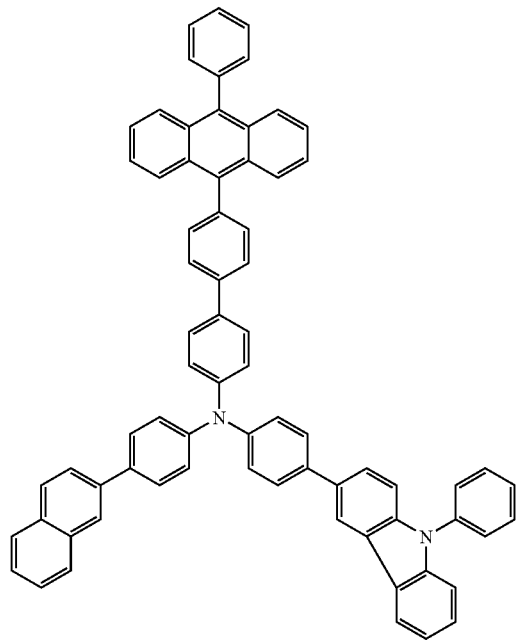

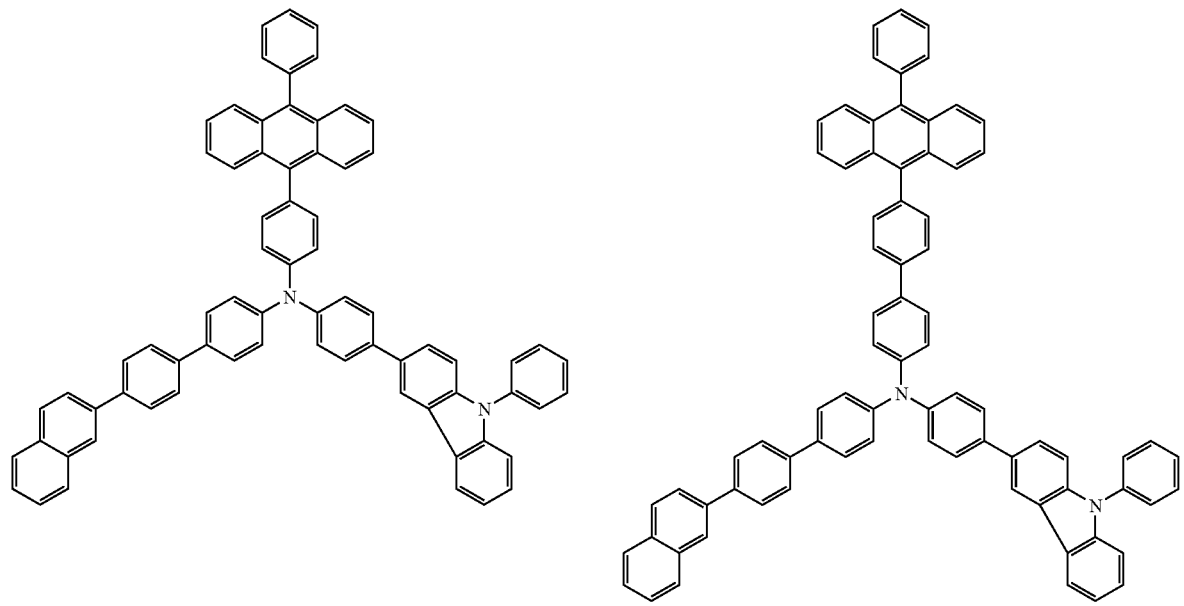
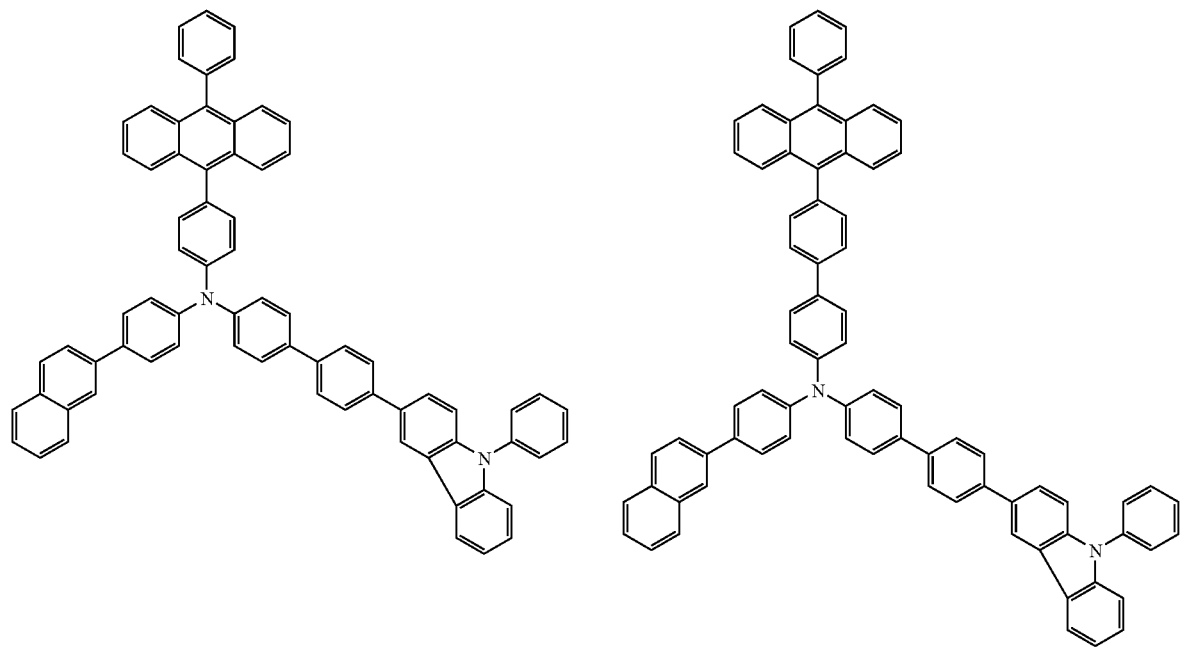

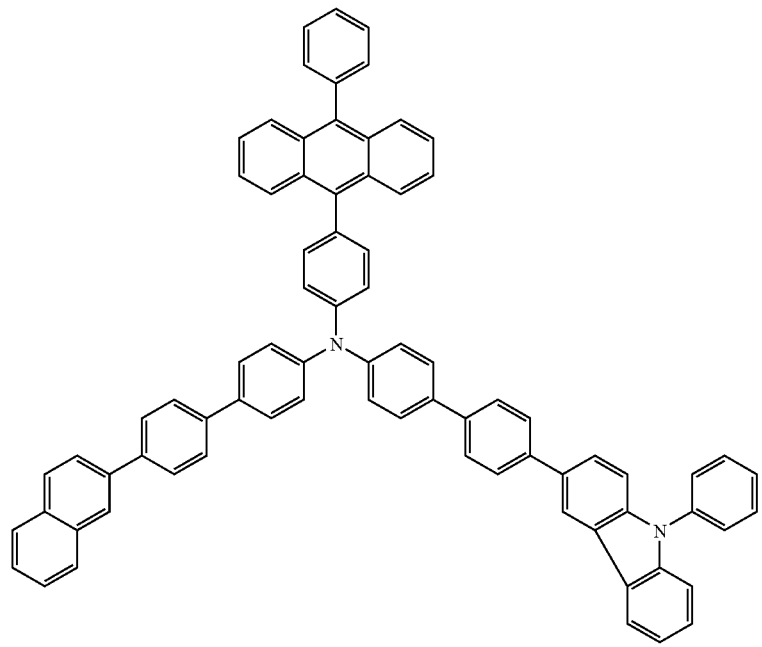
(207)
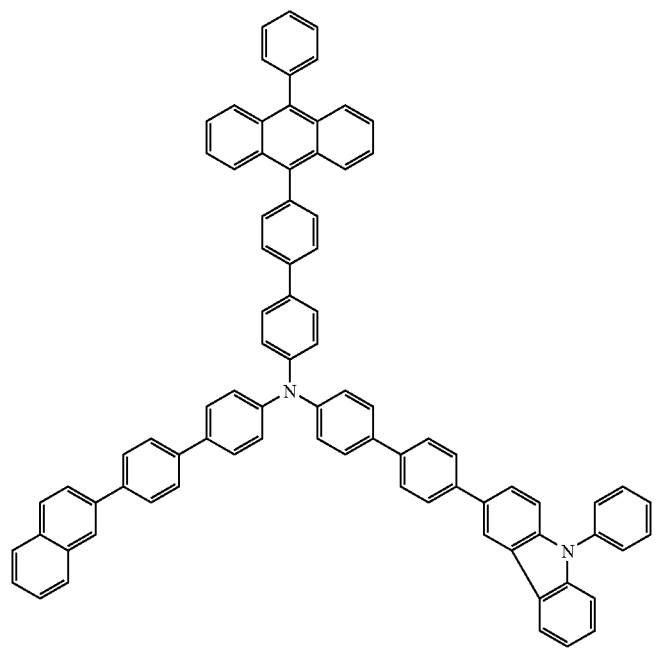
(208)

-continued
(209)
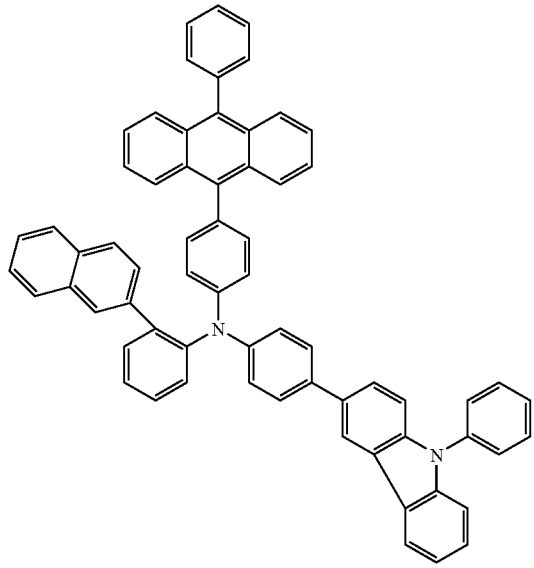
(210)
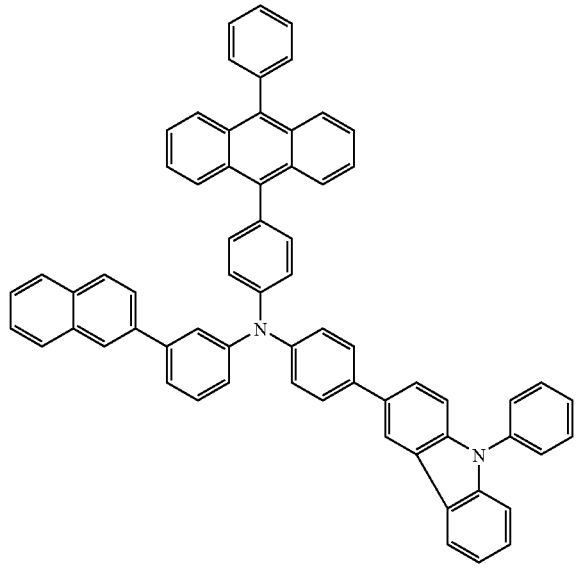
(211)
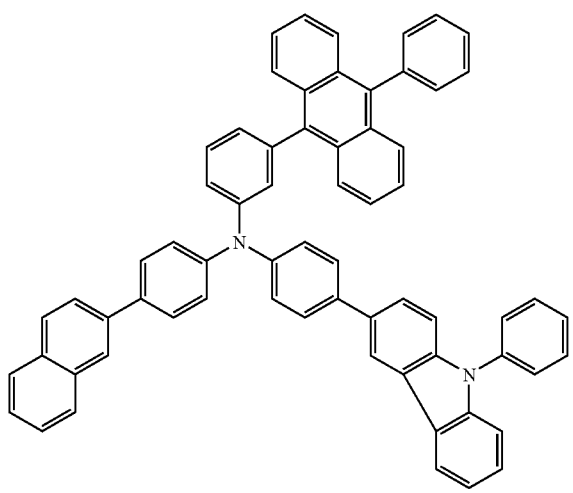
(212)
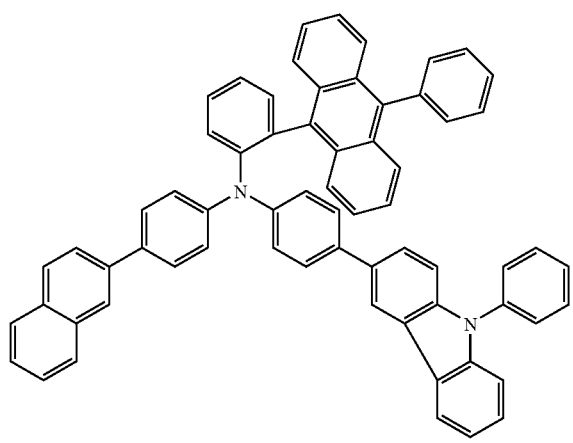
(213)
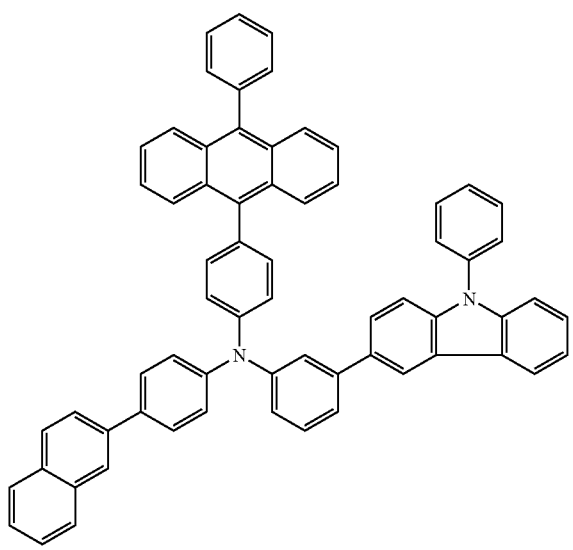
(214)
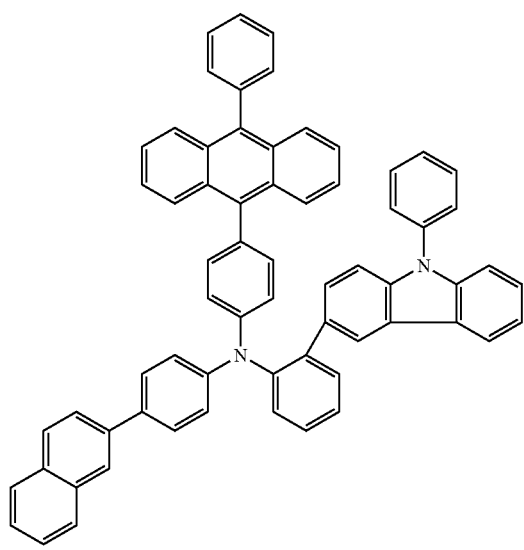

Since the organic compounds used for the synthesis of the anthracene derivatives of the present embodiment are novel materials, these organic compounds are also included in the present invention. Therefore, one embodiment of the present invention is an organic compound represented by the following general formula (G2).

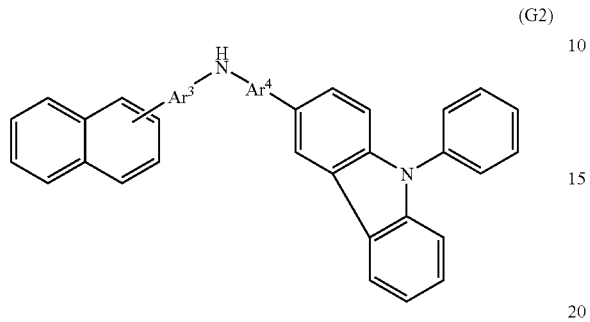
(G2)

In the above-described general formula (G2), $Ar^3$ and $Ar^4$ each independently represent a phenylene group or a biphenyl-4,4'-diyl group.

As the phenylene group and the biphenyl-4,4'-diyl group which are referred to as $Ar^3$ or $Ar^4$ in the above-described general formula (G2), the structures shown by formulae (5-1) to (5-4) are represented as examples. Although an ortho-phenylene group, a meta-phenylene group, and a para-phenylene group are exemplified as the phenylene group, the para-phenylene group is preferred because of the facility in synthesis. Further, the biphenyl-4,4'-diyl group in which two para-phenylene groups are bonded to each other is also preferred since it is readily synthesized.

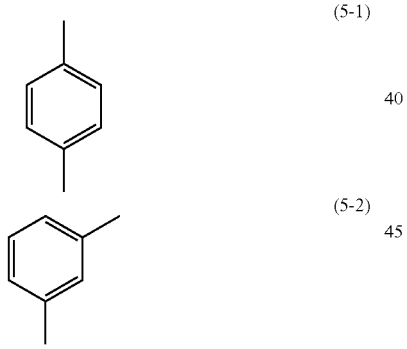
(5-1)
(5-2)

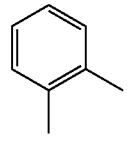
(5-3)

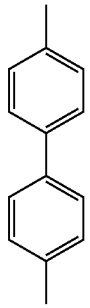
(5-4)

In the organic compound represented by the general formula (G2), $Ar^4$ is preferably a para-phenylene group for ease of synthesis. That is, a preferable organic compound is represented by the general formula (G2-1).

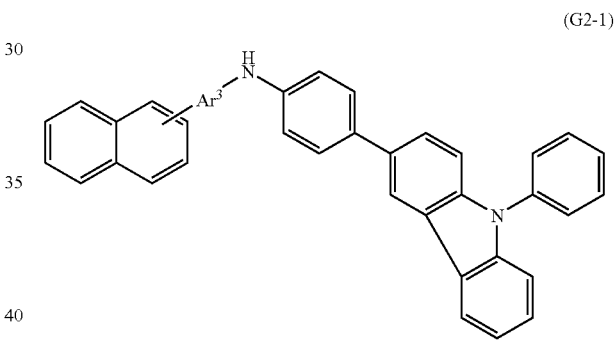
(G2-1)

In the above-described general formula (G2-1), $Ar^3$ represents a phenylene group or a biphenyl-4,4'-diyl group.

As the examples of the organic compounds used in the synthesis of the anthracene derivatives of the present embodiment, the organic compounds represented by the structural formulae (301) to (308) and (401) to (408) are exemplified. However, the present invention is not limited thereto.

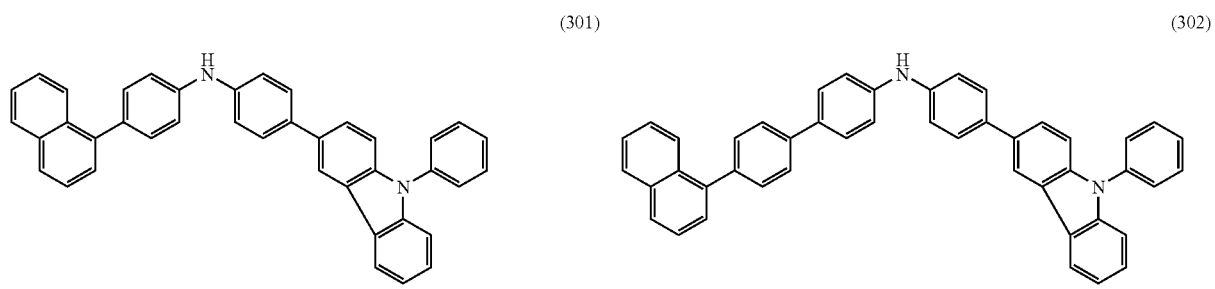
(301) (302)

-continued
(303)
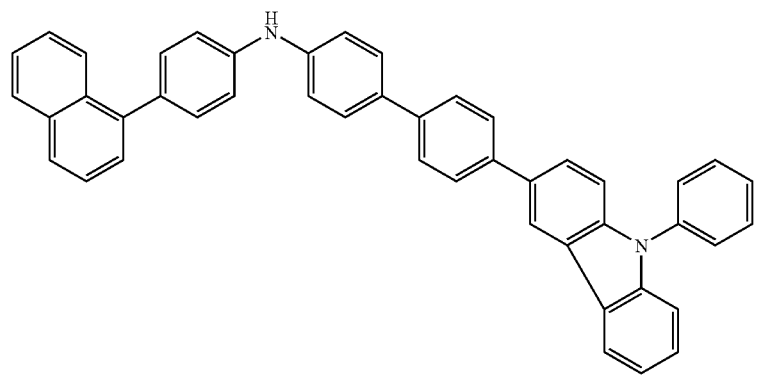
(304)
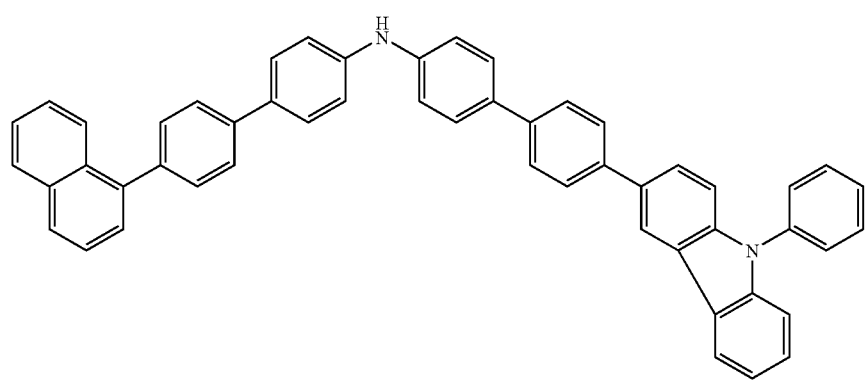
(305)
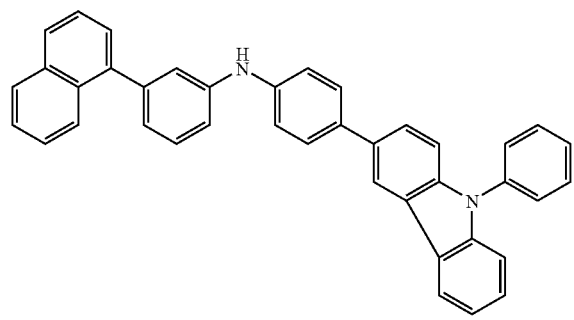
(306)
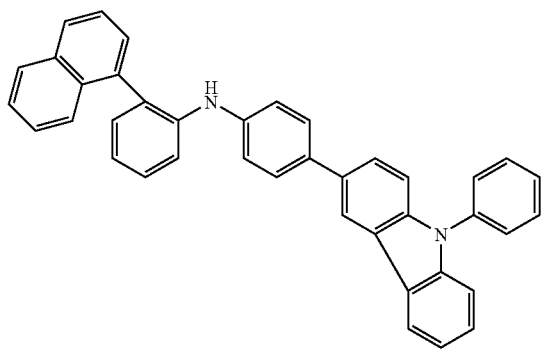
(307)
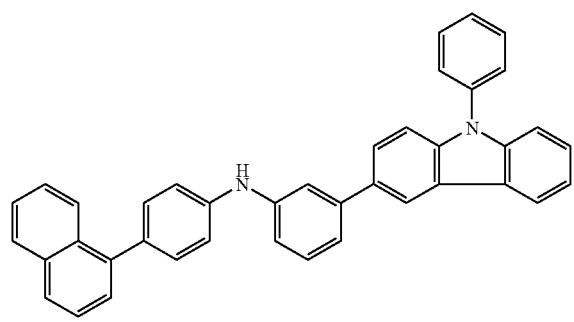
(308)
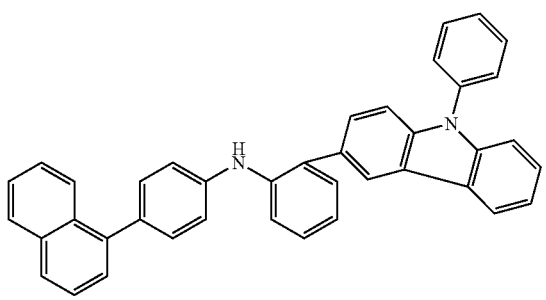

-continued
(401) 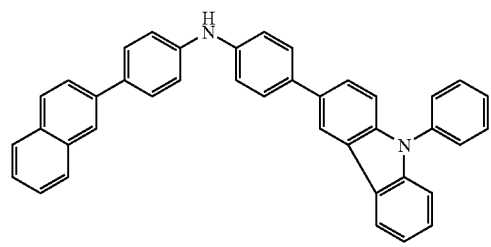
(402) 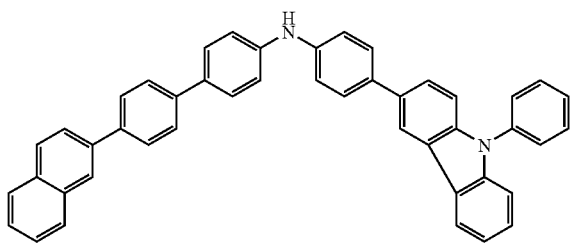
(403) 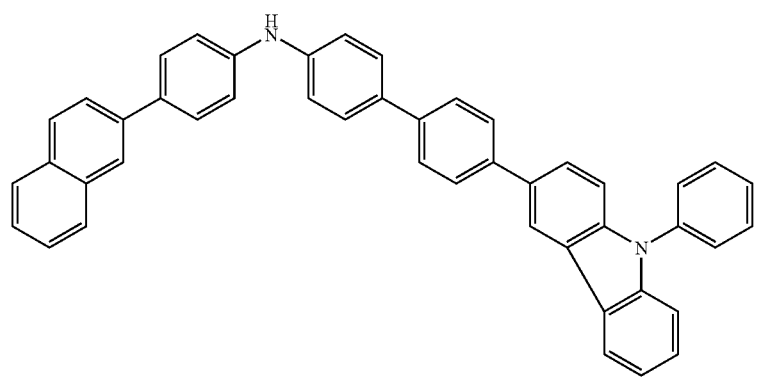
(404) 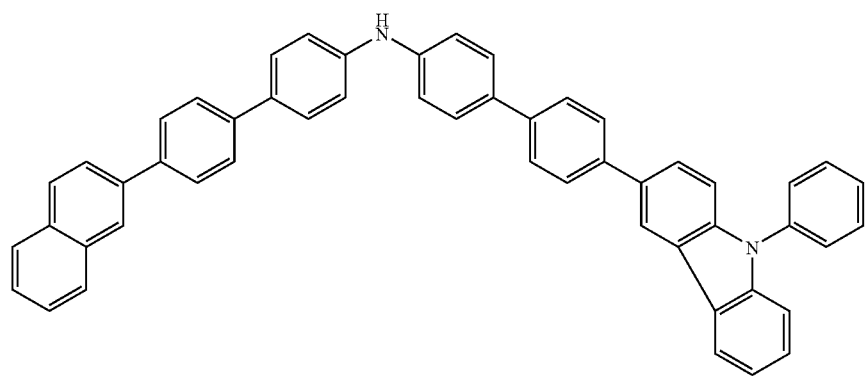
(405) 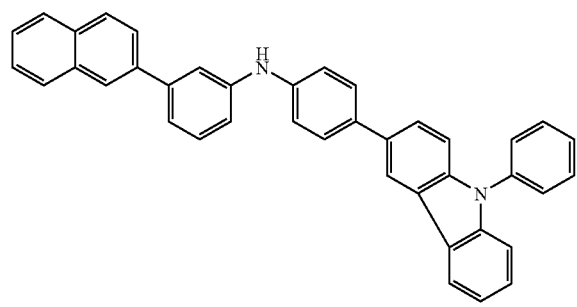
(406) 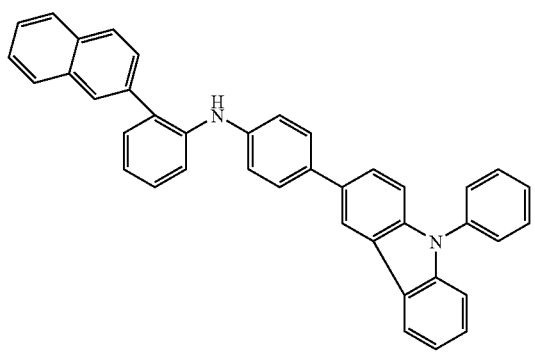

-continued

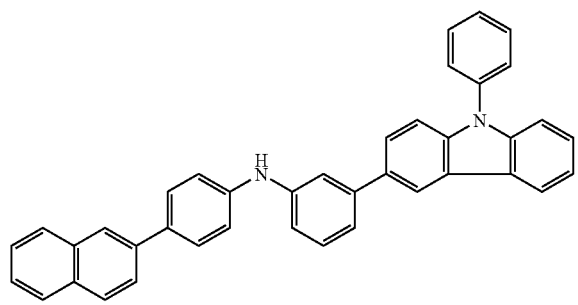
(407)

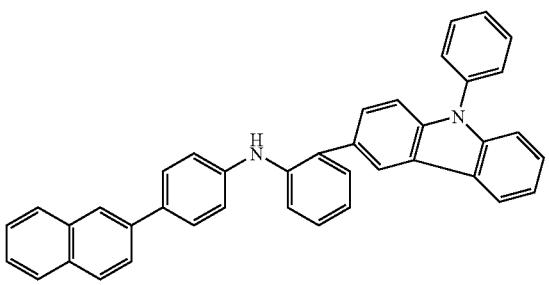
(408)

A variety of synthetic methods can be applied for the synthesis of the anthracene derivatives shown in the present embodiment and the organic compounds used in the synthesis of the anthracene derivatives. For instance, they can be prepared by the synthetic methods shown in the reaction schemes 1 to 7. However, the synthetic methods for the anthracene derivatives shown in the present embodiment are not limited thereto, and it is possible to apply and modify a variety of commonly known reactions.

First, a synthetic method of an anthracene derivative (compound 6) which is a precursor of the anthracene derivative shown in the present embodiment is explained using the reaction schemes 1 to 3.

bases which can be used in the reaction scheme 1 are organic bases such as sodium tert-butoxide, inorganic bases such as potassium carbonate, and the like. Examples of solvents which can be used in the reaction scheme 1 are as follows: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane, and water; and the like. Among them, a mixed solvent of toluene and water or a mixed solvent of toluene, ethanol, and water is more preferable.

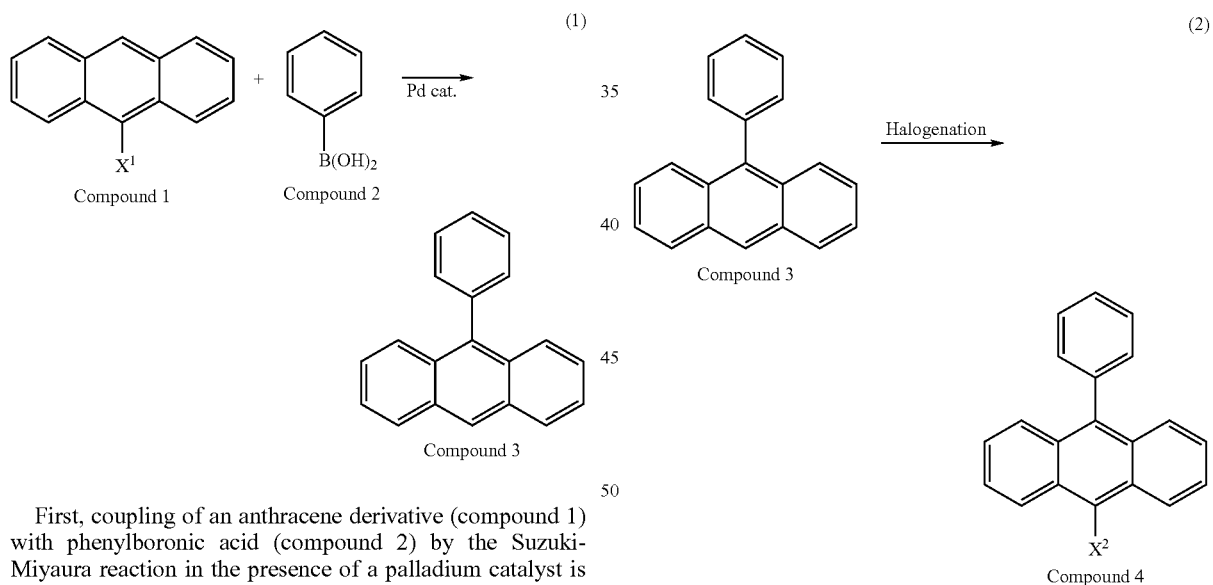

First, coupling of an anthracene derivative (compound 1) with phenylboronic acid (compound 2) by the Suzuki-Miyaura reaction in the presence of a palladium catalyst is carried out to provide 9-phenylanthracene (compound 3) (reaction scheme 1).

In the reaction scheme 1, $X^1$ represents a halogen group or a triflate group, and iodine, bromine, and chlorine are preferred as the halogen group. In this reaction, an organoboron compound which is obtained by protecting the boronic acid of compound 2 using ethylene glycol, pinacol, or the like may be used instead of compound 2.

As the palladium catalyst which can be used in the reaction scheme 1, palladium(II) acetate, tetrakis(triphenylphosphine)palladium(0), and the like are represented. Examples of ligands of the palladium catalysts which can be used in the reaction scheme 1 are tri(o-tolyl)phosphine, triphenylphosphine, tricyclohexylphosphine, and the like. Examples of Next, a halogenated 9-phenylanthracene (compound 4) can be obtained by the halogenation of 9-phenylanthracene (compound 3) obtained by the reaction scheme 1 (reaction scheme 2).

In the reaction scheme 2, $X^2$ represents a halogen group, and iodine, bromine, and chlorine are preferred as the halogen group.

In the case where bromination is carried out in the reaction scheme 2, bromine, N-bromosuccinimide, and the like are exemplified as a bromination reagent. As the solvent which can be used in the bromination with bromine, a chlorinated solvent such as chloroform, tetrachloromethane are represented. Examples for the solvent which can be used in the bromination with N-bromosuccinimide are ethyl acetate, tetrahydrofuran, N,N-dimethylformamide, acetic acid, water, and the like.

In the case where iodination is carried out in the reaction scheme 2, N-iodosuccinimide, 1,3-diiodo-5,5-dimethylimidazolidine-2,4-dione (abbreviated to DIH), 2,4,6,8-tetraiodo-2,4,6,8-tetraazabicyclo[3,3,0]octane-3,7-dione, 2-iodo-2,4,6,8-tetraazabicyclo[3,3,0]octane-3,7-dione, and the like can be represented as an iodination reagent. When the iodination is carried out by using these iodination reagents, the following can be used singly or in combination as a solvent: a protic solvent such as acetic acid (glacial acetic acid) and water; an aromatic hydrocarbon such as benzene, toluene, and xylene; an ether such as 1,2-dimethoxyethane, diethyl ether, methyl tert-butyl ether, tetrahydrofuran, and dioxane; a saturated hydrocarbon such as pentane, hexane, heptane, octane, and cyclohexane; a halogenated solvent such as dichloromethane, chloroform, tetrachloromethane, and 1,2-dichloroethane, 1,1,1-trichloroethane; a nitrite such as acetonitrile and benzonitrile; an ester such as ethyl acetate, methyl acetate, and butyl acetate; and the like. When water is used, it is preferably mixed with an organic solvent. Moreover, it is preferred to conduct the reaction in the presence of an acid such as sulfuric acid and acetic acid.

tecting the boronic acid unit of compound 5 by ethylene glycol, pinacol, or the like may be used instead of compound 5.

As the palladium catalyst which can be used in the reaction scheme 3, palladium(II) acetate, tetrakis(triphenylphosphine)platinum(0), and the like are represented. Examples of ligands of the palladium catalysts which can be used in the reaction scheme 3 are tri(o-tolyl)phosphine, triphenylphosphine, tricyclohexylphosphine, and the like. Examples of bases which can be used in the reaction scheme 3 are organic bases such as sodium tert-butoxide, inorganic bases such as potassium carbonate, and the like. Examples of solvents which can be used in the reaction scheme 3 are as follows: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane, and water; and the like. Among them, a mixed solvent of toluene and water or a mixed solvent of toluene, ethanol, and water is more preferable.

Next, a synthetic method for the organic compound represented by the general formula (G2) which is used in the synthesis of the anthracene derivatives shown in the present embodiment is explained by using the reaction schemes 4 to 6.

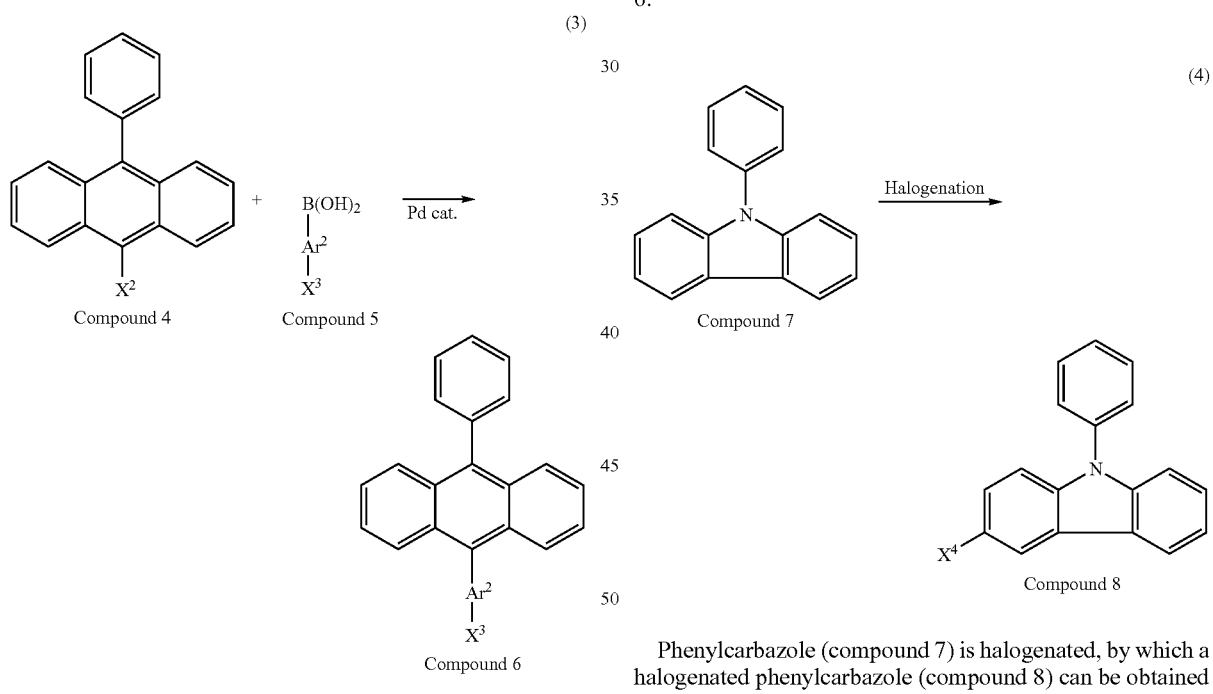

Next, the phenylanthracene derivative (compound 4) obtained by the reaction scheme 2 and a halogenated arylboronic acid (compound 5) are subjected to the coupling of the Suzuki-Miyaura reaction in the presence of a palladium catalyst, resulting in the formation of a halogenated diarylanthracene derivative (compound 6) (reaction scheme 3).

In the reaction scheme 3, $X^2$ and $X^3$ each represent a halogen group, and iodine and bromine are preferred as the halogen group. Note that $X^2$ and $X^3$ are preferred to be iodine and bromine, respectively, in order to suppress the homocoupling of compound 5. In the reaction scheme 3, $Ar^2$ represents a phenylene group or a biphenyl-4,4'-diyl group. In this reaction, an organoboron compound, which is obtained by pro- Phenylcarbazole (compound 7) is halogenated, by which a halogenated phenylcarbazole (compound 8) can be obtained (reaction scheme 4).

In the reaction scheme 4, $X^3$ represents a halogen group, and iodine and bromine are preferred as the halogen group.

In the case of bromination of compound 7 in the reaction scheme 4, bromine, N-bromosuccinimide, and the like are exemplified as a bromination reagent. As the solvent which can be used in the bromination with bromine, a chlorinated solvent such as chloroform, and tetrachloromethane are represented. Examples for the solvent which can be used in the bromination with N-bromosuccinimide are ethyl acetate, tetrahydrofuran, N,N-dimethylformamide, acetic acid, water, and the like.

In the case of iodination in the reaction scheme 4, N-iodosuccinimide, 1,3-diiodo-5,5-dimethylimidazolidine-2,4- dione (abbreviated to DIH), 2,4,6,8-tetraiodo-2,4,6,8-tetraazabicyclo[3,3,0]octane-3,7-dione, 2-iodo-2,4,6,8-tetraazabicyclo[3,3,0]octane-3,7-dione, and the like can be represented as an iodination reagent. When the iodination is carried out by using these iodination reagents, the following can be used singly or in combination as a solvent: a protic solvent such as acetic acid (glacial acetic acid) and water; an aromatic hydrocarbon such as benzene, toluene, and xylene; an ether such as 1,2-dimethoxyethane, diethyl ether, methyl tert-butyl ether, tetrahydrofuran, and dioxane; a saturated hydrocarbon such as pentane, hexane, heptane, octane, and cyclohexane; a halogenated solvent such as dichloromethane, chloroform, tetrachloromethane, 1,2-dichloroethane, and 1,1,1-trichloroethane; a nitrile such as acetonitrile and benzonitrile; an ester such as ethyl acetate, methyl acetate, and butyl acetate; and the like. When water is used, it is preferably mixed with an organic solvent. Moreover, it is preferred to conduct the reaction in the presence of an acid such as sulfuric acid and acetic acid simultaneously.

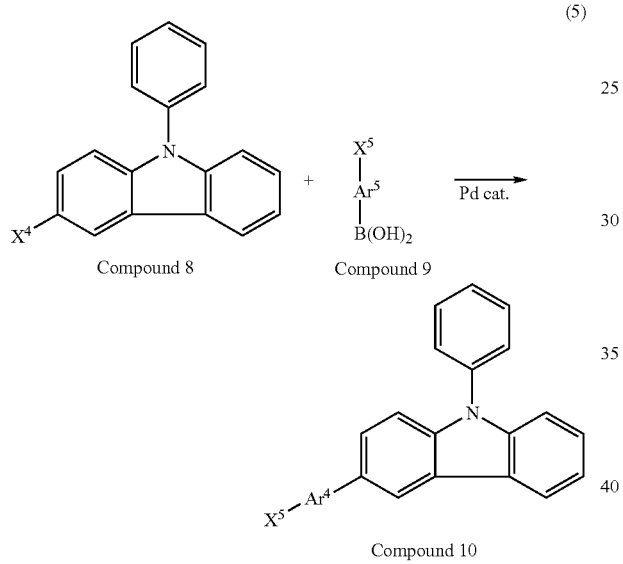

Next, the carbazole derivative (compound 8) and the arylboronic acid (compound 9) are subjected to the coupling by the Suzuki-Miyaura reaction in the presence of a palladium catalyst, resulting in the formation of a carbazole derivative (compound 10).

In the reaction scheme 5, $X^4$ and $X^5$ represent a halogen group, and iodine and bromine are preferred as the halogen group. In the reaction scheme 5, $Ar^4$ represents a phenylene group or a biphenyl-4,4'-diyl group.

As the palladium catalyst which can be used in the reaction scheme 5, palladium(II) acetate, tetrakis(triphenylphosphine)platinum(0), and the like are represented. Examples of ligands of the palladium catalysts which can be used in the reaction scheme 5 are tri(o-tolyl)phosphine, triphenylphosphine, tricyclohexylphosphine, and the like. Examples of bases which can be used in the reaction scheme 5 are organic bases such as sodium tert-butoxide, inorganic bases such as potassium carbonate, and the like. Examples of solvents which can be used in the reaction scheme 5 are as follows: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane, and water; and the like. Among them, a mixed solvent of toluene and water or a mixed solvent of toluene, ethanol, and water is more preferable.

Note that the carbazole derivative (compound 10) can alternatively be synthesized by a method shown in the reaction scheme 5-2. In the method shown in the reaction scheme 5-2, a carbazole derivative (compound 21) is coupled with an aryl halide (compound 22) by the Suzuki-Miyaura reaction in the presence of a palladium catalyst to give the carbazole derivative (compound 10). The method shown by the reaction scheme 5-2 is preferred since it provides a less amount of by-products and facilitates the purification.

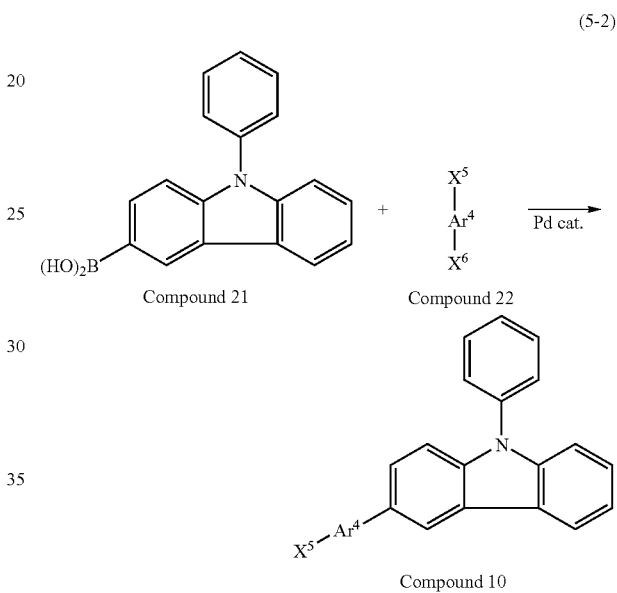

In the reaction scheme 5-2, $X^5$ and $X^6$ represent a halogen group, and iodine and bromine are preferred as the halogen group. In the reaction scheme 5-2, $Ar^4$ represents a phenylene group or a biphenyl-4,4'-diyl group.

As the palladium catalyst which can be used in the reaction scheme 5-2, palladium(II) acetate, tetrakis(triphenylphosphine)platinum(0), and the like are represented. Examples of ligands of the palladium catalysts which can be used in the reaction scheme 5-2 are tri(o-tolyl)phosphine, triphenylphosphine, tricyclohexylphosphine, and the like. Examples of bases which can be used in the reaction scheme 5-2 are organic bases such as sodium tert-butoxide, inorganic bases such as potassium carbonate, and the like. Examples of solvents which can be used in the reaction scheme 5-2 are as follows: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane, and water; and the like. Among them, a mixed solvent of toluene and water or a mixed solvent of toluene, ethanol, and water is more preferable.

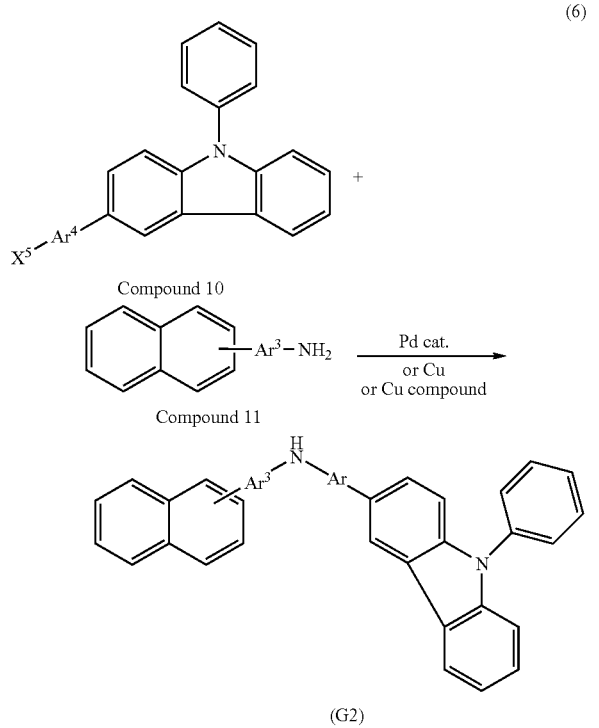

(6)

Compound 10

Compound 11

(G2)

Next, the carbazole derivative (compound 10) which is obtained by the reaction scheme 5 or 5-2 and an arylamine derivative (compound 11) are subjected to the Hartwig-Buchwald reaction using a palladium catalyst or the Ullmann reaction using copper or a copper compound, by which the organic compound (general formula (G2)) shown in the present embodiment can be obtained (reaction scheme 6).

In the reaction scheme 6, $X^5$ represents a halogen group, and iodine and bromine are preferred as the halogen group. In the reaction scheme 6, $Ar^3$ and $Ar^4$ each independently represent a phenylene group or a biphenyl-4,4'-diyl group.

In the case where the Hartwig-Buchwald reaction is carried out in the reaction scheme 6, bis(dibenzylideneacetone)palladium(0), palladium(II) acetate, and the like are provided as the palladium catalyst which can be used. Examples of ligands of the palladium catalysts which can be used in the reaction scheme 6 are tri(tert-butyl)phosphine, tri(n-hexyl)phosphine, tricyclohexylphosphine, and the like. Examples of bases which can be used in the reaction scheme 6 are organic bases such as sodium tert-butoxide, inorganic bases such as potassium carbonate, and the like. The solvents that can be used in the reaction scheme 6 are toluene, xylene, benzene, tetrahydrofuran, and the like.

The case of performing the Ullmann reaction in accordance with the reaction scheme 6 is explained. As the copper compound which can be used in the reaction scheme 6, copper(I) iodide, copper(II) acetate, and the like are represented. Further, copper can be used in addition to the copper compound. Examples of bases which can be used in the reaction scheme 6 are inorganic bases such as potassium carbonate, and the like. A solvent that can be used in the reaction scheme 6 may be 1,3-dimethyl-3,4,5,6-tetrahydro-2(1H)pyrimidinone (abbreviated to DMPU), toluene, xylene, benzene, or the like. In the Ullmann reaction, since the target product can be obtained in a shorter time and in a higher yield when the reaction temperature is 100° C. or higher; therefore, it is preferable to use DMPU or xylene that has a high boiling temperature. Since it is further preferable that the reaction temperature is higher than or equal to 150° C., DMPU is more preferably used.

Next, a synthetic method of the anthracene derivative of the present embodiment that is represented by the general formula (G1) is explained using the reaction scheme 7.

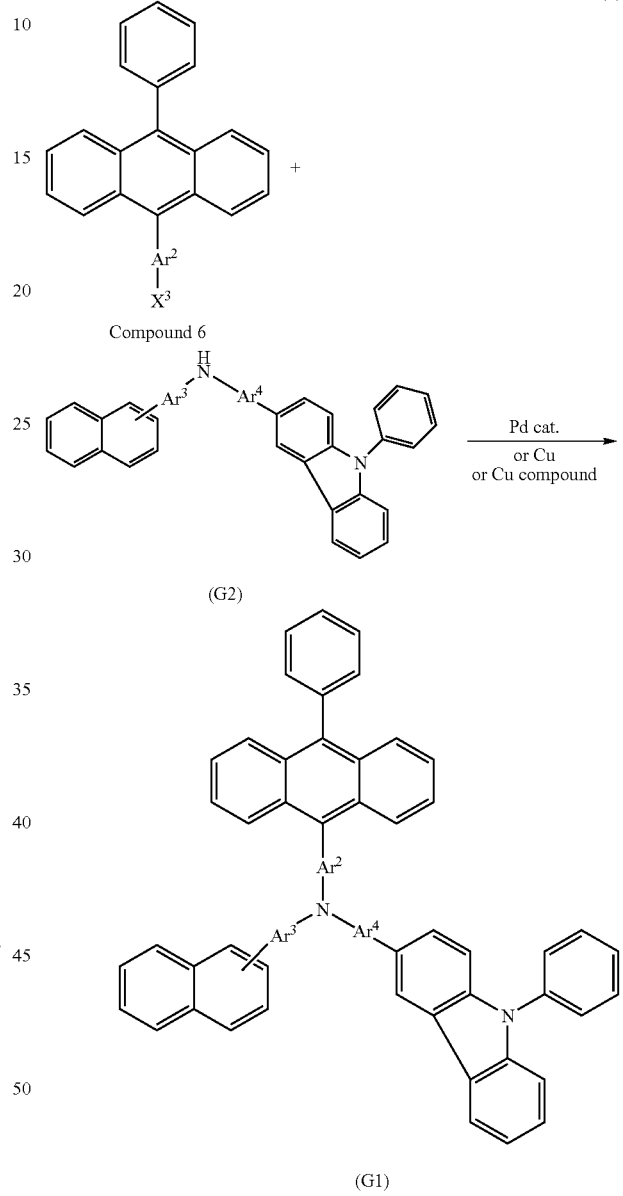

(7)

Compound 6

(G2)

(G1)

The anthracene derivative (compound 6) obtained in the reaction scheme 3 and the organic compound (general formula (G2)) of the present embodiment which is obtained in the reaction scheme 6 are subjected to the Hartwig-Buchwald reaction using a palladium catalyst or the Ullmann reaction using copper or a copper compound, by which the desired compound represented by the general formula (G1) can be obtained (reaction scheme 7).

In the reaction scheme 7, $X^3$ represents a halogen group, and iodine and bromine are preferred as the halogen group. In the reaction scheme 7, $Ar^2$, $Ar^3$, and $Ar^4$ each independently represent a phenylene group or a biphenyl-4,4'-diyl group.

In the case where the Hartwig-Buchwald reaction is carried out in the reaction scheme 7, bis(dibenzylideneacetone)palladium(0), palladium(II) acetate, and the like are provided as the palladium catalyst which can be used. Examples of ligands of the palladium catalysts which can be used in the reaction scheme 7 are tri(tert-butyl)phosphine, tri(n-hexyl)phosphine, tricyclohexylphosphine, and the like. Examples of bases which can be used in the reaction scheme 7 are organic bases such as sodium tert-butoxide, inorganic bases such as potassium carbonate, and the like. The solvents that can be used in the reaction scheme 7 are toluene, xylene, benzene, tetrahydrofuran, and the like.

The case of performing the Ullmann reaction in accordance with the reaction scheme 7 is explained. As the copper compound which can be used in the reaction scheme 7, copper(I) iodide, copper(II) acetate, and the like are represented. Further, copper can be used in addition to the copper compound. Examples of bases which can be used in the reaction scheme 7 are inorganic bases such as potassium carbonate, and the like. A solvent that can be used in the reaction scheme 7 may be 1,3-dimethyl-3,4,5,6-tetrahydro-2(1H)pyrimidinone (abbreviated to DMPU), toluene, xylene, benzene, or the like. In the Ullmann reaction, the target product can be obtained in a shorter time and in a higher yield when the reaction temperature is 100° C. or higher; therefore, it is preferable to use DMPU or xylene that has a high boiling temperature. Since it is further preferable that the reaction temperature is higher than or equal to 150° C., DMPU is more preferably used.

By the above-mentioned methods, the anthracene derivative represented by the general formula (G1) and the organic compound represented by the general formula (G2) can be synthesized.

The anthracene derivative of the present embodiment represented by the general formula (G1) has a naphthyl group at a terminal of an amine skeleton. Accordingly, the anthracene derivative efficiently emits light and is an electrochemically stable compound. Therefore, the anthracene derivative represented by the general formula (G1) can be suitably used for a light-emitting element.

Additionally, since the anthracene derivative represented by the general formula (G1) exhibits blue emission with excellent color purity, it can be suitably used for a light-emitting layer in a light-emitting element.

Embodiment 2

In this embodiment, an embodiment of a light-emitting element using the anthracene derivative shown in Embodiment 1 is described with reference to FIG. 1A.

A light-emitting element described in the present embodiment has a plurality of layers between a pair of electrodes. The plurality of layers are formed by stacking layers including a substance having a high carrier injection property or a substance having a high carrier-transporting property so that a light-emitting region is formed apart from the electrodes, in other words, carriers are recombined in a portion apart from the electrodes.

In this embodiment, the light-emitting element illustrated in FIG. 1A includes a first electrode 101, a second electrode 103, and a layer 102 including an organic compound which is formed between the first electrode 101 and the second electrode 103. Note that in this embodiment, explanation is given below assuming that the first electrode 101 serves as an anode and the second electrode 103 serves as a cathode. That is, in the description below, it is assumed that light emission can be obtained when a voltage is applied to the first electrode 101 and the second electrode 103 so that the potential of the first electrode 101 is higher than that of the second electrode 103.

A substrate 100 is used as a support of the light-emitting element. As the substrate 100, for example, a glass substrate, a plastic substrate, or the like can be used. Alternatively, the substrate 100 may be formed with any other material as long as the material can support the light-emitting element during a manufacturing process.

It is preferred that the first electrode 101 be formed using any of metals, alloys, and conductive compounds with a high work function (specifically, 4.0 eV or higher), a mixture thereof, or the like. Specifically, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), or the like can be used. These conductive metal oxide films are generally formed by sputtering; however, the films may be formed by applying a sol-gel method. For example, indium oxide-zinc oxide (IZO) can be formed by a sputtering method using indium oxide into which 1 to 20 wt % of zinc oxide is added, as a target. Indium oxide containing tungsten oxide and zinc oxide (IWZO) can be formed by a sputtering method using a target in which 0.5 to 5 wt % of tungsten oxide and 0.1 to 1 wt % of zinc oxide are mixed with indium oxide. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal (such as titanium nitride), or the like can be given.

When a layer including a composite material which is described later is used as a layer that is in contact with the first electrode 101, the first electrode 101 can be formed using any of a variety of metals, an alloy, a conductive compound, a mixture of them, or the like regardless of their work functions. For example, aluminum (Al), silver (Ag), an aluminum alloy (e.g., AlSi), or the like can be used. Further, a metal of an element belonging to Group 1 or Group 2 in the periodic table, which is a low work function material, that is, an alkali metal such as lithium (Li) or cesium (Cs), an alkaline earth metal such as magnesium (Mg), calcium (Ca), or strontium (Sr), an alloy including these metals (such as an MgAg alloy or an AlLi alloy), a rare earth metal such as europium (Eu) or ytterbium (Yb), an alloy including such rare earth metals, or the like can be used. A film of an alkali metal, an alkaline earth metal, or an alloy including these metals can be formed by a vacuum evaporation method. In addition, an alloy including an alkali metal or an alkaline earth metal can be formed by a sputtering method. Further, silver paste or the like can be applied by an ink-jet method to form the first electrode 101.

There is no particular limitation on the stack structure of the layer 102 including an organic compound. The layer 102 including an organic compound may have a structure in which one or more of layers including a substance having a high electron-transporting property, a substance having a high hole-transporting property, substance having a high electron injection property, a substance having a high hole injection property, a bipolar substance (a substance having a high electron-transporting property and a high hole-transporting property), and/or the like is combined with the light-emitting layer described in this embodiment, as appropriate. For example, it is possible to combine a hole injection layer, a hole-transporting layer, an electron-transporting layer, an electron injection layer, and the like with the light-emitting layer described in this embodiment to form the layer 102 including an organic compound. In the present embodiment, explanation is given on a structure in which the layer 102 including an organic compound comprises a hole injection layer 111, a hole-transporting layer 112, a light-emitting layer 113, and an electron-transporting layer 114 stacked in that order over the first electrode 101. Specific materials to form each of the layers will be given below.

The hole injection layer 111 is a layer including a substance having a high hole injection property. Molybdenum oxide, vanadium oxide, ruthenium oxide, tungsten oxide, manganese oxide, and the like can be used as the hole injection layer. Alternatively, the hole injection layer 111 can be formed using any one of the following materials: phthalocyanine based compounds such as phthalocyanine (abbreviated to $H_2PC$) and copper phthalocyanine (abbreviated to CuPc); aromatic amine compounds such as 4,4'-bis[N-(4-diphenylaminophenyl)-N-phenylamino]biphenyl (abbreviated to DPAB) and 4,4'-bis(N-{4-[N-(3-methylphenyl)-N-phenylamino]phenyl}-N-phenylamino)biphenyl (abbreviated to DNTPD); high molecular compounds such as poly(ethylenedioxythiophene)/poly(styrenesulfonic acid) (abbreviated to PEDOT/PSS); and the like.

As a further alternative, a composite material formed by mixing an acceptor substance into a substance with a high hole-transporting property can also be used for the hole injection layer 111. It is to be noted that, by using a composite containing the substance with a high hole-transporting property and an acceptor substance, a material used to form an electrode may be selected regardless of its work function. That is, not only a high-work function material, but also a low-work function material can be used for the first electrode 101. As the acceptor substance, 7,7,8,8-tetracyano-2,3,5,6-tetrafluoroquinodimethane (abbreviated to $F_4$-TCNQ), chloranil, and the like can be given. In addition, a transition metal oxide is given. Furthermore, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of a high electron accepting property. Among these metal oxides, molybdenum oxide is especially preferable since it is stable in the air and its hygroscopic property is low so that it can be easily treated.

As a substance with a high hole-transporting property used for the composite material, various compounds such as aromatic amine compounds, carbazole derivatives, aromatic hydrocarbons, and high molecular compounds (such as oligomer, dendrimer, or polymer) can be used. Note that the substance having a hole mobility of $10^{-6}$ cm$^2$/Vs or more is preferably used as the substance having a high hole-transporting property used for the composite material. However, any other substance may be used as long as it has a hole-transporting property higher than an electron-transporting property. The organic compound that can be used for the composite material is specifically shown below.

Examples of the aromatic amine compounds that can be used for the composite material include 4,4'-bis[N-(1-naphthyl)-N-phenylamino]biphenyl (abbreviated to NPB), N,N'-bis(4-methylphenyl)(p-tolyl)-N,N'-diphenyl-p-phenylenediamine (abbreviated to DTDPPA), 4,4'-bis[N-(4-diphenylaminophenyl)-N-phenylamino]biphenyl (abbreviated to DPAB), 4,4'-bis(N-{4-[N,N-bis(3-methylphenyl)amino]phenyl}-N-phenylamino)biphenyl (abbreviated to DNTPD), 1,3,5-tris[N-(4-diphenylaminophenyl)-N-phenylamino]benzene (abbreviated to DPA3B), and the like.

Specific examples of the carbazole derivatives that can be used for the composite material include 3-[N-(9-phenylcarbazol-3-yl)-N-phenylamino]-9-phenylcarbazole (abbreviated to PCzPCA1), 3,6-bis[N-(9-phenylcarbazol-3-yl)-N-phenylamino]-9-phenylcarbazole (abbreviated to PCzPCA2), 3-[N-(1-naphthyl)-N-(9-phenylcarbazol-3-yl)amino]-9-phenylcarbazole (abbreviated to PCzPCN1), 4,4'-di(N-carbazolyl)biphenyl (abbreviated to CBP), 1,3,5-tris[4-(N-carbazolyl)phenyl]benzene (abbreviated to TCPB), 9-[4-(10-phenyl-9-anthracenyl)phenyl]-9H-carbazole (abbreviated to CzPA), 1,4-bis[4-(N-carbazolyl)phenyl]-2,3,5,6-tetraphenylbenzene, and the like.

As the aromatic hydrocarbons which can be used for the composite material, the following can be given for example: 2-tert-butyl-9,10-di(2-naphthyl)anthracene (abbreviated to t-BuDNA); 2-tert-butyl-9,10-di(1-naphthyl)anthracene, 9,10-bis(3,5-diphenylphenyl)anthracene (abbreviated to DPPA); 2-tert-butyl-9,10-bis(4-phenylphenyl)anthracene (abbreviated to t-BuDBA); 9,10-di(2-naphthyl)anthracene (abbreviated to DNA); 9,10-diphenylanthracene (abbreviated to DPAnth); 2-tert-butylanthracene (abbreviated to t-BuAnth);
9,10-bis(4-methyl-1-naphthyl)anthracene (abbreviated to DMNA);
9,10-bis[2-(1-naphthyl)phenyl]-2-tert-butyl-anthracene;
9,10-bis[2-(1-naphthyl)phenyl]anthracene;
2,3,6,7-tetramethyl-9,10-di(1-naphthyl)anthracene;
2,3,6,7-tetramethyl-9,10-di(2-naphthyl)anthracene; 9,9'-bianthryl;
10,10'-diphenyl-9,9'-bianthryl; 10,10'-bis(2-phenylphenyl)-9,9'-bianthryl;
10,10'-bis[(2,3,4,5,6-pentaphenyl)phenyl]-9,9'-bianthryl;
anthracene; tetracene; rubrene; perylene; 2,5,8,11-tetra(tert-butyl)perylene; and the like. In addition, pentacene, coronene, or the like can also be used. In particular, the aromatic hydrocarbon which has a hole mobility of $1 \times 10^{-6}$ cm$^2$/Vs or higher and which has 14 to 42 carbon atoms is particularly preferable.

The aromatic hydrocarbons that can be used for the composite material may have a vinyl skeleton. As an aromatic hydrocarbon having a vinyl group, for example, 4,4'-bis(2,2-diphenylvinyl)biphenyl (abbreviated to DPVBi), 9,10-bis[4-(2,2-diphenylvinyl)phenyl]anthracene (abbreviated to DPVPA), and the like are given.

For the hole injection layer 111, a high molecular compound (e.g., an oligomer, a dendrimer, or a polymer) can be used. For example, the following high molecular compound can be used: poly(N-vinylcarbazole) (abbreviated to PVK); poly(4-vinyltriphenylamine) (abbreviated to PVTPA); poly[N-(4-{N'-[4-(4-diphenylamino)phenyl]phenyl-N'-phenylamino}phenyl)methacrylamide] (abbreviated to PTPDMA); poly[N,N'-bis(4-butylphenyl)-N,N'-bis(phenyl)benzidine] (abbreviated to Poly-TPD); and the like. In addition, high molecular compounds doped with acid such as poly(3,4-ethylenedioxythiophene)/poly(styrenesulfonic acid) (PEDOT/PSS), polyaniline/poly(styrenesulfonic acid) (PAni/PSS), and the like can be used.

It is to be noted that the hole injection layer 111 can be formed using a composite material of the above-described high molecular compound, such as PVK, PVTPA, PTPDMA, or Poly-TPD, and the above-described acceptor substance.

The hole-transporting layer 112 is a layer that contains a substance with a high hole-transporting property. As the substance with a high hole-transporting property, for example, an aromatic amine compound such as 4,4'-bis[N-(1-naphthyl)-N-phenylamino]biphenyl (abbreviated to NPB), N,N'-bis(3-methylphenyl)-N,N'-diphenyl)[1,1'-biphenyl]-4,4'-diamine (abbreviated to TPD), 4,4',4''-tris(N,N-diphenylamino)triphenylamine (abbreviated to TDATA), 4,4',4''-tris[N-(3-methylphenyl)-N-phenylamino]triphenylamine (abbreviated to MTDATA), or 4,4'-bis[N-(spiro-9,9'-bifluoren-2-yl)-N-phenylamino]biphenyl (abbreviated to BSPB) can be used. The materials described here are mainly materials having hole mobility of $10^{-6}$ cm$^2$/Vs or more. However, any substances may be used as long as the hole-transporting property thereof is higher than the electron-transporting property. Note that the layer containing a substance with high a hole-transporting property is not limited to be a single layer, and two or more layers containing the aforementioned substances may be stacked.

For the hole-transporting layer 112, a high molecular compound such as PVK, PVTPA, PTPDMA, or Poly-TPD can be used alternatively.

The light-emitting layer 113 is a layer including a substance with a high light-emitting property. In the light-emitting element of this embodiment, the light-emitting layer 113 is formed using any of the anthracene derivatives shown in Embodiment 1. The anthracene derivatives shown in Embodiment 1 are suitable for the use in a light-emitting element as a substance having a high light-emitting property because they exhibit high emission efficiency.

The electron-transporting layer 114 is a layer containing a substance with a high electron-transporting property. For example, it is possible to employ a metal complex or the like having a quinoline or benzoquinoline skeleton, such as tris(8-quinolinolato)aluminum (abbreviated to Alq), tris(4-methyl-8-quinolinolato)aluminum (abbreviated to Almq$_3$), bis(10-hydroxybenzo[h]quinolinato)beryllium (abbreviated to BeBq$_2$), or bis(2-methyl-8-quinolinolato)(4-phenylphenolato)aluminum (abbreviated to BAlq) for the electron-transporting layer 114. Alternatively, a metal complex having an oxazole-based or thiazole-based ligand, such as bis[2-(2-hydroxyphenyl)benzoxazolato]zinc (abbreviated to Zn(BOX)$_2$) or bis[2-(2-hydroxyphenyl)benzothiazolato]zinc (abbreviated to Zn(BTZ)$_2$) can be used. Besides the metal complexes, 2-(4-biphenylyl)-5-(4-tert-butylphenyl)-1,3,4-oxadiazole (abbreviated to PBD), 1,3-bis[5-(p-tert-butylphenyl)-1,3,4-oxadiazole-2-yl]benzene (abbreviated to OXD-7), 3-(4-biphenylyl)-4-phenyl-5-(4-tert-butylphenyl)-1,2,4-triazole (abbreviated to TAZ), bathophenanthroline (abbreviated to BPhen), bathocuproine (abbreviated to BCP), or the like can also be used. The substances described here are mainly substances having electron mobility of $10^{-6}$ cm$^2$/Vs or more. It is to be noted that a substance other than the above substances may be used as tong as it has a higher electron-transporting property than a hole-transporting property. Further, the electron-transporting layer may be formed by not only as a single layer but also as a stacked form in which two or more layers made from the above-mentioned substances are stacked.

For the electron-transporting layer 114, a high molecular compound can be used. For example, poly[(9,9-dihexylfluorene-2,7-diyl)-co-(pyridine-3,5-diyl)] (abbreviated to PF-Py), poly[(9,9-dioctylfluorene-2,7-diyl)-co-(2,2'-bipyridine-6,6'-diyl)] (abbreviated to PF-BPy), and the like can be used.

An electron injection layer may be provided between the electron-transporting layer 114 and the second electrode 103. The electron injection layer can be formed using an alkali metal compound or an alkaline earth metal compound such as lithium fluoride (LiF), cesium fluoride (CsF), or calcium fluoride (CaF$_2$). Furthermore, a layer, in which a substance having an electron-transporting property is combined with an alkali metal or an alkaline earth metal, can be employed. For instance, a layer comprising Alq to which magnesium (Mg) is added can be used. It is more preferable to use the layer, in which a substance having an electron-transporting property is combined with an alkali metal or an alkaline earth metal, as the electron injection layer because electron injection from the second electrode 103 efficiently proceeds.

The second electrode 103 can be formed using a metal, an alloy, or a conductive compound with a low work function (specifically, 3.8 eV or lower), a mixture of them, or the like. Specific examples of such cathode materials include elements belonging to Group 1 and 2 of the periodic table, i.e., alkali metals such as lithium (Li) and cesium (Cs) and alkaline earth metals such as magnesium (Mg), calcium (Ca), and strontium (Sr); alloys of them (e.g., MgAg and AlLi); rare earth metals such as europium (Eu) and ytterbium (Yb), alloys of them; and the like. A film of an alkali metal, an alkaline earth metal, or an alloy including these metals can be formed by a vacuum evaporation method. In addition, an alloy including an alkali metal or an alkaline earth metal can be formed by a sputtering method. Further, silver paste or the like can be applied by an ink-jet method to form the second electrode 103.

When the electron injection layer is provided between the second electrode 103 and the electron-transporting layer 114, any of a variety of conductive materials such as Al, Ag, ITO, and indium oxide-tin oxide containing silicon or silicon oxide can be used for the second electrode 103 regardless of its work function. These conductive materials can be formed by a sputtering method, an ink-jet method, a spin coating method, or the like.

In the light-emitting element shown in this embodiment having the above-mentioned structure, a current flows by application of voltage between the first electrode 101 and the second electrode 103. Then, holes and electrons are recombined in the light-emitting layer 113 that is a layer containing a substance with a high light-emitting property. That is, the light-emitting element has a structure in which a light-emitting region is formed in the light-emitting layer 113.

Light is extracted outside through one or both of the first electrode 101 and the second electrode 103. Thus, one or both of the first electrode 101 and the second electrode 103 are light-transmitting electrodes. When only the first electrode 101 is a light-transmitting electrode, light is extracted from the substrate 100 side through the first electrode 101. In contrast, when only the second electrode 103 is a light-transmitting electrode, light is extracted from a side opposite to the substrate 100 side through the second electrode 103. When both the first electrode 101 and the second electrode 103 are light-transmitting electrodes, light is extracted from both the substrate 100 side and the side opposite to the substrate 100 side through the first electrode 101 and the second electrode 103.

Although FIG. 1A shows a structure in which the first electrode 101 that functions as an anode is provided on the substrate 100 side, the second electrode 103 that functions as a cathode may be provided on the substrate 100 side.

Any of a variety of methods can be employed for forming the layer 102 including an organic compound regardless of whether it is a dry process or a wet process. Moreover, a different forming method may be used for each electrode or each layer. A vacuum evaporation method, a sputtering method, or the like can be employed as a dry process. An ink-jet method, a spin-coating method, or the like can be employed as a wet process.

Further, the electrodes may be formed by a sol-gel method, which is a wet process, or may also be formed by a wet process using a paste of a metal material. Further, the electrode may be formed by a dry method such as a sputtering method or a vacuum evaporation method.

Hereinafter, specific methods of forming a light-emitting element are described. When the light-emitting element shown in this embodiment is applied to a display device and its light-emitting layer is separately coated, the light-emitting layer is preferably formed by a wet process. The use of a wet process such as an ink-jet method makes it easier to form light-emitting layers separately for each color even if a large substrate is employed, whereby productivity is improved.

For example, in the structure described in this embodiment, the first electrode 101 may be formed by a sputtering method, which is a dry process; the hole injection layer 111 may be formed by an ink-jet method or a spin coating method, which are wet processes; the hole-transporting layer 112 may be formed by a vacuum evaporation method, which is a dry process; the light-emitting layer 113 may be formed by an ink-jet method, which is a wet process; the electron-transporting layer 114 may be formed by a co-deposition method, which is a dry process; and the second electrode 103 may be formed by an ink-jet method or a spin coating method, which are wet processes. Furthermore, the first electrode 101 may be formed by an ink-jet method, which is a wet process; the hole injection layer 111 may be formed by a vacuum evaporation method, which is a dry process; the hole-transporting layer 112 may be formed by an ink-jet method or a spin coating method, which are wet processes; the light-emitting layer 113 may be formed by an ink-jet method, which is a wet process; the electron-transporting layer 114 may be formed by an ink-jet method or a spin coating method, which are wet processes; and the second electrode 103 may be formed by an ink-jet method or a spin coating method, which are wet processes. The method for forming the light-emitting element is not particularly limited to the above methods, and a wet method and a dry method may be combined as appropriate.

For example, the first electrode 101 may be formed by a sputtering method which is a dry process; the hole injection layer 111 and the hole-transporting layer 112 may be formed by an ink-jet method or a spin coating method, which are wet processes; the light-emitting layer 113 may be formed by an ink-jet method which is a wet process; the electron-transporting layer 114 may be formed by a vacuum evaporation method, which is a dry process; and the second electrode 103 may be formed by a vacuum evaporation method which is a dry process. That is, it is possible to form the hole injection layer 111 to the light-emitting layer 113 by wet processes and to form the electron-transporting layer 114 to the second electrode 103 by dry processes over the substrate 100 over which the first electrode 101 is formed in a desired shape. By this method, the hole injection layer 111 to the light-emitting layer 113 can be formed at atmospheric pressure, and the light-emitting layer 113 can be readily and selectively deposited according to each color. In addition, the electron-transporting layer 114 to the second electrode 103 can be formed in vacuum consistently. Therefore, the processes can be simplified, and productivity can be improved.

When the light-emitting layer 113 is formed by a wet process, a liquid composition in which any of the anthracene derivatives shown in Embodiment 1 are dissolved in a solvent can be used. In this case, the liquid composition comprising any of the anthracene derivatives shown in Embodiment 1 and a solution is applied to a region where the light-emitting layer 113 is to be formed, the solvent is then removed by heat treatment or the like, and the anthracene derivative shown in Embodiment 1 is solidified, whereby a thin film of the light-emitting layer 113 is formed.

As to the light-emitting element with the above-mentioned structure shown in the present embodiment, a current flows when a potential difference is given between the first electrode 101 and the second electrode 103, and then holes and electrons are recombined in the light-emitting layer 113, which is the layer including a substance having a high light-emitting property, resulting in emission of light. That is, the light-emitting element has a structure in which a light-emitting region is formed in the light-emitting layer 113.

Note that a structure of the layers provided between the first electrode 101 and the second electrode 103 is not limited to the structure described above. Any other structure can be employed as long as a light-emitting region in which holes and electrons are recombined is provided away from the first electrode 101 and the second electrode 103 in order to prevent quenching of emitted light which is caused by the approach of the light-emitting region to a metal.

The anthracene derivatives shown in Embodiment 1 have high emission efficiency; therefore, as described in this embodiment, they can be used for a light-emitting layer without adding any other light-emitting substance. Furthermore, since the anthracene derivatives shown in Embodiment 1 have high emission efficiency, a light-emitting element with high emission efficiency can be obtained.

Since the anthracene derivatives shown in Embodiment 1 emit blue light with excellent color purity, a light-emitting element which exhibits blue light emission with excellent color purity can be obtained.

Additionally, since the anthracene derivatives shown in Embodiment 1 are able to emit blue light with excellent color purity at high efficiency, a light-emitting element which can emit blue light with high luminous efficiency can be obtained.

Furthermore, since the anthracene derivatives shown in Embodiment 1 are electrochemically stable, a blue emissive light-emitting element having a long lifetime can be obtained.

Further, since a light-emitting element that uses any of the anthracene derivatives shown in Embodiment 1 can emit blue light at high efficiency, the light-emitting element is suitable for use in a full-color display. Moreover, the light-emitting element can emit blue light for a long period of time; therefore, the light-emitting element is suitable for use in a full-color display. In particular, blue emissive light-emitting elements are less developed in terms of lifetime and efficiency than green emissive or red emissive light-emitting elements; therefore, high performance blue emissive light-emitting elements have been desired. A light-emitting element using any of the anthracene derivatives shown in Embodiment 1 are capable emitting blue light at high efficiency and exhibiting a long lifetime and thus is suitable for a full-color display.

Embodiment 3

In this embodiment, description is made of a light-emitting element having a different structure from that described in Embodiment 2.

The light-emitting layer 113 shown in Embodiment 2 is formed by dispersing the anthracene derivative shown in Embodiment 1 into another substance, whereby light emission can be obtained from the anthracene derivative shown in Embodiment 1. With the anthracene derivative shown in Embodiment 1 which emits blue light, a blue emissive light-emitting element can be provided.

As the substance in which the anthracene derivative shown in Embodiment 1 is dispersed, various materials can be used: 4,4'-bis(N-carbazolyl)-biphenyl (abbreviated to CBP), 2,2', 2"-(1,3,5-benzenetri-yl)-tris[1-phenyl-1H-benzimidazole] (abbreviated to TPBI), 9,10-di(2-naphthyl)anthracene (abbreviated to DNA), 2-tert-butyl-9,10-di(2-naphthyl)anthracene (abbreviated to t-BuDNA), 9-[4-(N-carbazolyl)phenyl]-10-phenylanthracene (abbreviated to CzPA), and the like in addition to the substance with a high hole-transporting property and the substance with a high electron-transporting property described in Embodiment 2. Further, as the substance in which the anthracene derivative shown in Embodiment 1 is dispersed, a high molecular compound can be used. For example, poly(N-vinylcarbazole) (abbreviated to PVK); poly(4-vinyltriphenylamine) (abbreviated to PVTPA); poly[N-(4-{N'-[4-(4-diphenylamino)phenyl]phenyl-N'-phenylamino}phenyl)methacrylamide] (abbreviated to PTPDMA); poly[N,N'-bis(4-butylphenyl)-N,N'-bis(phenyl)benzidine] (abbreviated to Poly-TAD); poly[(9,9-dihexylfluorene-2,7-diyl)-co-(pyridine-3,5-diyl)] (abbreviated to PF-Py); poly[(9,9-dioctylfluorene-2,7-diyl)-co-(2,2'-bipyridine-6,6'-diyl)] (abbreviated to PF-BPy); or the like can be used.

Since the anthracene derivative shown in Embodiment 1 has high emission efficiency, a light-emitting element with high emission efficiency can be obtained by using the anthracene derivative.

Since the anthracene derivatives shown in Embodiment 1 emit blue light with high color purity, a light-emitting element that emits blue light with high color purity can be obtained.

Furthermore, the anthracene derivatives shown in Embodiment 1 emit light at high efficiency, and thus a light-emitting element that can emit blue light with high emission efficiency can be obtained.

Furthermore, by the use of any of the anthracene derivatives shown in Embodiment 1, a light-emitting element with a long lifetime can be obtained.

Since the light-emitting element in which any of the anthracene derivatives shown in Embodiment 1 is used can emit blue light with high color purity at high efficiency, the light-emitting element is suitable for use in a full-color display. Further, since the light-emitting element can emit blue light and exhibit a long lifetime, the light-emitting element is suitable for the use in a full-color display.

Note that, regarding the layers other than the light-emitting layer 113, the structure shown in Embodiment 2 can be used as appropriate.

Embodiment 4

In this embodiment mode, description is made on a light-emitting element having a different structure from those described in Embodiments 2 and 3 with reference to FIG. 1A.

The light-emitting layer 113 shown in Embodiment 2 is formed by dispersing a light-emitting substance in the anthracene derivative shown in Embodiment 1, whereby light emission from the light-emitting substance can be obtained.

When the anthracene derivative shown in Embodiment 1 is used as a material in which another light-emitting substance is dispersed, emission color resulting from the light-emitting substance can be obtained. Alternatively, light with mixed colors resulting from the anthracene derivative shown in Embodiment 1 and from the light-emitting substance dispersed in the anthracene derivative can be emitted.

Here, a variety of materials can be used as the light-emitting substance dispersed in the anthracene derivative shown in Embodiment 1. In specific, the following fluorescent substances which emit fluorescence can be used: N,N"-diphenylquinacridone (abbreviated to DPQd), coumarin 6, coumarin 545T, 4-(dicyanomethylene)-2-methyl-6-(p-dimethylaminostyryl)-4H-pyran (abbreviated to DCM1), 4-(dicyanomethylene)-2-methyl-6-(julolidin-4-yl-vinyl)-4H-pyran (abbreviated to DCM2), N,N"-dimethylquinacridone (abbreviated to DMQd), {2-(1,1-dimethylethyl)-6-[2-(2,3,6,7-tetrahydro-1,1,7,7-tetramethyl-1H,5H-benzo[ij]quinolizin-9-yl)ethenyl]-4H-pyran-4-ylidene}propanedinitrile (abbreviated to DCJTB), 5,12-diphenyltetracene (abbreviated to DPT), N,9-diphenyl-N-[4-(10-phenyl-9-anthryl)phenyl]-9H-carbazol-3-amine (abbreviated to PCAPA), N,N"-(2-tert-butyl-9,10-anthracenediyldi-4,1-phenylene)bis[N,N',N'-triphenyl-1,4-benzenediamine] (abbreviated to DPABPA), N,N'-diphenyl-N,N'-bis(9-phenyl-9H-carbazol-3-yl)stilbene-4,4'-diamine (abbreviated to PCA2S), 2,5,8,11-tetra(tert-butyl)perylene (abbreviated to TBP), perylene, rubrene, 1,3,6,8-tetraphenylpyrene, and the like. Further, phosphorescent substances that emit phosphorescence such as (acetylacetonato)bis[2,3-bis(4-fluorophenyl)quinoxalinato]iridium(III) (abbreviated to Ir(Fdpq)$_2$(acac)) and 2,3,7,8,12,13,17,18-octaethyl-21H,23H-porphyrinplatinum(II) (abbreviated to PtOEP) can be used.

Note that, regarding the layers other than the light-emitting layer 113, the structure shown in Embodiment 2 can be used as appropriate.

Embodiment 5

In this embodiment, a light-emitting element having a structure different from those of described in Embodiments 2 to 4 will be described using FIG. 18.

In the light-emitting element described in this embodiment, a first layer 121 and a second layer 122 are provided in the light-emitting layer 113 of the light-emitting element shown in Embodiment 2.

The light-emitting layer 113 is a layer that includes a substance having a high light-emitting property. In the light-emitting element shown in the present embodiment, the light-emitting layer 113 has the first layer 121 and the second layer 122. The first layer 121 includes a first organic compound and an organic compound having a hole-transporting property, and the second layer 122 includes a second organic compound and an organic compound having an electron-transporting property. The first layer 121 is provided in contact with the first electrode side of the second layer 122, that is, in contact with the anode side of the second layer 122.

Each of the first organic compound and the second organic compound is a substance having a high light-emitting property. In the light-emitting element shown in this embodiment, the first organic compound or the second organic compound contains any of the anthracene derivatives shown in Embodiment 1. Since the anthracene derivatives shown in Embodiment 1 emit blue light with high color purity, the anthracene derivatives are each suitable for use as a substance having a high light-emitting property in the light-emitting element described in this embodiment. Note that the first organic compound and the second organic compound may be the same or different from each another.

When any of the anthracene derivatives shown in Embodiment 1 is used as one of the first organic compound and the second organic compound, as the other one thereof, it is possible to use substances that emit blue light, such as 4-(9H-carbazol-9-yl)-4'-(10-phenyl-9-anthryl)triphenylamine (abbreviated to YGAPA), 4,4'-(2-tert-butylanthracen-9,10-diyl)bis{N-[4-(9H-carbazol-9-yl)phenyl]-N-phenylaniline} (abbreviated to YGABPA), N,9-diphenyl-N-[4-(10-phenyl-9-anthryl)phenyl]-9H-carbazol-3-amine (abbreviated to PCAPA), N,N"-(2-tert-butylanthracene-9,10-diyldi-4,1-phenylene)bis[N,N',N'-triphenyl-1,4-phenylenediamine] (abbreviated to DPABPA), N,N'-bis[4-(9H-carbazol-9-yl)phenyl]-N,N'-diphenylstilbene-4,4'-diamine (abbreviated to YGA2S), N-[4-(9H-carbazol-9-yl)phenyl]-N-phenylstilbene-4-amine (abbreviated to YGAS), N,N'-diphenyl-N,N'-bis(9-phenylcarbazol-3-yl)stilbene-4,4'-diamine (abbreviated to PCA2S), 4,4'-bis(2,2-diphenylvinyl)biphenyl (abbreviated to DPVBi), 2,5,8,11-tetra(tert-butyl)perylene (abbreviated to TBP), perylene, rubrene, and 1,3,6,8-tetraphenylpyrene. Since each of these substances exhibits light with color that is similar to that of the anthracene derivatives shown in Embodiment 1, they are suitable for use in the light-emitting element of this embodiment.

The organic compound having a hole-transporting property, which is contained in the first layer 121, is a substance having a hole-transporting property higher than an electron-transporting property. The organic compound having an electron-transporting property included in the second layer 122 is a substance having an electron-transporting property higher than a hole-transporting property.

Figure 1B:
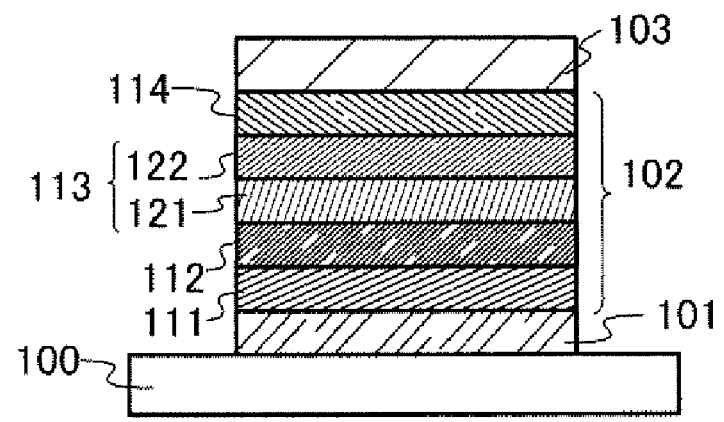

The driving mechanism of the light-emitting element having the above-described structure is described using FIG. 1B.

In FIG. 1B, holes are injected from the first electrode 101 into the first layer 121 of the light-emitting layer 113 through the hole injection layer 111 and the hole-transporting layer 112. The holes injected into the first layer 121 are transported through the first layer 121 and further injected to the second layer 122. Here, the organic compound having an electron-transporting property which is included in the second layer 122 is a substance which exhibits an electron-transporting property higher than a hole-transporting property, and thus, the holes injected into the second layer 122 are difficult to move. Consequently, a large number of holes are stored in the vicinity of the interface between the first layer 121 and the second layer 122. In addition, a phenomenon in which holes reach the electron-transporting layer 114 without recombining with electrons can be suppressed.

Meanwhile, electrons are injected from the second electrode 103 into the second layer 122 of the light-emitting layer 113 through the electron-transporting layer 114. The electrons injected to the second layer 122 are transported through the second layer 122 and further injected to the first layer 121. Here, the organic compound having a hole-transporting property included in the first layer 121 is a substance which exhibits a hole-transporting property higher than an electron-transporting property, and thus, the electrons injected into the first layer 121 are difficult to move. As a result, a phenomenon in which electrons reach the hole-transporting layer 112 without recombining with holes can be avoided.

Therefore, a large number of holes and electrons are present in a region in the vicinity of the interface between the first layer 121 and the second layer 122 of the light-emitting layer 113, so that the probability of recombination in the region in the vicinity of the interface can be increased. In other words, the light-emitting region is formed in the vicinity of the center of the light-emitting layer 113. As a result, the phenomenon in which holes reach the electron-transporting layer 114 without recombining with electrons or in which electrons reach the hole-transporting layer 112 without recombining with holes can be suppressed, whereby a reduction in the probability of recombination can be prevented. Thus, an reduction in carrier balance with time can be prevented, which leads to an increase in reliability.

It is preferred that the organic compound having a hole-transporting property is an organic compound capable of being oxidized and reduced and that the highest occupied molecular orbital level (HOMO level) thereof is equal to or greater than −6.0 eV and equal to or less than −5.0 eV in order to allow holes and electrons to be injected to the first layer 121 of the light-emitting layer 113. In addition, the lowest unoccupied molecular orbital level (LUMO level) of the organic compound having a hole-transporting property is preferably equal to or greater than −3.0 eV and equal to or less than −2.0 eV.

As such an organic compound that can be oxidized and reduced, use of anthracene derivatives is particularly preferable among tricyclic polyacene derivatives, tetracyclic polyacene derivatives, pentacyclic polyacene derivatives, and hexacyclic polyacene derivatives. Specific examples of the organic compound having an hole-transporting property, which is contained in the first layer 121 of the light-emitting layer 113, include 9,10-diphenylanthracene (abbreviated to DPAnth), N,N-diphenyl-9-[4-(10-phenyl-9-anthryl)phenyl]-9H-carbazol-3-amine (abbreviated to CzA1PA), 4-(10-phenyl-9-anthryl)triphenylamine (abbreviated to DPhPA), N,9-diphenyl-N-[4-(10-phenyl-9-anthryl)phenyl]-9H-carbazol-3-amine (abbreviated to PCAPA), N,9-diphenyl-N-{4-[4-(10-phenyl-9-anthryl)phenyl]phenyl}-9H-carbazol-3-amine (abbreviated to PCAPBA), and the like.

Similarly, it is preferred that the organic compound having an electron-transporting property is an organic compound capable of being oxidized and reduced and that the HOMO level thereof is equal to or greater than −6.0 eV and equal to or less than −5.0 eV in order to allow holes and electrons to be injected into the second layer 122 of the light-emitting layer 113. In addition, the lowest unoccupied molecular orbital level (LUMO level) of the organic compound having an electron-transporting property is preferably equal to or greater than −3.0 eV and equal to or less than −2.0 eV.

As such an organic compound which can be oxidized or reduced, a tricyclic polyacene derivative, a tetracyclic polyacene derivative, a pentacyclic polyacene derivative, or a hexacyclic polyacene derivative can be used. Specific examples include an anthracene derivative, a phenanthrene derivative, a pyrene derivative, a chrysene derivative, a dibenzo[g,p]chrysene derivative, and the like. For example, as a compound having an electron-transporting property, which can be used for the second layer 122 of the light-emitting layer 113, 9-[4-(10-phenyl-9-anthryl)phenyl]-9H-carbazole (abbreviated to CzPA), 3,6-diphenyl-9-[4-(10-phenyl-9-anthryl)phenyl]-9H-carbazole (abbreviated to DPCzPA), 9,10-bis(3,5-diphenylphenyl)anthracene (abbreviated to DPPA), 9,10-di(2-naphthyl)anthracene (abbreviated to DNA), 2-tert-butyl-9,10-di(2-naphthyl)anthracene (abbreviated to t-BuDNA), 9,9'-bianthryl (abbreviated to RANT), 9,9'-(stilbene-3,3'-diphenanthrene (abbreviated to DPNS), 9,9'-(stilbene-4,4'-diyl)diphenanthrene (abbreviated to DPNS2), 3,3',3"-(benzene-1,3,5-triyl)tripyrene (abbreviated to TPB3), and the like can be given.

As described above using FIG. 1B, the light-emitting element of the present embodiment is formed so that holes can be injected from the first layer 121 into the second layer 122 of the light-emitting layer 113. Therefore, it is preferable that the difference in HOMO level between the organic compound having a hole-transporting property and the organic compound having an electron-transporting property is small. The light-emitting element is also formed so that electrons can be injected from the second layer 122 into the first layer 121 of the light-emitting layer 113. Therefore, it is preferable that the difference in LUMO level between the organic compound having a hole-transporting property and the organic compound having an electron-transporting property is small. When the difference in HOMO level between the organic compound having a hole-transporting property and the organic compound having an electron-transporting property is large, the injection of holes from the first layer 121 into the second layer 122 is difficult, which results in a shift of the light-emitting region toward the first layer 121 side. In a similar way, when the difference in LUMO level between the organic compound having a hole-transporting property and the organic compound having an electron-transporting property is large, the injection of electrons from the second layer 122 to the first layer 121 is difficult, which results in a shift of the light-emitting region toward the second layer 122 side. Therefore, it is preferred that the difference in HOMO level between the organic compound having a hole-transporting property and the organic compound having an electron-transporting property and the difference in LUMO level between the organic compound having a hole-transporting property and the organic compound having an electron-transporting property are equal to or less than 0.3 eV, and more preferably, equal to or less than 0.1 eV.

Since light is emitted from the light-emitting element by recombination of electrons and holes, it is preferable that the organic compound used for the light-emitting layer 113 is stable with respect to repetitive oxidation and reduction. In other words, it is preferred that the organic compound can undergo reversible oxidation and reduction. In particular, the organic compound having a hole-transporting property and the organic compound having an electron-transporting property are preferably stable even if the oxidation and reduction thereof are repeated. Stability to repetitive oxidation and reduction can be confirmed by cyclic voltammetry (CV) measurement.

Specifically, changes in an oxidation peak potential ($E_{pa}$) in the oxidation or a reduction peak potential ($E_{pc}$) in the reduction of the organic compound, changes in a CV curve, and the like are observed, by which whether the organic compounds are stable to the repetitive oxidation and reduction can be confirmed. As to the organic compound having a hole-transporting property or an hole transporting property which is used in the light-emitting layer 113, it is preferred that changes in current at a peak potential of the oxidation and at a peak potential of the reduction are negligibly small even after the repetitive oxidation and reduction. In a similar way, it is preferred that the changes in peak potential in the oxidation and the peak potential in the reduction are negligibly small after the repetitive oxidation and reduction.

When the first organic compound contained in the first layer 121 and the second organic compound contained in the second layer 122 of the light-emitting layer 113 are different from each other, there is a possibility that light is emitted from only one of the first layer 121 and the second layer 122. However, if the light-emitting element is designed so that the first organic compound contained in the first layer 121 and the second organic compound contained in the second layer 122 are the same, light can be emitted in the vicinity of the center of the light-emitting layer 113. Therefore, it is preferred that the first organic compound contained in the first layer 121 and the second organic compound contained in the second layer 122 are the same substrate selected from the anthracene derivatives shown in Embodiment 1. Since the anthracene derivatives shown in Embodiment 1 have high emission efficiency, application thereof to the structure described in this embodiment leads to the formation of a light-emitting element with high emission efficiency and a long lifetime.

Moreover, since the anthracene derivatives shown in Embodiment 1 are bipolar and also possess a hole-transporting property, they can be used alone in the first layer 121 of the light-emitting layer 113 of the present embodiment. The second layer 122 has a structure in which any of the anthracene derivatives shown in Embodiment 1 is dispersed as an emission center in a host material, which means that the light-emitting element has a structure in which the first layer 121 comprises the material functioning as the emission center of the second layer 122. Thus, even if only the anthracene derivatives shown in Embodiment 1 are used in the first layer 121 of the light-emitting layer 113, emission from both the first layer 121 and the second layer 122 can be obtained because the first layer 121 of the light-emitting layer 113 has a hole-transporting property. Thus, light emission can be obtained from the first layer 121 which includes only the anthracene derivatives shown in Embodiment 1.

As mentioned above, the structure in which the anthracene derivative shown in Embodiment 1 is alone used in the first layer 121 of the light-emitting element improves an increase in emission efficiency. Additionally, this structure is able to realize a light-emitting element having both high emission efficiency and a long lifetime. One of the reasons for the improvement in emission efficiency is likely to be the contribution of electrons which fail to undergo recombination in the second layer 122 to light emission in the first layer 121. This structure also allows electrons which fail to undergo recombination in the second layer 122 to be recombined in the first layer 121, which contributes to a decrease in the number of electrons that reach the hole-transporting layer 112 and suppression of deterioration of the material included in the hole-transporting layer 112. This is recognized as one of the reasons for the improved lifetime. The improvement in emission efficiency and the prolongation of the lifetime are realized by the structure in which the first layer 121 comprises the anthracene derivative of Embodiment 1 which functions as a material of an emission center of the second layer 122.

In the light-emitting element shown in this embodiment, the light-emitting region is not located at the interface between the light-emitting layer 113 and the hole-transporting layer 112 or the interface between the light-emitting layer 113 and the electron-transporting layer 114, but formed in the vicinity of the center of the light-emitting layer 113. Therefore, there are almost no influences of deterioration which is caused when the light-emitting region is adjacent to the hole-transporting layer 112 or the electron-transporting layer 114. Therefore, a light-emitting element having a long lifetime and negligible deterioration can be obtained. Furthermore, since the light-emitting layer 113 in the light-emitting element of the present embodiment contains the compound that is stable in repetitive oxidation and reduction, it scarcely deteriorates even if light emission caused by recombination of holes and electrons is repeated. Therefore, a light-emitting element that has a long lifetime can be obtained.

Since in the light-emitting element shown in the present embodiment, the organic compound included in the first layer 121 and the organic compound included in the second layer 122 of the light-emitting layer 113 emit light of similar colors, light with high color purity can be obtained even if not only the organic compound included in the first layer 121 but also the organic compound included in the second layer 122 emits light. Further, since each of the anthracene derivatives shown in Embodiment 1 is a blue emissive substance having a high light-emitting property, the element structure described in this embodiment is particularly effective for use in a blue emissive light-emitting element and a blue-green emissive light-emitting element. Blue color is essential for fabrication of a full-color display, and the deterioration can be suppressed by applying the present invention. It is also possible to apply the present invention to a green emissive and a red emissive light-emitting element. This embodiment mode can be combined with any other embodiment as appropriate.

Moreover, as for the light-emitting element shown in the present embodiment, the first layer 121 and the second layer 122 of the light-emitting layer 113 may have a structure in which the anthracene derivative shown in Embodiment 1 is dispersed in a host material and also may have a structure in which the anthracene derivative shown in Embodiment 1 is not dispersed in a host material but is used solely.

Embodiment 6

In this embodiment, a mode of a light-emitting element with a structure in which a plurality of light-emitting units according to the present invention are stacked (hereinafter referred to as a stacked element) will be described with reference to FIG. 2. This light-emitting element is a light-emitting element having a plurality of light-emitting units between a first electrode and a second electrode. Each light-emitting unit can have a structure similar to that of the layer 102 containing an organic compound described in Embodiment 2. That is, the light-emitting element shown in Embodiment 2 is a light-emitting element having one light-emitting unit, whereas the light-emitting element described in this embodiment has a plurality of light-emitting units.

Figure 2:
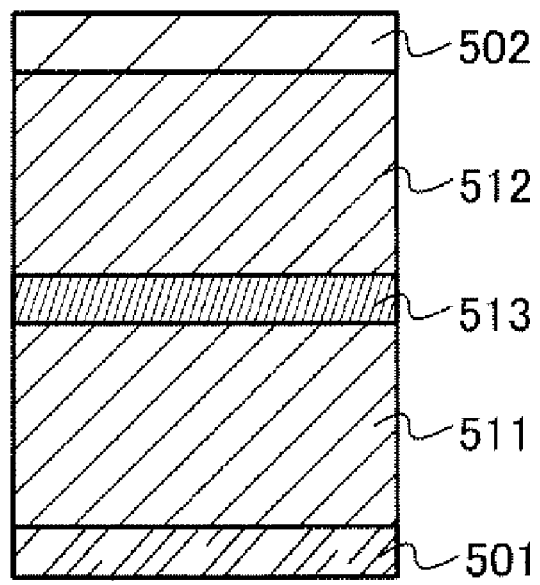
FIG. 2 is a diagram explaining a light-emitting element according to an embodiment of the present invention.

In FIG. 2, a first light-emitting unit 511 and a second light-emitting unit 512, which are laminated with a charge generation layer 513 interposed therebetween, are provided between a first electrode 501 and a second electrode 502. Materials similar to those in Embodiment 2 can be applied to the first electrode 501 and the second electrode 502. The first light-emitting unit 511 and the second light-emitting unit 512 may have the same structure or different structure, and the structure of the layer containing an organic compound shown in any of Embodiments 2 to 5 can be applied thereto.

A charge generation layer 513 includes a composite material of an organic compound and a metal oxide. This composite material of an organic compound and a metal oxide is that described in Embodiment 2 and contains an organic compound and a metal oxide such as vanadium oxide, molybdenum oxide, or tungsten oxide. As the organic compound, various compounds such as an aromatic amine compound, a carbazole derivative, an aromatic hydrocarbon, and a high molecular compound (an oligomer, a dendrimer, a polymer, or the like) can be used. An organic compound having a hole-transporting property, which has a hole mobility of greater than or equal to $1 \times 10^{-6}$ cm$^2$/Vs, is preferably applied as the organic compound. However, other materials may also be used as long as the hole-transporting property is higher than the electron-transporting property. The composite material of an organic compound and metal oxide is superior in carrier injection property and carrier-transporting property, and accordingly, low-voltage driving and low-current driving can be realized.

It is to be noted that the charge generation layer 513 may be formed with a combination of a composite material of an organic compound and a metal oxide, and other materials. For example, the charge generation layer 513 may be formed with a combination of a layer including the composite material of an organic compound and a metal oxide and a layer including one compound selected from electron-donating substances and a compound having a high electron-transporting property. Further, the charge generation layer 513 may be formed with a combination of a layer including the composite material of an organic compound and a metal oxide and a transparent conductive film.

In any case, the charge generation layer 513 sandwiched between the first light-emitting unit 511 and the second light-emitting unit 512 is acceptable as long as electrons are injected to one light-emitting unit and holes are injected to the other light-emitting unit when a voltage is applied between the first electrode 501 and the second electrode 502. For example, in FIG. 2, any layer can be employed as the charge generation layer 513 as long as the layer injects electrons into the first light-emitting unit 511 and holes into the second light-emitting unit 512 when voltage is applied so that the potential of the first electrode 501 is higher than that of the second electrode 502.

In this embodiment, a light-emitting element having two light-emitting units is explained; however, the present embodiment can be similarly applied to a light-emitting element in which three or more light-emitting units are stacked. When the charge generation layer is provided between the pair of electrodes so as to partition the plural light-emitting units like the light-emitting element of this embodiment, it is possible to provide a light-emitting element which has a long lifetime and is able to emit light at a high luminance at a low current density. Moreover, a light-emitting device with low power consumption, which can be driven at low voltage, can be obtained.

If the light-emitting units are allowed to emit light having different colors from each other, light emission of a desired color can be obtained from the whole light-emitting element. For example, in the case of a light-emitting element having two light-emitting units, if the emission colors of the first light-emitting unit and the second light-emitting unit are made complementary to each other, white light can be obtained from whole of the light-emitting element. Note that "complementary color" means a relation between colors which becomes an achromatic color when they are mixed. That is, white light emission can be obtained by mixing light from substances whose emission colors are complementary colors. This technique can be similarly applied to a light-emitting element having three light-emitting units. For example, white light emission can be obtained from a light-emitting element when emission colors of the first, second, and third light-emitting units are red, green, and blue, respectively.

Note that this embodiment can be appropriately combined with other embodiments.

Embodiment 7

Figure 3A:
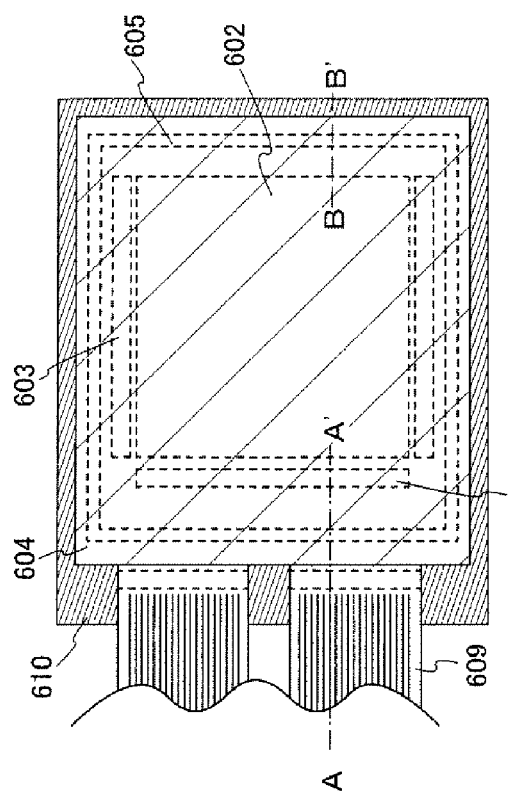
FIGS. 3A and 3B are diagrams explaining a light-emitting device according to an embodiment of the present invention.
Figure 3B:
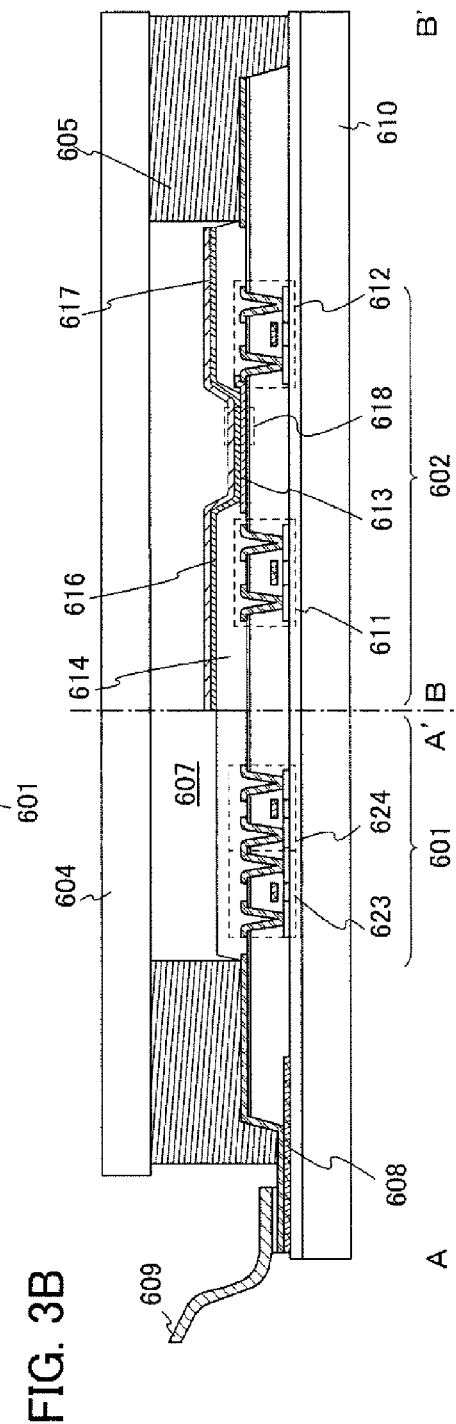

In this embodiment mode, a light-emitting device manufactured using the anthracene derivative shown in Embodiment 1 will be described.

in this embodiment mode, a light-emitting device manufactured using the anthracene derivative shown in Embodiment 1 will be described with reference to FIGS. 3A and 3B. FIG. 3A is a top view of the light-emitting device, and FIG. 3B is a cross sectional view taken along lines A-A' and B-B' of FIG. 3A. This light-emitting device includes a driver circuit portion (source side driver circuit) 601 and a driver circuit portion (gate side driver circuit) 603 which are configured to control the light emission of the light-emitting element located in a pixel portion 602. A reference numeral 604 represents a sealing substrate, a reference numeral 605 represents a sealant, and the inside surrounded by the sealant 605 is a space 607.

A lead wiring 608 is a wiring for transmitting signals to be inputted to the source side driver circuit 601 and the gate side driver circuit 603 and receives a video signal, a clock signal, a start signal, a reset signal, and the like from a flexible printed circuit (FPC) 609 which is an external input terminal. Although only the FPC is shown here, the FPC may be provided with a printed wiring board (PWB). The light-emitting device described in the specification includes not only a light-emitting device itself but also a state in which an FPC or a PWB is attached thereto.

Next, a sectional structure will be described with reference to FIG. 3B. Although the driver circuit portion and the pixel portion are formed over an element substrate 610, the source side driver circuit 601, which is one of the driver circuit portions, and one pixel in the pixel portion 602 are illustrated here.

Note that as the source side driving circuit 601, a CMOS circuit in which an n-channel TFT 623 and a p-channel TFT 624 are combined is formed. The driver circuit may be formed by various CMOS circuits, PMOS circuits, or NMOS circuits. In this embodiment, although a driver-integrated type structure in which a driver circuit is formed over an element substrate 610 is described, a driver circuit is not necessarily formed over the element substrate 610 but can be formed externally from the element substrate 610.

The pixel portion 602 has a plurality of pixels, each of which includes a switching TFT 611, a current control TFT 612, and a first electrode 613 which is electrically connected to a drain of the current control TFT 612. An insulator 614 is formed to cover the edge of the first electrode 613. Here, the insulator 614 is formed using a positive photosensitive acrylic resin.

In order to favorably cover the edge of the first electrode 613, the insulator 614 is provided such that either an upper edge portion or a lower edge portion thereof has a curved surface with a curvature. For example, in the case of using a positive photosensitive acrylic as a material of the insulator 614, it is preferred that only the upper end portion of the insulator 614 has a curved surface with curvature (a radius of curvature of 0.2 to 3 μm). Note that the insulator 614 can be formed using either a negative photoresist resist that becomes insoluble in an etchant after photo-irradiation or a positive photoresist that becomes insoluble in an etchant after photo-irradiation.

A layer containing an organic compound (EL layer) 616 and a second electrode 617 are formed over the first electrode 613. Here, a material having a high work function is preferably used as a material used for the first electrode 613 which serves as an anode. For example, in addition to a single-layer film such as an ITO film, an indium tin oxide film containing silicon, an indium oxide film containing 2 wt % to 20 wt % of zinc oxide, a titanium nitride film, a chromium film, a tungsten film, a Zn film, a Pt film, or the like, a stacked film such as a stack of a titanium nitride film and a film containing aluminum as its main component or a stacked film having a three-layer structure of a titanium nitride film, a film containing aluminum as its main component, and another titanium nitride film can be used. With a stacked layer structure, the resistance as a wire is low, a good ohmic contact can be obtained, and further a function as an anode can be obtained.

The EL layer 616 is formed by various methods such as an evaporation method using an evaporation mask, an ink-jet method, a spin coating method, or the like. The EL layer 616 includes the anthracene derivative shown in Embodiment 1. As another material included in the EL layer 616, a low molecular compound or a high molecular compound (including an oligomer or a dendrimer) may be used. Further, not only organic compounds but also inorganic compounds can be used for the material for forming the EL layer 616.

Further, as a material used for the second electrode 617 which is formed over the EL layer 616 and functions as a cathode, it is preferable to use a material with a low work function (e.g., Al, Mg, Li, Ca, or an alloy or a compound thereof such as MgAg, MgIn, AlLi, LiF, or $CaF_2$). When light generated in the EL layer 616 passes through the second electrode 617, the second electrode 617 is preferably formed by a stack of a thin metal film and a transparent conductive film (ITO, indium oxide including 2 wt % to 20 wt % of zinc oxide, indium tin oxide including silicon or silicon oxide, zinc oxide, or the like).

The sealing substrate 604 is attached to the element substrate 610 with the sealant 605, whereby a light-emitting element 618 is provided in the space 607 surrounded by the element substrate 610, the sealing substrate 604, and the sealant 605. Note that the space 607 is filled with a filler and may be filled with the sealant 605 in addition to an inert gas (nitrogen, argon, and the like).

As a material for the sealant 605, an epoxy resin is preferably used. It is desirable to use a material that allows permeation of moisture or oxygen as little as possible. As the sealing substrate 604, a plastic substrate formed of FRP (fiberglass-reinforced plastics), PVF (poly(vinyl fluoride)), a polyester, an acrylic, or the like can be used besides a glass substrate or a quartz substrate.

In this manner, the light-emitting device manufactured using the anthracene derivative shown in Embodiment 1 can be obtained.

Since the anthracene derivative shown in Embodiment 1 is used for the light-emitting device of the present embodiment, the light-emitting device with favorable characteristics can be obtained. Specifically, a light-emitting device having a long lifetime can be obtained.

Also, since the anthracene derivatives shown in Embodiment 1 have high emission efficiency, a light-emitting device with low power consumption can be provided.

Further, since the light-emitting element in which any of the anthracene derivatives shown in Embodiment 1 is used can emit blue light with high color purity at high efficiency, the light-emitting element are suitable for use in full-color displays. Further, since the light-emitting element can emit blue light and has a long lifetime, the light-emitting element is suitable for use in full-color displays.

Figure 4A:
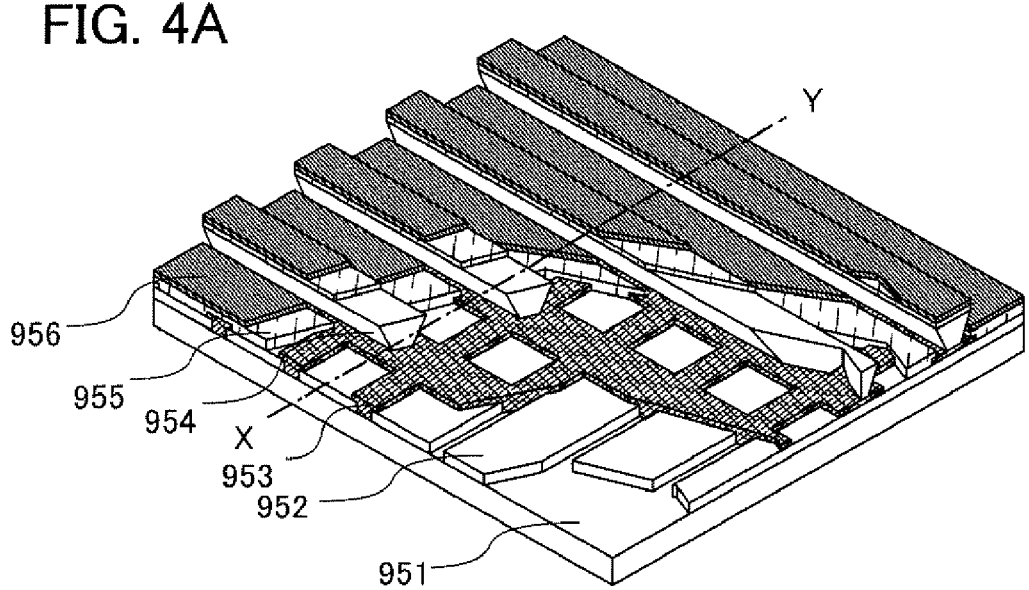
FIGS. 4A and 4B are diagrams explaining a light-emitting device according to an embodiment of the present invention.
Figure 4B:
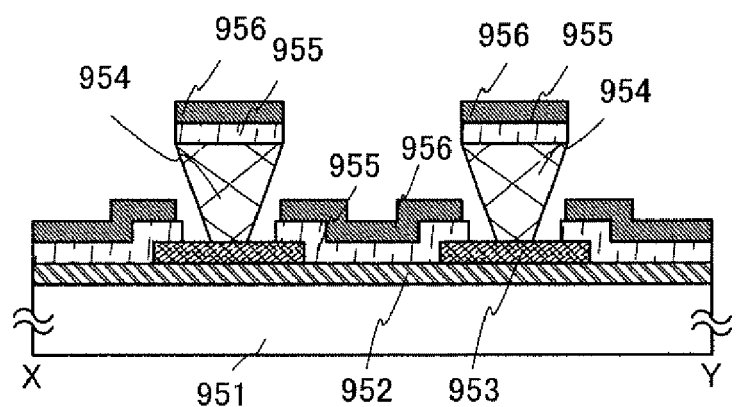

As described above, in this embodiment, an active matrix type light-emitting device in which operation of a light-emitting element is controlled by a transistor is described. Alternatively, a passive matrix type light-emitting device may also be used. FIGS. 4A and 4B illustrate a passive matrix type light-emitting device manufactured by applying the present invention. FIG. 4A is a perspective view of the light-emitting device, and FIG. 4B is a cross-sectional view taken along line X-Y in FIG. 4A. As shown in FIGS. 4A and 4B, an electrode 952 and an electrode 956 are provided over a substrate 951, and a layer (EL layer) 955 containing an organic compound is provided between the electrode 952 and the electrode 956. The edge of the electrode 952 is covered with an insulating layer 953. A partition wall layer 954 is provided on the insulating layer 953. The sidewalls of the partition wall layer 954 are aslope so that a distance between both sidewalls is gradually narrowed toward the surface of the substrate 951. That is, a cross section in the direction of a narrow side of the partition wall layer 954 has a trapezoidal shape, and a lower side (which faces a surface of the insulating layer 953 and is in contact with the insulating layer 953) is shorter than an upper side (which faces the surface of the insulating layer 953 and is not in contact with the insulating layer 953). By providing the partition wall layer 954 in this manner, defects of the light-emitting element due to a cross talk and the like can be prevented. By using any of the anthracene derivatives shown in Embodiment 1, a passive matrix type light-emitting device having a long lifetime can be obtained. Further, a light-emitting device with low power consumption can be manufactured.

Embodiment 8

In this embodiment, an electronic device according to the present invention which includes the light-emitting device described in Embodiment 7 in part thereof will be explained. The electronic device shown in this embodiment includes the anthracene derivative described in Embodiment 1, and has a display portion with a long lifetime. Further, it has a display portion which low power consumption.

Examples of electronic devices each manufactured using the anthracene derivative shown in Embodiment 1 include video cameras, digital cameras, goggle type displays, navigation systems, audio playback devices (e.g., car audio systems and other audio systems), computers, game machines, portable information terminals (e.g., mobile computers, mobile phones, portable game machines, and electronic books), image playback devices provided with recording media (i.e., devices that are capable of playing back recording media such as digital versatile discs (DVDs) and equipped with display devices that can display the image), and the like. Specific examples for such electronic devices are shown in FIGS. 5A to 5D.

Figure 5A:
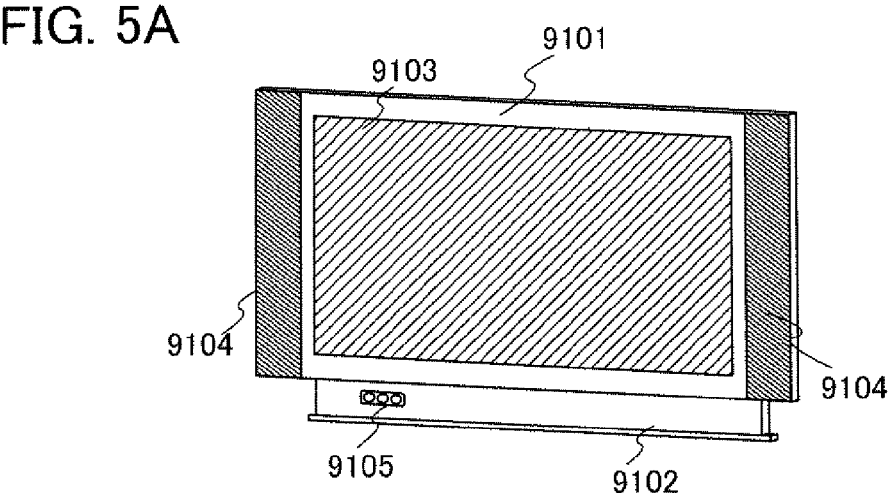
FIGS. 5A to 5D are diagrams explaining an electronic device according to an embodiment of the present invention.

FIG. 5A shows a television set of the present invention, which includes a housing 9101, a supporting base 9102, a display portion 9103, speaker portions 9104, a video input terminal 9105, and the like. In the display portion 9103 of this television set, light-emitting elements similar to those described in any of Embodiments 2 to 6 are arranged in matrix. The features of the light-emitting element are exemplified by high emission efficiency and a long lifetime. The display portion 9103 which includes the light-emitting elements has a similar feature. Therefore, in the television device, image quality is hardly deteriorated and low power consumption is attained. With such a feature, a deterioration compensation functional circuit and a power supply circuit can be significantly reduced or downsized in the television set; therefore, the housing 9101 and the supporting base 9102 can be lightened and downsized. Since the television set in accordance with the present invention can realize low power consumption, high image quality and reduction in size and weight, products suitable for any residential environment can be provided. Also, since a light-emitting element utilizing any of the anthracene derivatives described in Embodiment 1 can emit blue light with high color purity, a television set that can display full-color image and possesses a display portion with a long lifetime can be obtained.

Figure 5B:
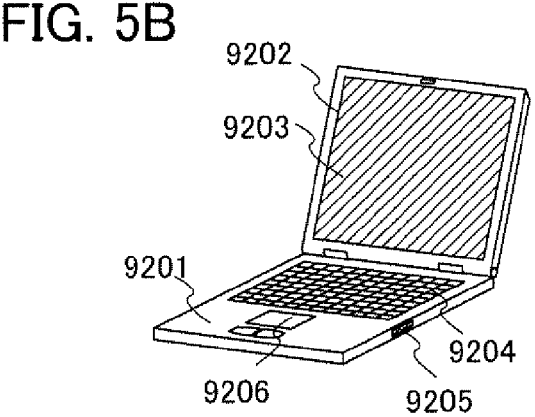

FIG. 5B shows a computer in accordance with the invention, which includes a main body 9201, a housing 9202, a display portion 9203, a keyboard 9204, an external connection port 9205, a pointing device 9206, and the like. In the display portion 9203 of this computer, light-emitting elements similar to those described in any of Embodiments 2 to 6 are arranged in matrix. The features of the light-emitting element are exemplified by high emission efficiency and a long lifetime. The display portion 9203 which includes the light-emitting elements has a similar feature. Therefore, in the computer, image quality is hardly deteriorated and low power consumption is attained. With such a feature, a deterioration compensation functional circuit and a power supply circuit can be significantly reduced or downsized in the computer; therefore, the main body 9201 and the housing 9202 can be lightened and downsized. Since the computer in accordance with the present invention can realize low power consumption, high image quality and reduction in size and weight, products suitable for any residential environment can be provided. Also, since a light-emitting element utilizing any of the anthracene derivatives described in Embodiment 1 can emit blue light with high color purity, a computer that can display full-color image and possesses a display portion with a long lifetime can be obtained.

Figure 5C:
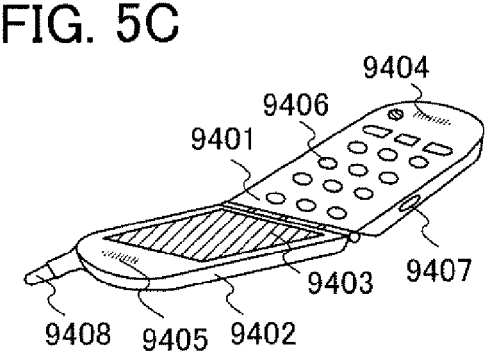

FIG. 5C shows a portable phone of the present invention, which includes a main body 9401, a housing 9402, a display portion 9403, an audio input portion 9404, an audio output portion 9405, an operation key 9406, an external connecting port 9407, an antenna 9408, and the like. In the display portion 9403 of this mobile phone, light-emitting elements similar to those described in any of Embodiments 2 to 6 are arranged in matrix. The features of the light-emitting element are exemplified by high emission efficiency and a long lifetime. The display portion 9403 which includes the light-emitting elements has a similar feature. Therefore, in the mobile phone, image quality is hardly deteriorated and low power consumption is attained. With such a feature, a deterioration compensation functional circuit and a power supply circuit can be significantly reduced or downsized in the mobile phone; therefore, the main body 9401 and the housing 9402 can be lightened and downsized. Since the mobile phone in accordance with the present invention can realize low power consumption, high image quality and reduction in size and weight, products suitable for any residential environment can be provided. Also, since a light-emitting element utilizing any of the anthracene derivatives described in Embodiment 1 can emit blue light with high color purity, a mobile phone that can display full-color image and possesses a display portion with a long lifetime can be obtained.

Figure 5D:
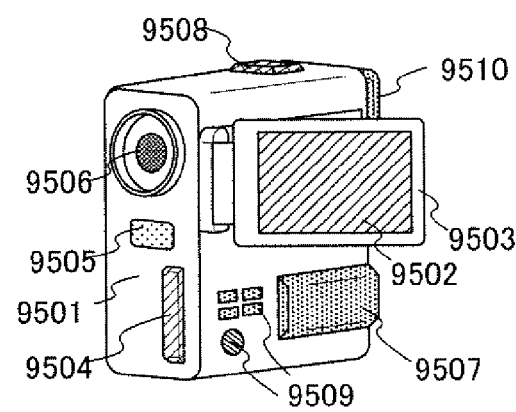

FIG. 5D shows a camera of the present invention, which includes a main body 9501, a display portion 9502, a housing 9503, an external connecting port 9504, a remote controller receiving portion 9505, an image receiving portion 9506, a battery 9507, an audio input portion 9508, operation keys 9509, an eye piece portion 9510, and the like. In the display portion 9502 of this camera, light-emitting elements similar to those described in any of Embodiments 2 to 6 are arranged in matrix. The features of the light-emitting element are exemplified by high emission efficiency and a long lifetime. The display portion 9502 which includes the light-emitting elements has a similar feature. Therefore, in the camera, image quality is hardly deteriorated and low power consumption is attained. With such a feature, a deterioration compensation functional circuit and a power supply circuit can be significantly reduced or downsized in the camera; therefore, the main body 9501 can be lightened and downsized. Since the camera in accordance with the present invention can realize low power consumption, high image quality and reduction in size and weight, products suitable for any residential environment can be provided. Also, since a light-emitting element utilizing any of the anthracene derivatives described in Embodiment 1 can emit blue light with high color purity, a camera that can display full-color image and possesses a display portion with a long lifetime can be obtained.

As described above, the range of application of a light-emitting device manufactured applying the invention is extremely wide, and the light-emitting device can be applied to electronic devices in all kinds of fields. By using the anthracene derivative shown in Embodiment 1, electronic devices which have display portions with a long lifetime can be provided. Furthermore, by use of the anthracene derivatives shown in Embodiment 1, an electronic device that has a display portion with low power consumption can be obtained.

In addition, the light-emitting device to which the present invention is applied can also be used as a lighting device. One mode using the light-emitting element to which the present invention is applied as the lighting device will be explained with reference to FIG. 6.

Figure 6:
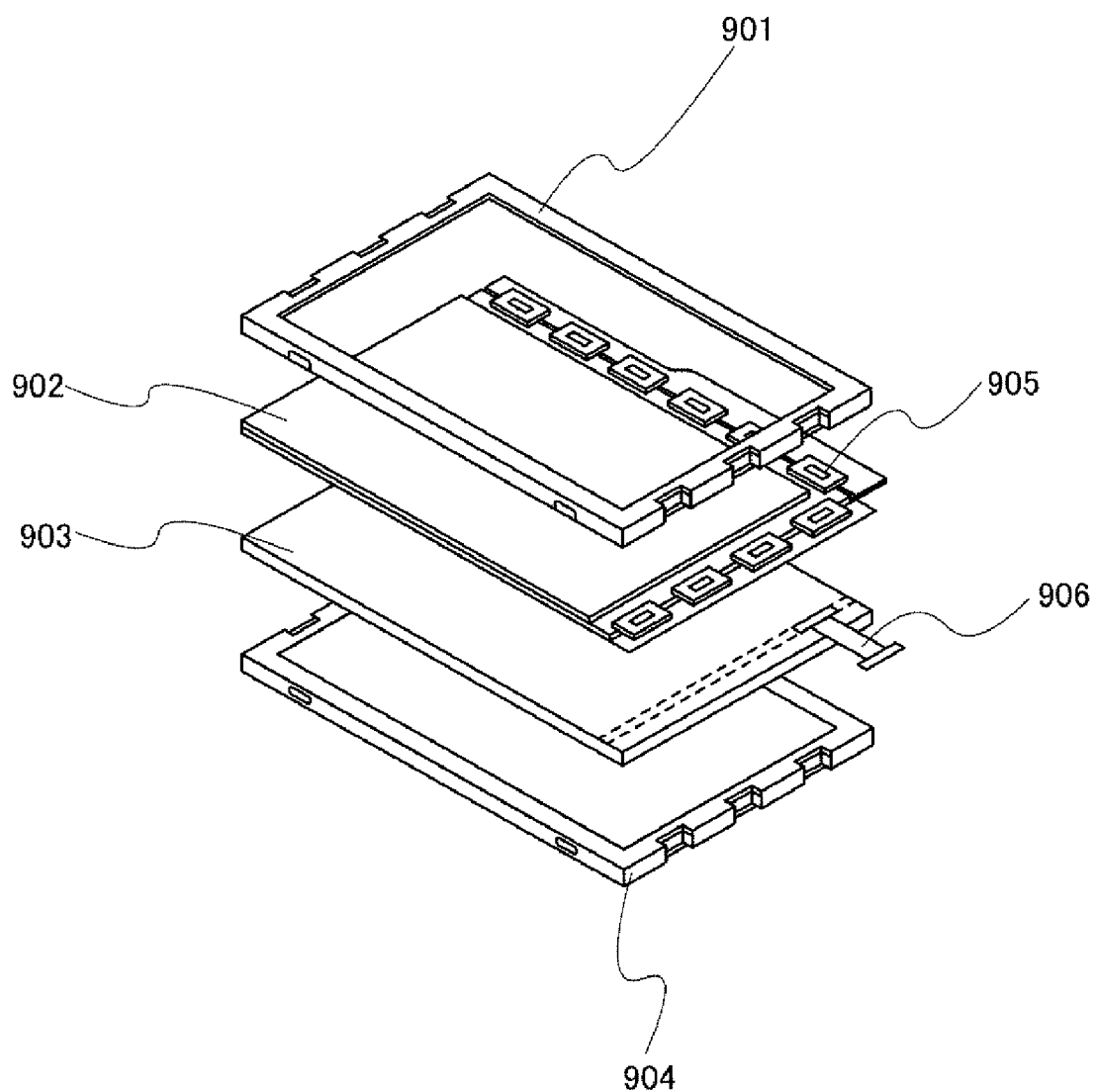
FIG. 6 is a diagram explaining a lighting device according to an embodiment of the present invention.

FIG. 6 shows an example of a liquid crystal display device using the light-emitting device to which the present invention is applied as a backlight. The liquid crystal display device shown in FIG. 6 includes a housing 901, a liquid crystal layer 902, a backlight 903 and a housing 904, and the liquid crystal layer 902 is connected to a driver IC 905. The light-emitting device to which the present invention is applied is used as the backlight 903, and current is supplied through a terminal 906.

By using the light-emitting device to which the present invention is applied as the backlight of the liquid crystal display device, a backlight with reduced power consumption and high emission efficiency can be obtained. The light-emitting device to which the present invention is applied is a lighting device with plane emission, and can have a large area. Therefore, it is readily increase the area of the backlight, which contributes to the increase in the area of the liquid crystal display device. Furthermore, the light-emitting device has a thin shape and exhibits low power consumption; therefore, a display device with low power consumption can be formed in a thin shape. Since the light-emitting device to which the present invention is applied has a long lifetime, a liquid crystal display device using the light-emitting device to which the present invention is applied also has a long lifetime.

Figure 7:
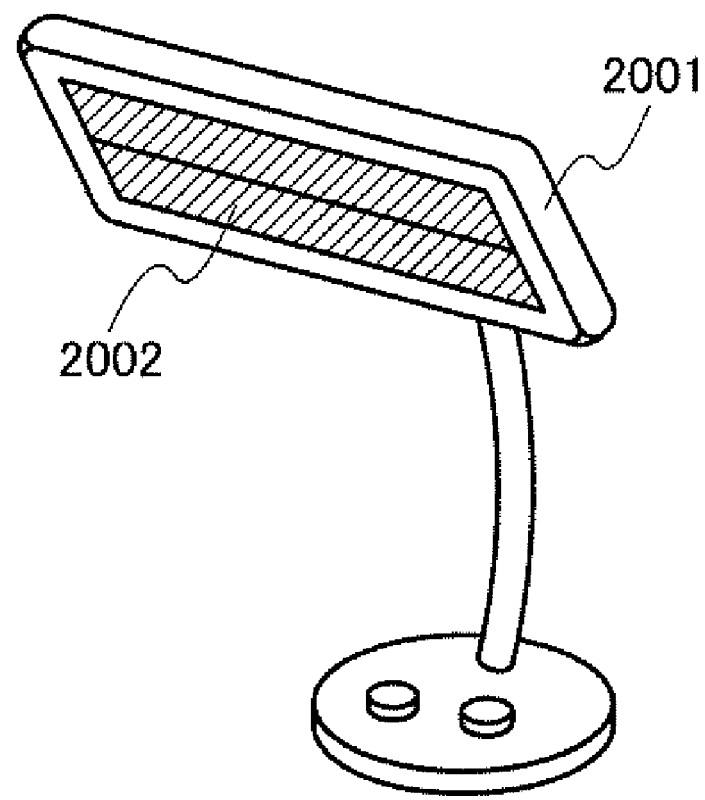
FIG. 7 is a diagram explaining a lighting device according to an embodiment of the present invention.

FIG. 7 shows an example in which the light-emitting device to which the present invention is applied is used as a desk lamp which is a lighting device. The desk lamp shown in FIG. 7 includes a housing 2001 and a light source 2002. The light-emitting device to which the present invention is applied is used as the light source 2002. The light-emitting device to which the present invention is applied has high emission efficiency and has a long lifetime; therefore, a table lamp also has high emission efficiency and a long lifetime.

Figure 8:
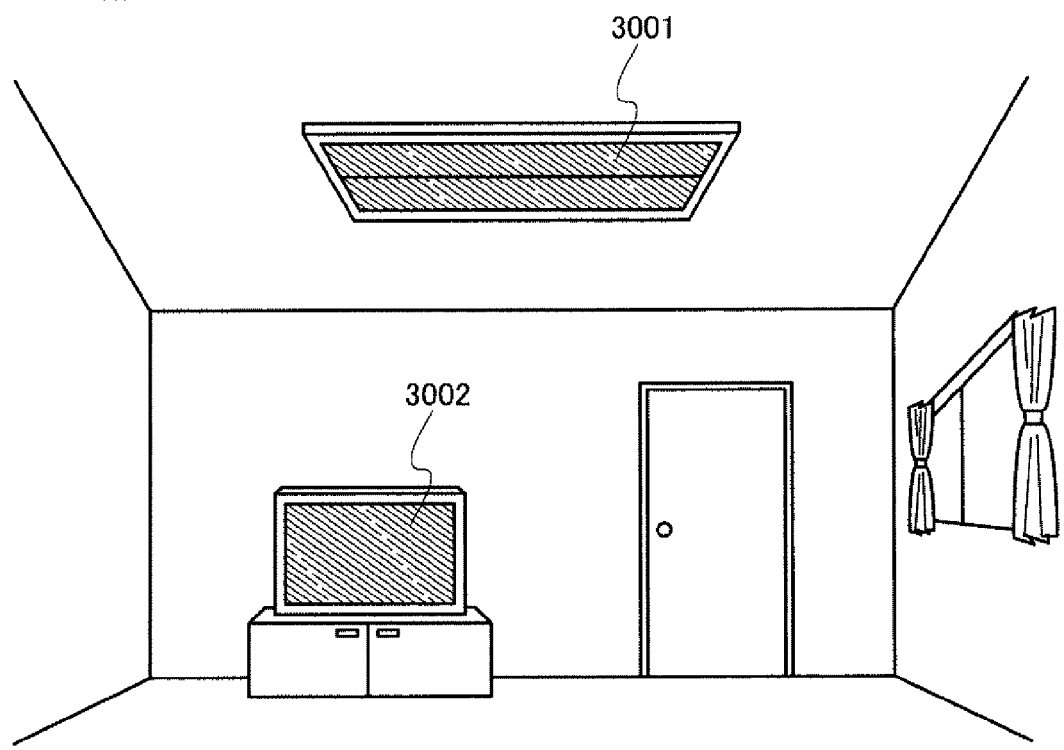
FIG. 8 is a diagram explaining a lighting device according to an embodiment of the present invention.

FIG. 8 shows an example in which the light-emitting device to which the present invention is applied is used for an indoor lighting device 3001. Since the light-emitting device to which the present invention is applied can also have a large area, it can be used as a lighting device having a large area. Further, the light-emitting device to which the present invention is applied has a thin shape and exhibits low power consumption; accordingly, is can be used as a lighting device having a thin shape and low power consumption. Thus, a television set 3002 according to the present invention similar to the television set described with reference to FIG. 5A can be installed in the room using the light-emitting device according to the present invention as the indoor lighting device 3001, so that pubic broadcasting and movies can be enjoyed. In such a case, since both of the devices consume low power, a powerful image can be watched in a bright room without concern about electricity charges.

EXAMPLE 1

In this example, specific explanation is given for the synthetic methods of 4-(1-naphthyl)-4'-(10-phenyl-9-anthryl)-4"-(9-phenyl-9H-carbazol-3-yl)triphenylamine (abbreviated to PCBNAPA), which is an anthracene derivative according to an embodiment of the present invention and is represented by the structural formula (101), and 4-(1-naphthyl)-4'-(9-phenyl-9H-carbazol-3-yl)diphenylamine (abbreviated to PCBNA) which is used in the synthesis of PCBNAPA and is represented by the structural formula (301).

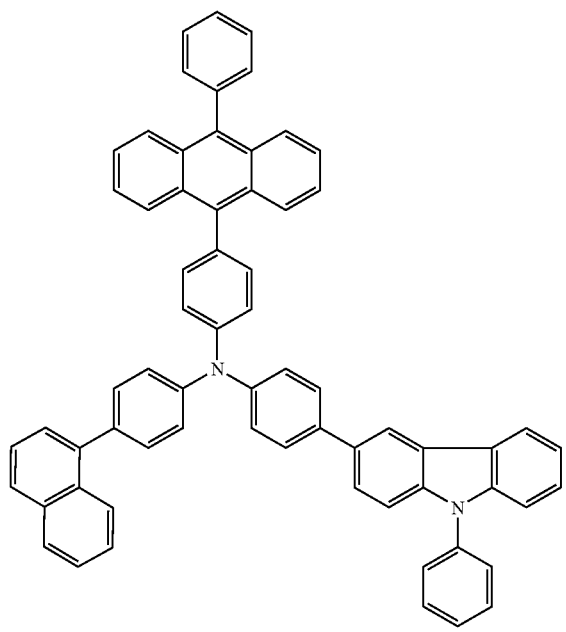

(101)

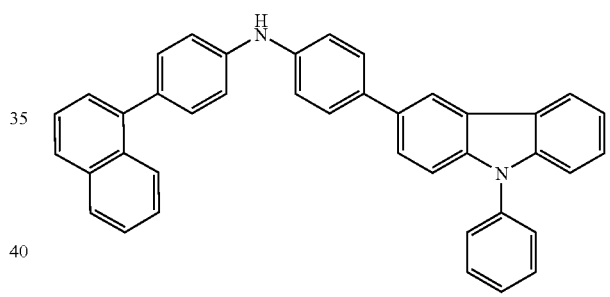

(301)

[Step 1: Synthesis of 9-phenylanthracene]

To a 200 mL three-neck flask were added 6.4 g (25 mmol) of 9-bromoanthracene, 3.0 g (25 mmol) of phenylboronic acid, 0.76 g (2.5 mmol) of tri(o-tolyl)phosphine, 60 mL of 1,2-dimethoxyethane (DME), and 25 mL of a 2.0 M aqueous solution of potassium carbonate. The mixture was degassed under reduced pressure with stirring, and the air in the flask was replaced with nitrogen. To the mixture was added 0.11 g (0.50 mmol) of palladium(II) acetate, and the mixture was stirred under nitrogen at 80° C. for 3 hours. After a predetermined period, water was added to the mixture, and the aqueous layer and the organic layer were separated from each other. The aqueous layer was extracted with toluene. The extract and the organic layer were combined, washed with brine, and dried with magnesium sulfate. The mixture was subjected to suction filtration through Celite (produced by Wako Pure Chemical Industries, Ltd., Catalog No. 531-16855), Florisil (produced by Wako Pure Chemical Industries, Ltd., Catalog No. 540-00135), and alumina, and the filtrate was concentrated to give a solid. The solid was recrystallized with a mixed solvent of toluene and methanol to give 5.8 g of a white powder which was a target substance in a yield of 92%. The synthetic scheme of 9-phenylanthracene is shown below in (A-1).

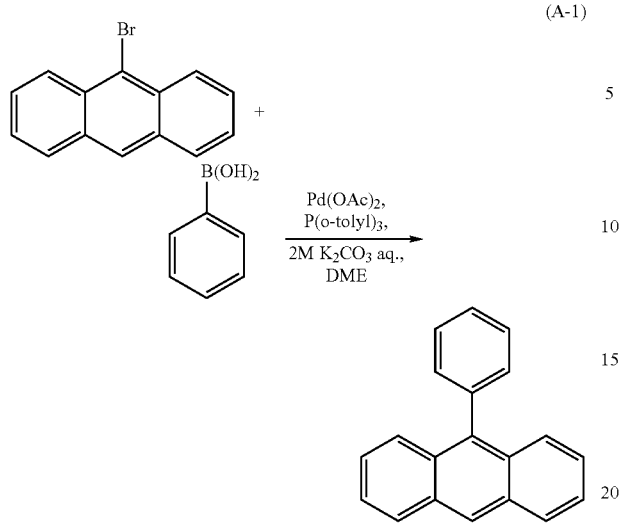

(A-1)

[Step 2: Synthesis of 9-iodo-10-phenylanthracene]

To a 500 mL, Erlenmeyer flask was added 4.5 g (18 mmol) of 9-phenylanthracene. To the flask was added 200 mL of acetic acid, followed by heating at 70° C. to dissolve 9-phenylanthracene therein. To the resulting solution was added 5.2 g (13 mmol) of 1,3-diiodo-5,5-dimethylimidazolidine-2,4-dione (DIH), and the solution was stirred under air at 70° C. for 3 hours. After the reaction, ca. 100 mL of water and ca. 200 mL of chloroform were added to this solution. The resulting mixture was washed with water twice, and the organic layer was separated from the aqueous layer. The aqueous layer was extracted with chloroform. The extract was combined with the organic layer and washed with brine, and then the combined organic layer was dried with magnesium sulfate. This mixture was gravity filtered, and the obtained filtrate was concentrated to give a brown solid. This solid was washed with hexane to give 5.8 g of a yellow solid which was a target substance in a yield of 86%. The synthetic scheme is shown in (A-2).

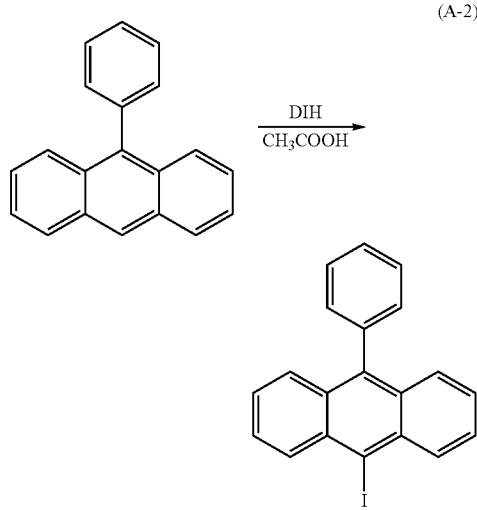

(A-2)

[Step 3: Synthesis of 9-(4-bromophenyl)-10-phenylantracene]

A mixture containing 1.0 g (2.6 mmol) of 9-iodine-10-phenylanthracene, 540 mg (2.7 mmol) of p-bromophenylboronic acid, 46 mg (30 μmol) of tetrakis(triphenylphosphine) palladium(0) (Pd(PPh$_3$)$_4$), 3.0 mL of an aqueous solution of potassium carbonate (2.0 mol/L), and 10 mL of toluene was stirred at 80° C. for 9 hours. After the reaction, toluene was added to the mixture, and the mixture was filtered through Florisil (produced by Wako Pure Chemical Industries, Ltd., Catalog No. 540-00135), Celite (produced by Wako Pure Chemical Industries, Ltd., Catalog No. 531-16855), and alumina. The obtained filtrate was washed with water and brine, followed by drying with magnesium sulfate. This mixture was gravity filtered, and the obtained filtrate was concentrated to give a solid, which was subjected to recrystallization with a mixed solvent of chloroform and hexane, resulting in 560 mg of a pale yellow solid which szx a target substance in 45% yield. The synthetic scheme of 9-(4-bromophenyl)-10-phenylanthracene is illustrated in (A-3).

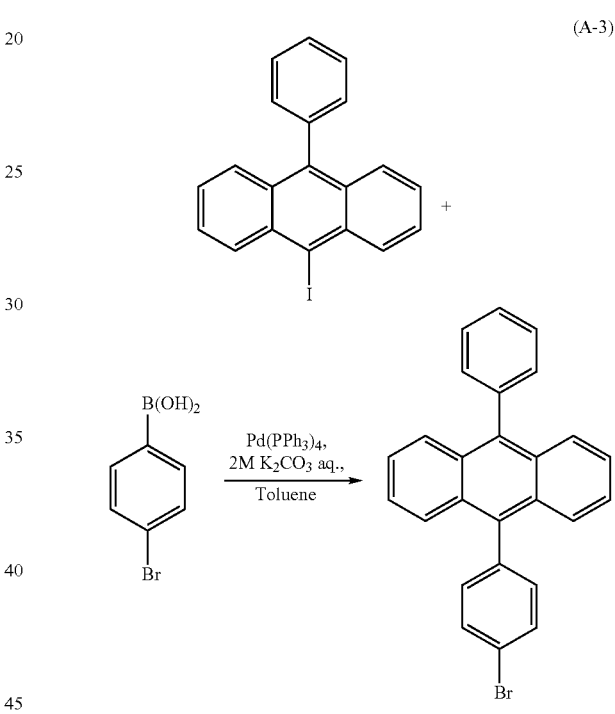

(A-3)

[Step 4: Synthesis of 3-(4-bromophenyl)-9-phenyl-9H-carbazole]

To a 200-mL three-neck flask were added 3.7 g (9.9 mmol) of 3-iodo-9-phenyl-9H-carbazole, 2.0 g (9.9 mmol) of 4-bromophenylboronic acid, and 0.61 g (2.0 mmol) of tri(o-tolyl) phosphine, which was followed by addition of 50 mL of 1,2-dimethoxyethane (abbreviated to DME) and 10 mL of an aqueous solution of potassium carbonate (2.0 mol/L). This mixture was degassed while being stirred under reduced pressure, and the atmosphere in the flask was substituted with nitrogen. Then, 0.11 g (0.50 mmol) of palladium(II) acetate was added to this mixture, which was then stirred at 80° C. for 9.5 hours. After the reaction, this mixture was cooled to room temperature and then washed twice with water. The organic layer was separated from the aqueous layer, and the resulting aqueous layer was extracted twice with toluene. Then, the extract was combined with the organic layer, followed by washing with brine. The combined organic layer was dried with magnesium sulfate, and subjected to the gravity filtration, and then the filtrate was concentrated. The resulting oily product was dissolved in ca. 20 mL of toluene, and the solution was subjected to suction filtration through Celite (produced by Wako Pure Chemical Industries, Ltd., Catalog No. 531-16855), alumina, and Florisil (produced by Wako Pure Chemical Industries, Ltd., Catalog No. 540-00135). A solid which was obtained by concentrating the obtained filtrate was purified by silica gel column chromatography (developing solvent, toluene:hexane=1:4) to obtain 1.9 g of a white powder which was a target substance in a yield of 49%. A synthetic scheme of 3-(4-bromophenyl)-9-phenyl-9H-carbazole is shown in the following reaction scheme (A-4).

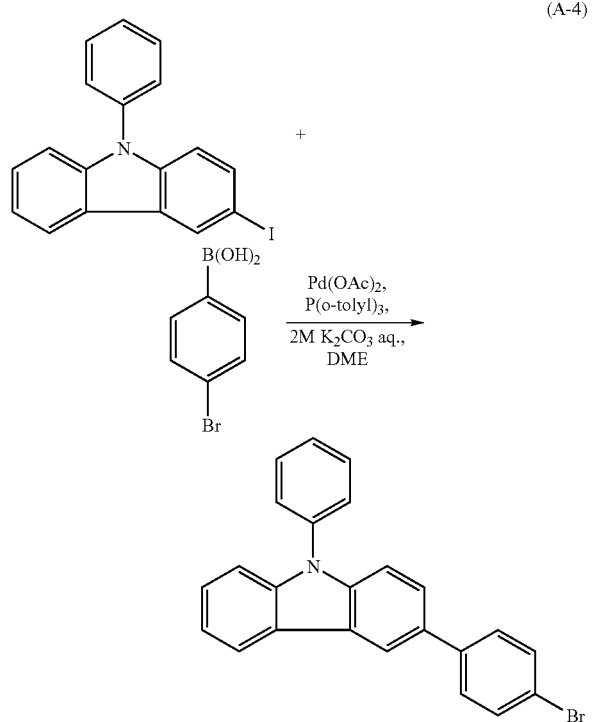

Alternatively, 3-(4-bromophenyl)-9-phenyl-9H-carbazole can be synthesized in the method shown below. The following method is preferred since a less amount of by-product is formed and purification is readily accomplished.

To a 100 mL three-neck flask were added 1.3 g (4.5 mmol) of 9-phenyl-9H-carbazol-3-yl-boronic acid, 1.3 g (4.6 mmol) of 1-bromo-4-iodobenzene, and 72.6 mg (0.2 mmol) of tris (2-methylphenyl)phosphine, and the air in the flask was substituted with nitrogen. To the mixture were added 17.0 mL of toluene, 5.7 mL of ethanol, and 4.6 mL of an aqueous solution of potassium carbonate (2 mol/L), and the mixture was degassed with stirring under reduced pressure. After degassing, the mixture was heated at 60° C., and 32.4 mg (0.1 mmol) of palladium(II) acetate was added. The mixture was stirred at 80° C. for 3.5 hours. After the reaction, toluene and water were added to the mixture, the organic layer is separated from the aqueous layer, and the aqueous layer was extracted three times with toluene. The extract and the organic layer were combined, washed with brine, and dried with magnesium sulfate. The resulting mixture was gravity filtered to remove magnesium sulfate, and the filtrate was concentrated to give an oily product, which was subjected to recrystallization with toluene/hexane to give 1.15 g of a solid which was a target substance in 64% yield. This synthetic scheme of 3-(4-bromophenyl)-9-phenyl-9H-carbazole is shown in the following reaction scheme (A-4-2).

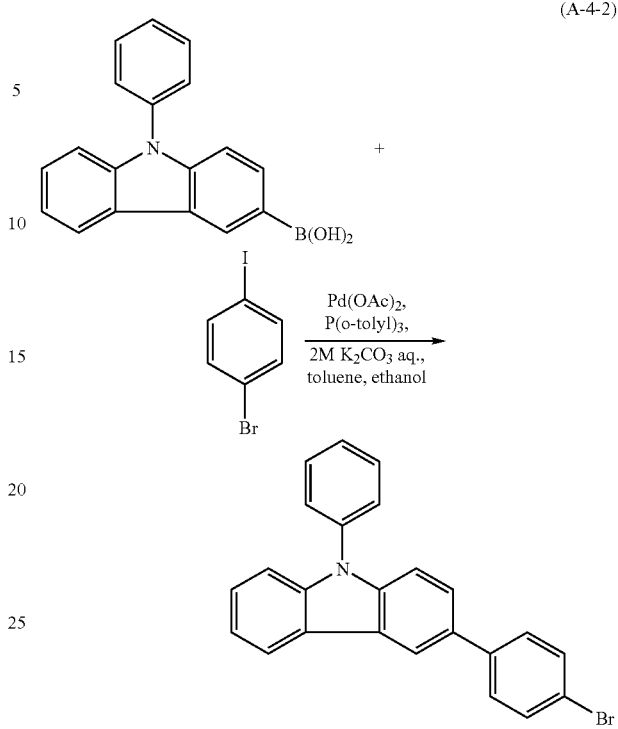

[Step 5: Synthesis of 4-(1-naphthyl)aniline]

Into a 500-mL three-neck flask were put 5.0 g (29 mmol) of 4-Bromoaniline, 5.0 g (29 mmol) of 1-naphthylboronic acid, and 0.45 g (1.5 mmol) of tri(o-tolyl)phosphine, and nitrogen substitution in the flask was carried out. To this mixture were added 100 mL of toluene, 50 mL of ethanol, and 31 mL of an aqueous solution of potassium carbonate (2 mol/L). The mixture was stirred and degassed under reduced pressure. Then, after the mixture was heated at 60° C., 66.2 mg (0.29 mmol) of palladium(II) acetate was added into the mixture. The mixture was refluxed at 80° C. for 2.3 hours. After the reaction, toluene and water were added to the mixture, the organic layer was separated from the aqueous layer, and the aqueous layer was extracted twice with toluene. The extract and the organic layer were combined, washed with brine, and dried with magnesium sulfate. The mixture was gravity filtered to remove magnesium sulfate, and the filtrate was concentrated to give an oily product, which was subjected to suction filtration through Florisil (produced by Wako Pure Chemical Industries, Ltd., Catalog No. 540-00135), Celite (produced by Wako Pure Chemical Industries, Ltd., Catalog No. 531-16855), and alumina to result in the filtrate. The filtrate was concentrated to give 2.5 g of an oily substance which was a target substance in 40% yield. The synthetic scheme of 4-(1-naphthyl)aniline is shown in (A-5).

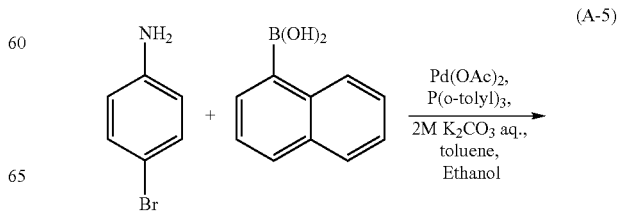

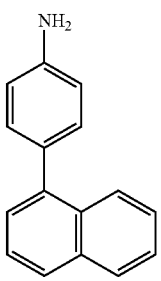

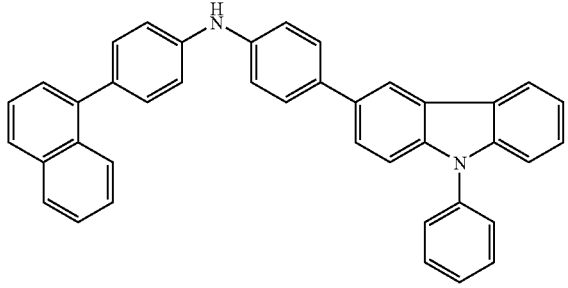

(301)

[Step 6: Synthesis of 4-(1-naphthyl)-4'-(9-phenyl-9H-carbazol-3-yl)diphenylamine (Abbreviated to PCBNA)]

To a 50 mL three-neck flask were added 0.8 g (2.0 mmol) 3-(4-bromophenyl)-9-phenyl-9H-carbazole and 0.6 g (6.0 mmol) of sodium tert-butoxide, and nitrogen substitution in the flask was carried out. After 0.4 g (2.0 mmol) of 4-(1-naphthyl)aniline in 4 mL of toluene was added to the mixture, 1.8 mL of toluene and 0.1 mL of tri(tert-butyl)phosphine (a 10 wt % hexane solution) were added to the mixture. The mixture was heated at 60° C., and then 37 mg (0.06 mmol) of bis(dibenzylideneacetone)palladium(0) was added. The mixture was stirred at 80° C. for 3 hours. After the reaction, toluene was added to the mixture, and a suction filtration through Celite (produced by Wako Pure Chemical Industries, Ltd., Catalog No. 531-16855) and alumina was carried out to give a filtrate. The filtrate was concentrated to give a solid, which was purified by silica gel column chromatography (developing solvent, hexane:toluene=3:2). The obtained fractions were concentrated to obtain 0.7 g of a brown solid which was a target substance in 63% yield. The synthetic scheme of PCBNA is shown in the following scheme (A-6).

(A-6)

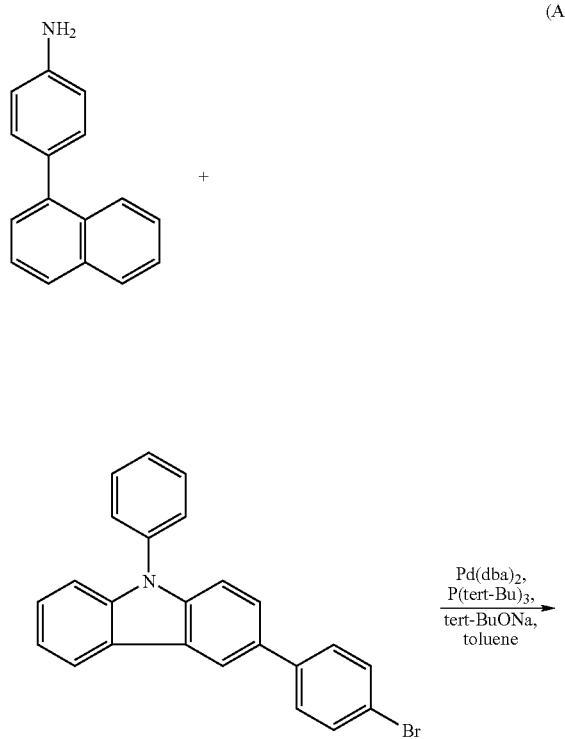

Figure 10A:
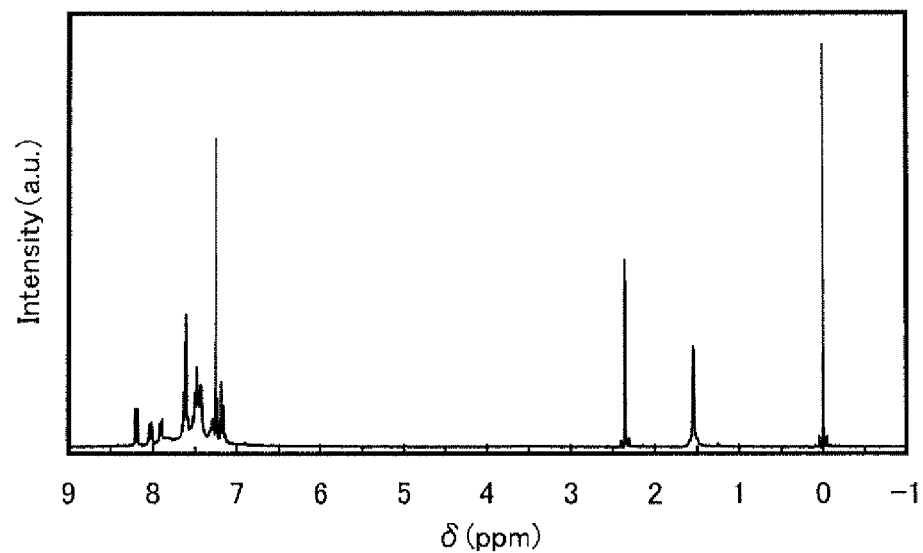
FIGS. 10A and 10B are diagrams showing $^1$H NMR charts of 4-(1-naphthyl)-4'-(9-phenyl-9H-carbazol-3-yl)diphenylamine (abbreviated to PCBNA)
Figure 10B:
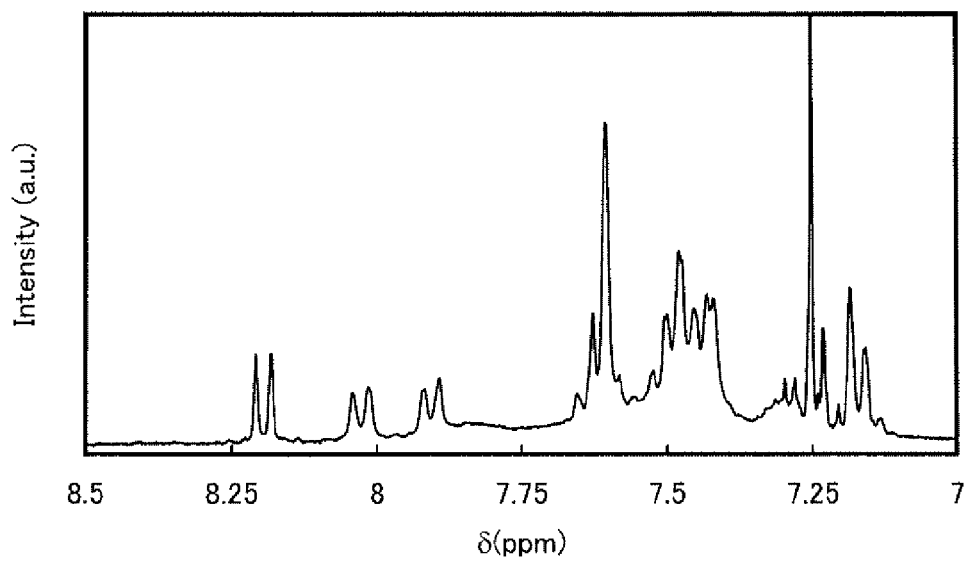

The solid obtained in the above Step 6 of Example 1 was analyzed by a nuclear magnetic resonance spectroscopy (NMR). The $^1$H NMR chart is shown in FIGS. 10A and 10B. FIG. 10B is a chart in which the range of 7.0 ppm to 8.5 ppm in FIG. 10A is expanded. The measurement results reveal that PCBNA which is represented by the above-mentioned structural formula (301), which is an organic compound of an embodiment of the present invention, and which is a starting material for the anthracene derivative of an embodiment of the present invention was obtained. The $^1$H NMR data are shown blow.

$^1$H NMR (CDCl$_3$, 300 MHz): δ=7.25-7.70 (m, 23H), 7.84 (d, J=7.8 Hz, 1H), 7.91 (d, J=7.2 Hz, 1H), 8.03 (d, J=8.1 Hz, 1H), 8.12 (d, J=7.2 Hz, 1H), 8.34 (s, 1H).

[Step 7: Synthesis of 4-(1-naphthyl)-4'-(10-phenyl-9-anthryl)-4''-(9-phenyl-9H-carbazol-3-yl)triphenylamine (Abbreviated to PCBNAPA)]

To a 50 mL three-neck flask were added 0.45 g (1.1 mmol) of 9-(4-bromophenyl)-10-phenylanthracene and 0.4 g (4.3 mmol) of sodium tert-butoxide, and the nitrogen substitution in the flask was carried out. After 0.8 g (1.4 mmol) of PCBNA in 10 mL of toluene was added to the mixture, 4.3 mL of toluene and 0.1 mL of tri(tert-butyl)phosphine (a 10 wt % of hexane solution) were added to the mixture. The mixture was heated at 60° C., and then 23 mg (0.04 mmol) of bis(dibenzylideneacetone)palladium(0) was added thereto. The mixture was stirred at 80° C. for 2 hours. After the reaction, suction filtration through Florisil (produced by Wako Pure Chemical Industries, Ltd., Catalog No. 540-00135), Celite (produced by Wako Pure Chemical Industries, Ltd., Catalog No, 531-16855), and alumina was carried out to obtain a filtrate. The resulting filtrate is concentrated to give a solid, which was purified by silica gel column chromatograph (developing solvent, hexane:toluene=3:7), and the obtained fractions were concentrated to result in a yellow solid which was a target substance. The resulting solid was recrystallized with a mixed solvent of toluene and hexane, leading to the formation of 1.07 g of a pale yellow powder which was a target substance in 85% yield. The synthetic scheme of PCBNAPA is shown in (A-7).

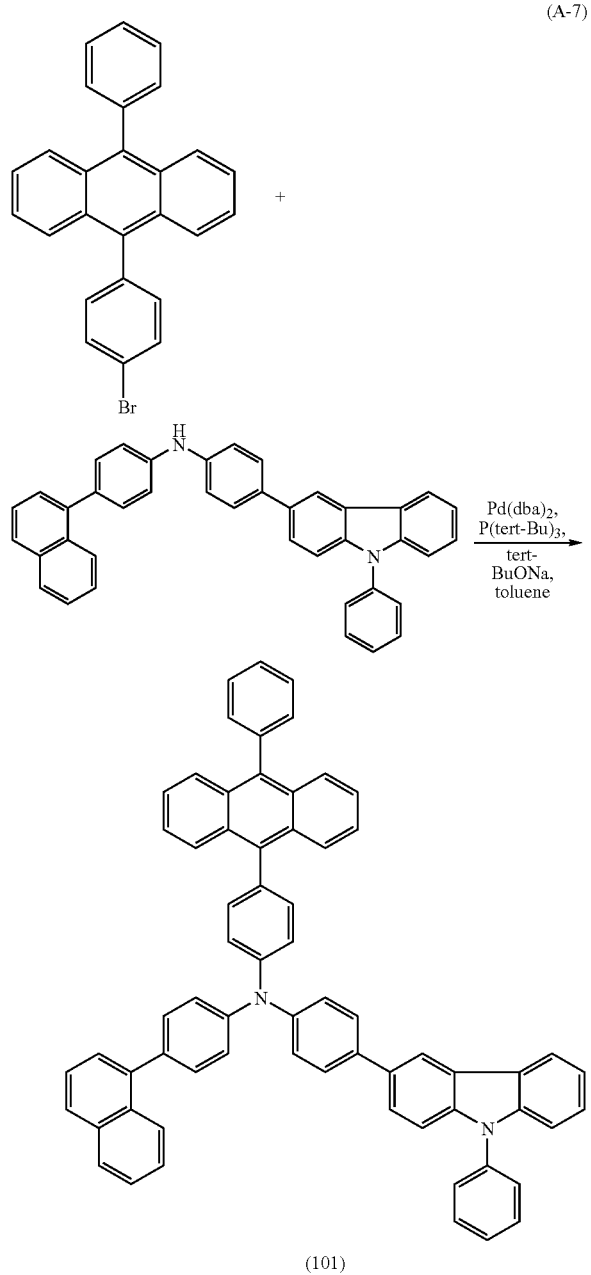

(A-7)

(101)

By a train sublimation method, 0.84 g of the obtained yellow solid was sublimated and purified. For sublimation purification conditions, the pale yellow solid was heated at 380° C. under a pressure of 4.5 Pa with a flow rate of argon gas of 5 mL/min. After the sublimation purification, 0.76 g of a yellow prismatic crystal which was a target substance was recovered in 91% yield.

Figure 11A:
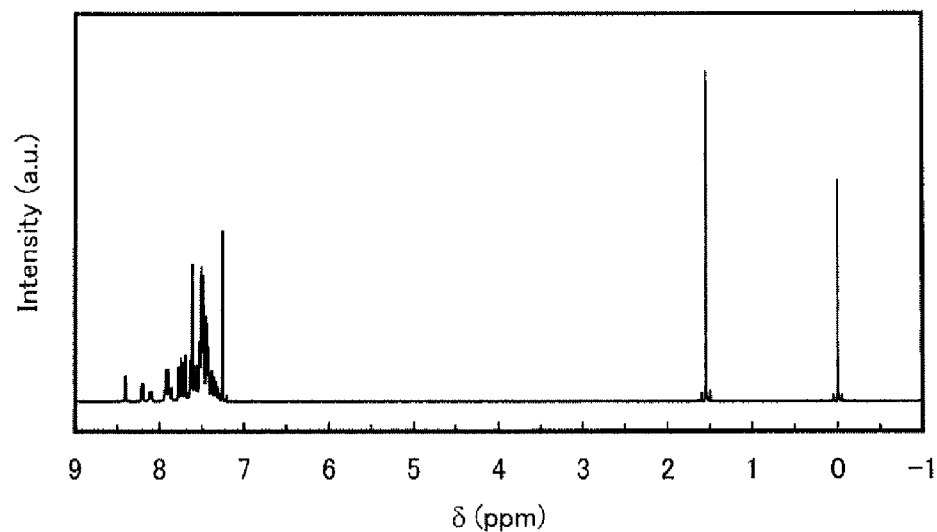
FIGS. 11A and 11B are diagrams showing $^1$H NMR charts of 4-(1-naphthyl)-4'-(10-phenyl-9-anthryl)-4"-(9-phenyl-9H-carbazol-3-yl)triphenylamine (abbreviated to PCBNAPA)
Figure 11B:
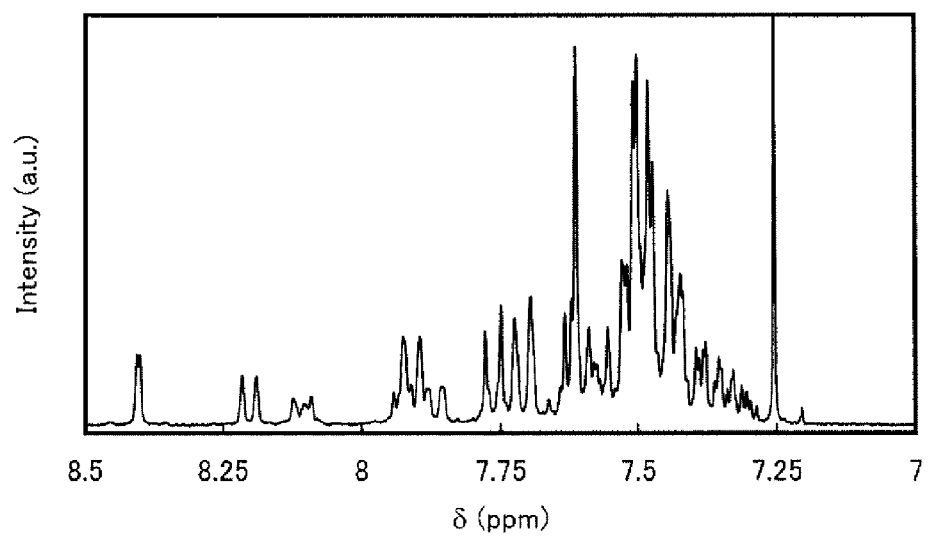

The solid obtained in the above Step 7 was analyzed by $^1$H NMR. The $^1$H NMR chart is shown in FIGS. 11A and 11B. FIG. 11B is a chart in which the range of 7.0 ppm to 8.5 ppm in FIG. 11A is expanded. From the measurement results, it was confirmed that the anthracene derivative PCBNAPA which is an embodiment of the present invention and is represented by the above structural formula (101) was obtained. The measurement data are described below.

$^1$H NMR (CDCl$_3$, 300 MHz): δ=7.28-7.66 (m, 31H), 7.70-7.78 (m, 6H), 7.85-7.94 (m, 4H), 8.09-8.12 (m, 1H), 8.20 (d, J=7.8 Hz, 1H), 8.40 (d, J=1.2 Hz, 1H).

The thermogravimetry-differential thermal analysis (TG-DTA) of the obtained PCBNAPA was carried out. The measurement was conducted by using a high vacuum differential type differential thermal balance (manufactured by Bruker AXS K.K., TG/DTA 2410SA). The measurement was carried under nitrogen stream (flow rate: 200 mL/min) and a normal pressure at a temperature rising rate of 10° C./min. From the relationship between the weight change and the temperature (thermogravimetry), it was understood that a 5% weight loss temperature was higher than 500° C., which is indicative of high thermal stability.

Figure 12:
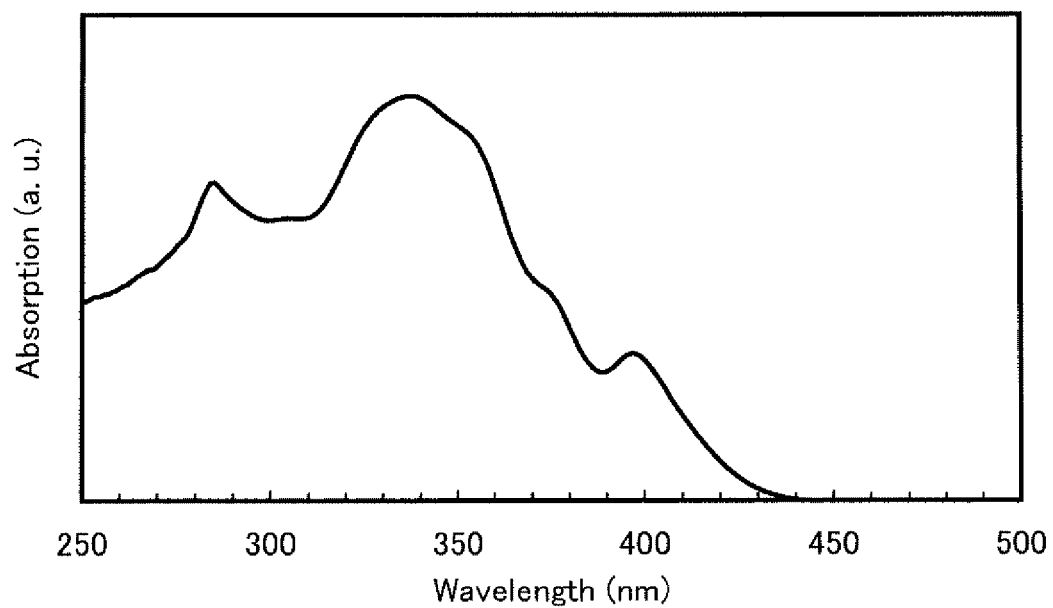
FIG. 12 is a diagram showing an absorption spectrum of a toluene solution of 4-(1-naphthyl)-4'-(10-phenyl-9-anthryl)-4"-(9-phenyl-9H-carbazol-3-yl)triphenylamine (abbreviated to PCBNAPA)
Figure 13:
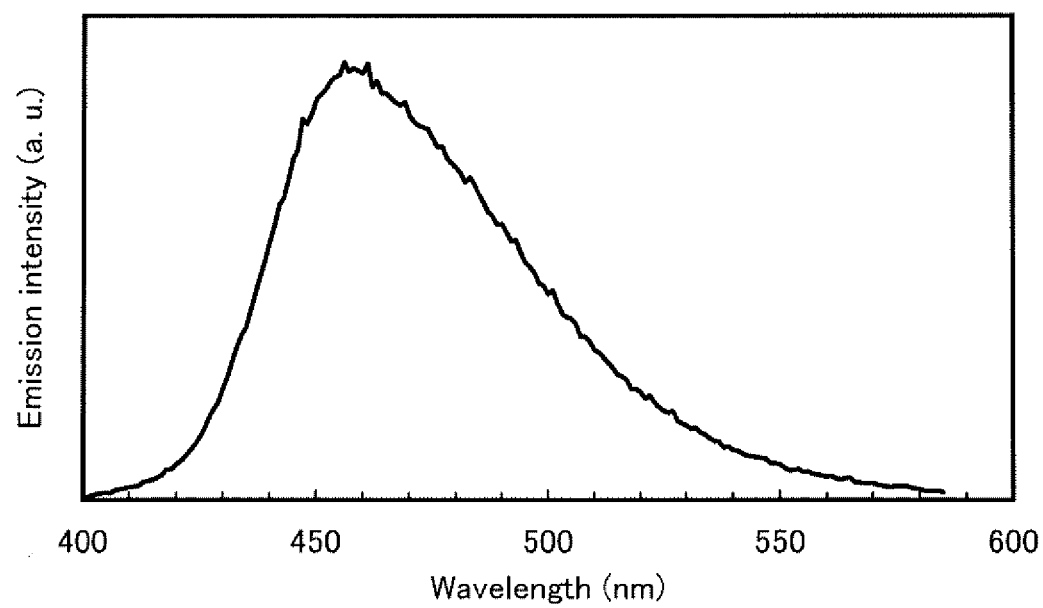
FIG. 13 is a diagram showing an emission spectrum of a toluene solution of 4-(1-naphthyl)-4'-(10-phenyl-9-anthryl)-4"-(9-phenyl-9H-carbazol-3-yl)triphenylamine (abbreviated to PCBNAPA)

The absorption spectrum and the emission spectrum of a toluene solution of PCBNAPA are shown in FIG. 12 and FIG. 13, respectively. An ultraviolet-visible spectrophotometer (V-550, by JASCO Corporation) was used for the measurement of the absorption spectrum of the toluene solution in a quartz cell. The absorption spectrum was obtained after subtracting an absorption spectrum of toluene in the quartz cell. In FIG. 12, the horizontal axis indicates the wavelength (nm) and the vertical axis indicates absorption intensity (arbitrary unit). In FIG. 13, the horizontal axis indicates the wavelength (nm) and the vertical axis indicates the light emission intensity (arbitrary unit). Absorption is observed around 337 nm, 375 nm, and 397 nm for the toluene solution. The maximum emission wavelength of the solution was 457 nm (excitation wavelength: 370 nm).

Figure 14:
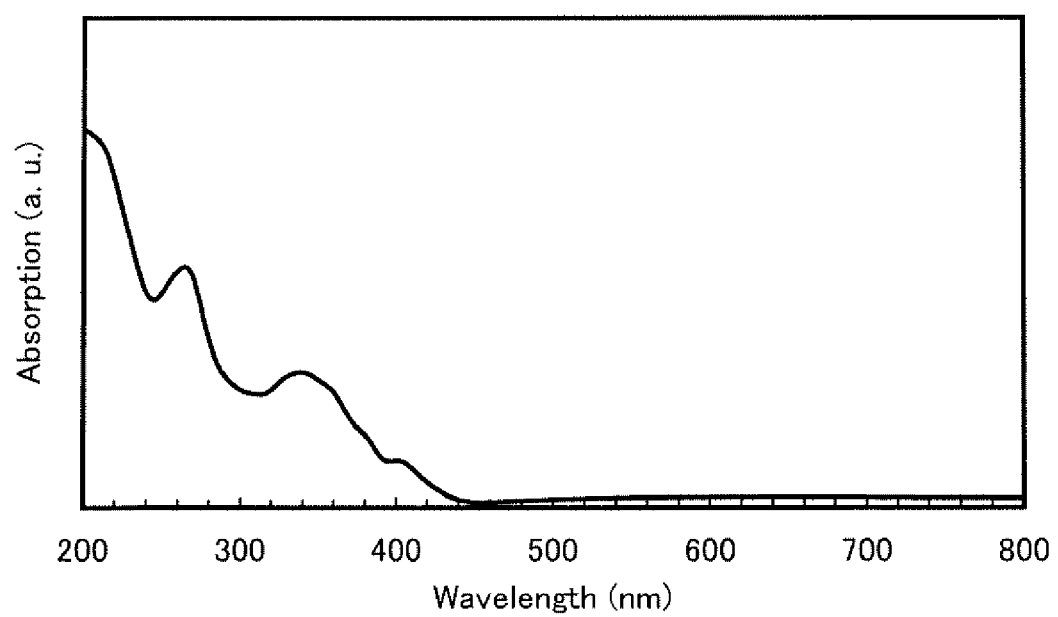
FIG. 14 is a diagram showing an absorption spectrum of a thin film of 4-(1-naphthyl)-4'-(10-phenyl-9-anthryl)-4''-(9-phenyl-9H-carbazol-3-yl)triphenylamine (abbreviated to PCBNAPA)
Figure 15:
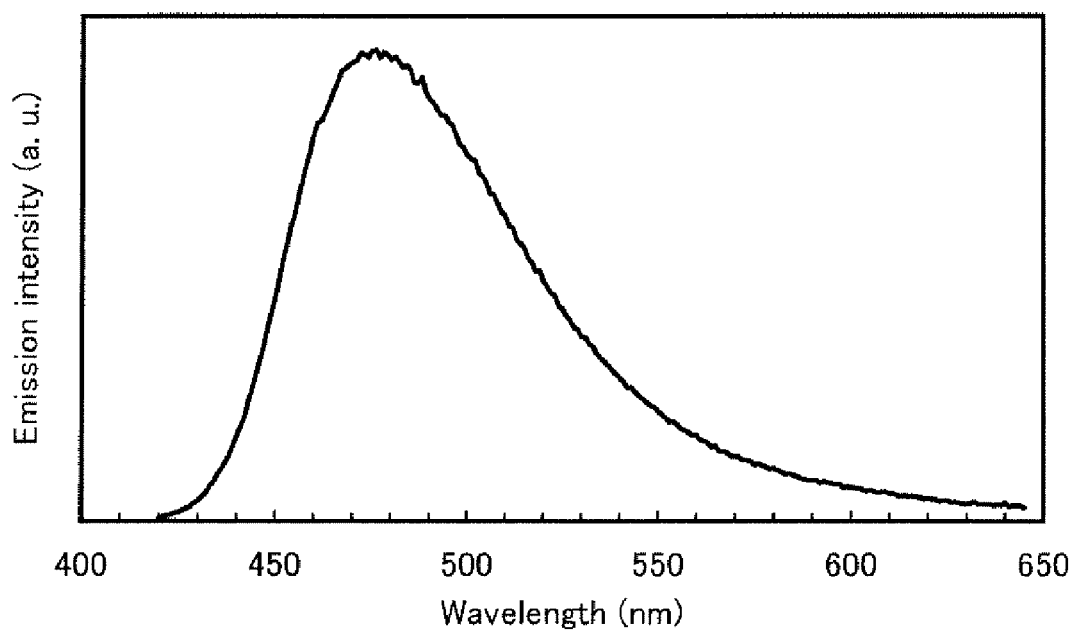
FIG. 15 is a diagram showing an emission spectrum of a thin film of 4-(1-naphthyl)-4'-(10-phenyl-9-anthryl)-4''-(9-phenyl-9H-carbazol-3-yl)triphenylamine (abbreviated to PCBNAPA)

The absorption spectrum and the emission spectrum of a thin film of PCBNAPA are illustrated in FIG. 14 and FIG. 15, respectively. An ultraviolet-visible spectrophotometer (V-550, by JASCO Corporation) was used for the measurement of the absorption spectrum. The sample was prepared by evaporation on a quartz substrate for measurement. The absorption spectrum was obtained after subtracting an absorption spectrum of the quartz cell. In FIG. 14, the horizontal axis indicates the wavelength (nm) and the vertical axis indicates absorption intensity (arbitrary unit). In FIG. 15, the horizontal axis indicates the wavelength (nm) and the vertical axis indicates the light emission intensity (arbitrary unit). In the case of the thin film, absorption was observed around 339 nm, 357 nm, 375 nm, and 401 nm. The maximum emission wavelength was 476 nm (excitation wavelength: 401 nm) in the case of the thin film.

As discussed above, the measurements reveal that the anthracene derivative PCBNAPA, which is represented by the structural formula (101) and is an embodiment of the present invention, exhibits blue light emission of a sufficiently short wavelength and with favorable chromaticity both in solution and in the thin film state.

The oxidation characteristic and reduction characteristic of PCBNAPA were evaluated. The oxidation characteristic and reduction characteristic were evaluated by cyclic voltammetry (CV) measurement. An electrochemical analyzer (ALS model 600A, BAS Inc.) was used for the measurement.

The solution for the CV measurement was prepared by using dehydrated N,N-dimethylformamide (DMF) (produced by Sigma-Aldrich Corp., 99.8%, catalog number: 22705-6) as a solvent, dissolving a supporting electrolyte of tetra-n-butylammonium perchlorate (n-Bu$_4$NClO$_4$) (produced by Tokyo Chemical Industry Co., Ltd., catalog number: T0836) at a concentration of 100 mmol/L, and dissolving the sample at a concentration of 1 mmol/L. A platinum electrode (a PTE platinum electrode, BAS Inc.) was used as a work electrode, a platinum electrode (a VC-3 Pt counter electrode (5 cm), BAS Inc.) was used as an auxiliary electrode, and an Ag/Ag+ electrode (an RE5 non-aqueous solvent reference electrode, BAS Inc.) was used as a reference electrode. The measurement was carried out at room temperature. The scan speed at these CV measurements was set at 0.1 V/s.

The reduction characteristics of PCBNAPA were evaluated by 100 measurement cycles where the potential of the working electrode with respect to the reference electrode was scanned from −1.22 V to −2.40 V and then scanned from −2.40 V to −1.22 V in each of the cycles. Similarly, the oxidation characteristics were evaluated by 100 measurement cycles where the potential was scanned from 0.28 V to 0.60 V and then scanned from 0.60 V to 0.28 V in each of the cycles.

Figure 16A:
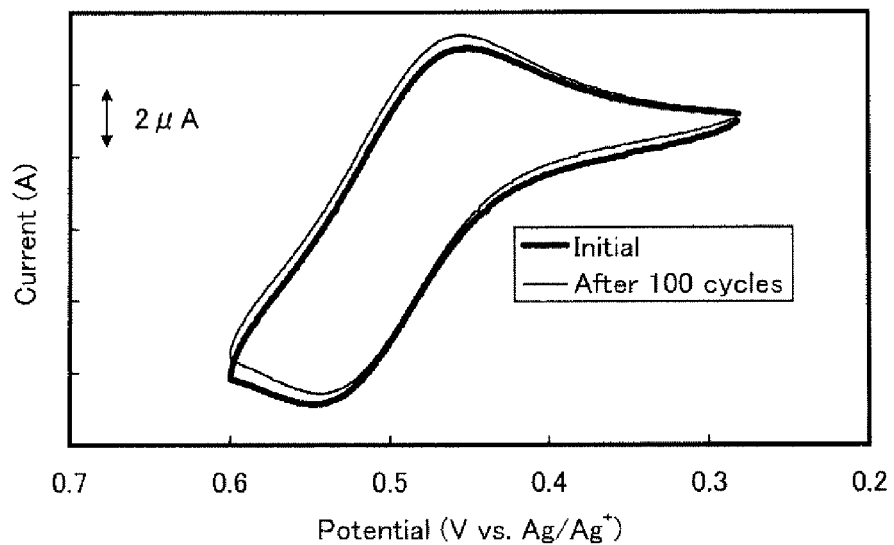
FIGS. 16A and 16B are diagrams showing a CV chart of a DMF solution of 4-(1-naphthyl)-4'-(10-phenyl-9-anthryl)-4''-(9-phenyl-9H-carbazol-3-yl)triphenylamine (abbreviated to PCBNAPA)
Figure 16B:
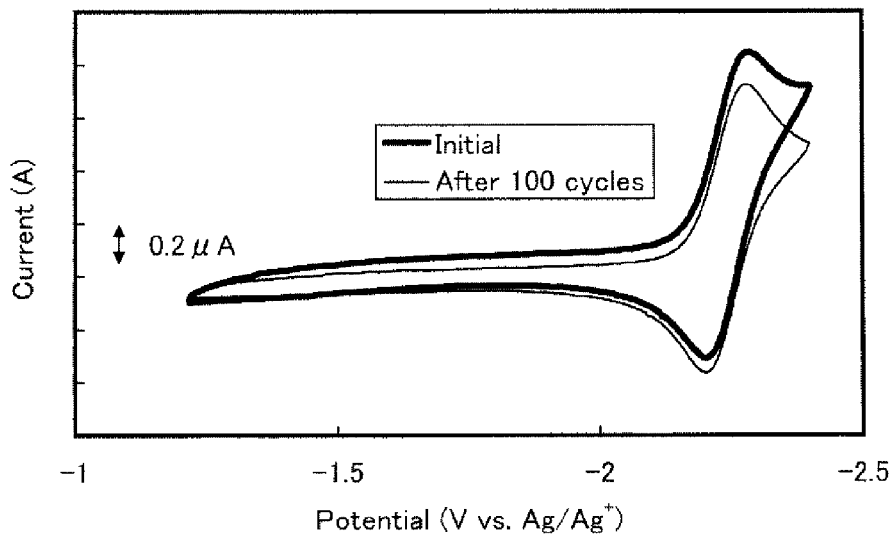

FIGS. 16A and 16B show CV measurement results on the oxidation characteristic and reduction characteristic of PCBNAP, respectively. In FIGS. 16A and 16B, the horizontal axis indicates a potential (V) of the working electrode with respect to the reference electrode, and the vertical axis indicates a current value (μA) flowing between the working electrode and the auxiliary electrode.

It can be understood from FIG. 16A that the current corresponding to the oxidation is observed around 0.50 V (vs. Ag/Ag+) and from FIG. 16B that the current corresponding to the reduction is observed around −2.24 V (vs. Ag/Ag+).

Although the scan was repeated as many as 100 cycles, PCBNAPA showed no significant change in the peak position and peak intensity of the CV curves in the oxidation and the reduction. The peak intensity remained 96% of the initial state on the oxidation side and 86% of the initial state on the reduction side. Thus, it is understood that PCBNAPA is relatively stable even when an oxidation from a neutral state to an oxidized state and a reduction from the oxidized state to the neutral state are repeated and when a reduction from the neutral state to a reduced state and an oxidation from the reduced state to the neutral state are repeated.

The results of measuring the thin film of PCBNAPA by photoelectron spectrometry (AC-2, product of Riken Keiki Co., Ltd.) under air indicated that the HOMO level of PCBNAPA is −5.47 eV. The absorption edge was obtained from Tauc plot, with an assumption of direct transition, using data on the absorption spectrum in FIG. 14, and the energy gap thereof was estimated to be 2.92 eV assuming that the absorption edge corresponds to the optical energy gap. The LUMO level was found to be −2.55 eV by calculation from the value of the energy gap and the HOMO level. As thus described, it was found that PCBNAPA has a large energy gap of 2.92 eV.

EXAMPLE 2

In this example, specific explanation is given for the synthetic methods of 4-[4-(1-naphthyl)phenyl]-4'-(10-phenyl-9-anthryl)-4''-(9-phenyl-9H-carbazol-3-yl)triphenylamine (abbreviated to PCBNBAPA), which is an anthracene derivative of an embodiment of the present invention and is represented by the structural formula (103), and 4-[4-(1-naphthyl)phenyl]-4'-(9-phenyl-9H-carbazol-3-yl)diphenylamine (abbreviated to PCBNBA) which is used in the synthesis of PCBNBAPA and is represented by the structural formula (302).

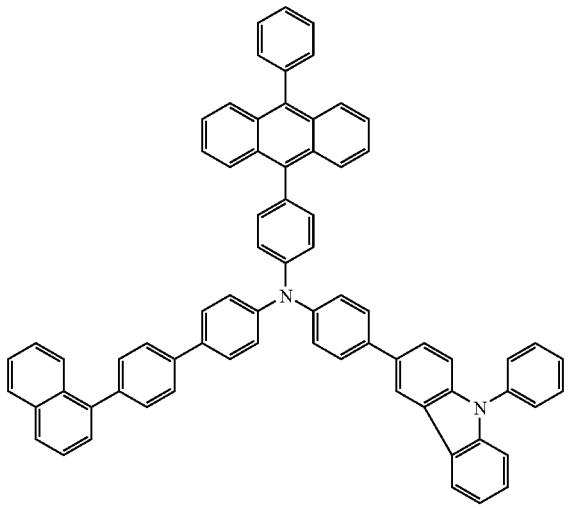

(103)

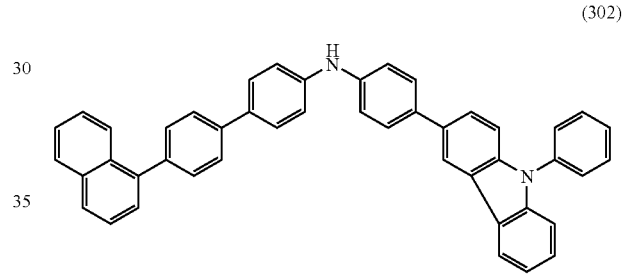

(302)

[Step 1: Synthesis of 4'-(1-naphthyl)biphenyl-4-amine]

To a 50 mL three-neck flask were added 0.70 g (4 mmol) of 4-bromoaniline, 1.0 g (4 mmol) of 4-(1-naphthyl)phenylboronic acid, and 61.8 mg (0.2 mmol) of tris(o-tolyl)phosphine, and nitrogen substitution in the flask was carried out. To the mixture were added 14 mL of toluene, 6 mL of ethanol, and 4 mL of an aqueous solution of potassium carbonate (2 mol/L). The mixture was stirred to be degassed under a reduced pressure, and then the mixture was heated at 60° C., which was followed by addition of 11.9 mg (0.05 mmol) of palladium(II) acetate. This mixture was stirred at 80° C. for 1.5 hours. After the reaction, toluene and water were added to the mixture, the organic layer and the aqueous layer were separated from each other, and the aqueous layer was extracted twice with toluene. The obtained extract and the organic layer were combined, washed with brine, and dried with magnesium sulfate. The mixture was subjected to gravity filtration to remove magnesium sulfate, and the filtrate was concentrated to obtain an oily product. The oily product was subjected to suction filtration through Florisil (produced by Wako Pure Chemical Industries, Ltd., Catalog No. 540-00135), Celite (produced by Wako Pure Chemical Industries, Ltd., Catalog No. 531-16855), and alumina, resulting in a filtrate. The filtrate obtained was concentrated to give 1.1 g of an oily substance which was a target substance in 95% yield. The synthetic scheme of 4'-(1-naphthyl)biphenyl-4-amine is shown in (B-1).

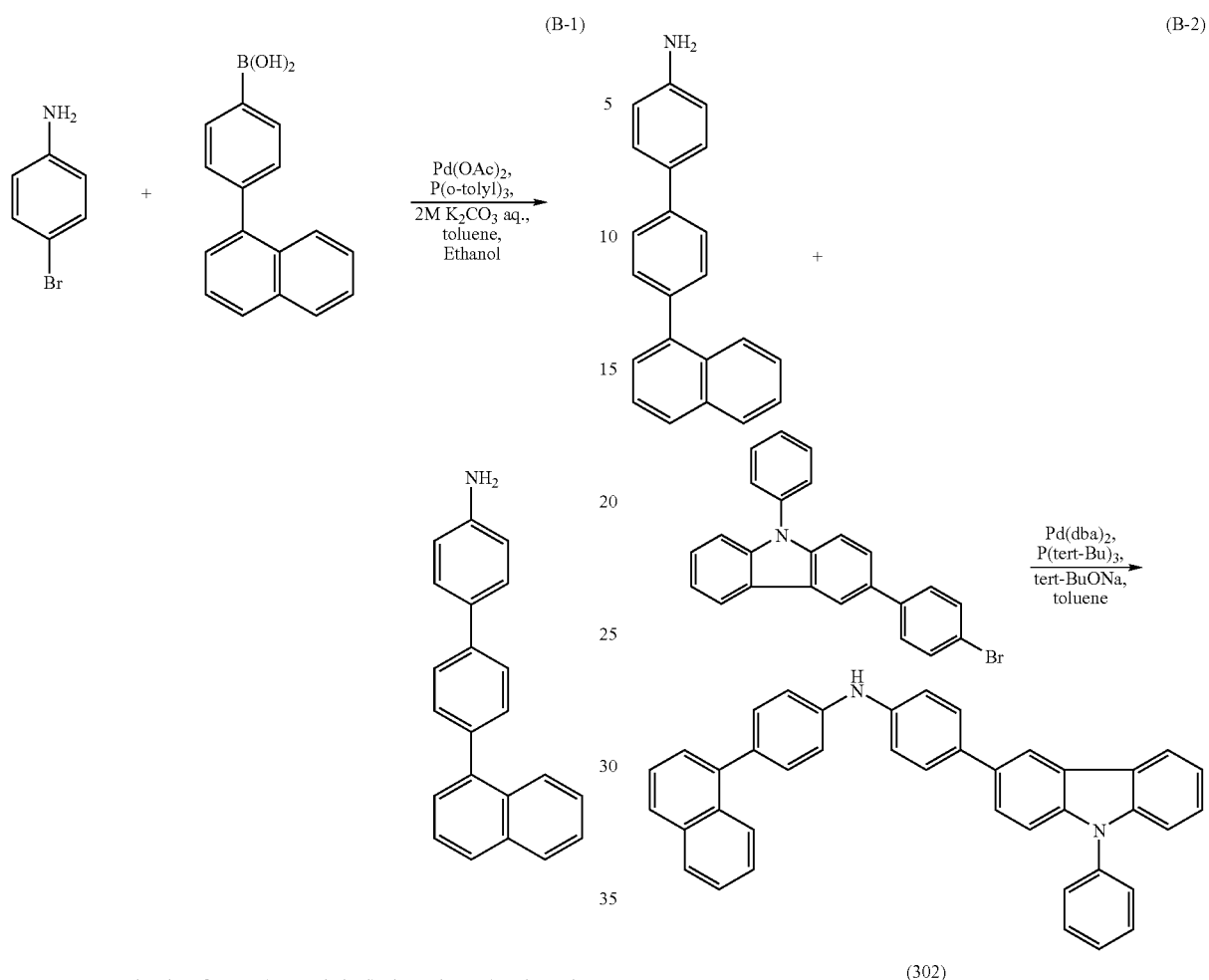

[Step 2: Synthesis of 4-[4-(1-naphthyl)phenyl]-4'-(9-phenyl-9H-carbazol-3-yl)diphenylamine (Abbreviated to PCB-NBA)]

To a 50 mL three-neck flask was added 1.1 g (11.4 mmol) of sodium tert-butoxide, and nitrogen substitution in the flask was carried out. After 1.1 g (3.8 mmol) of 4'-(1-naphthyl)biphenyl-4-amine dissolved in 12 mL of toluene and 1.5 g (3.8 mmol) of 3-(4-bromophenyl)-9-phenyl-9H-carbazole dissolved in 18 mL of toluene were added to the flask, 0.2 mL of tri(tert-butyl)phosphine (a 10 wt % of hexane solution) was added. After the mixture was stirred at 60° C., 35.5 mg (5.7 mmol) of bis(dibenzylideneacetone)palladium(0) was added. Then, this mixture was heated with stirring at 80° C. for 4.5 hours. After the reaction, the mixture was subjected to suction filtration through Florisil (produced by Wako Pure Chemical Industries, Ltd., Catalog No. 540-00135), Celite (produced by Wako Pure Chemical Industries, Ltd., Catalog No. 531-16855), and alumina, resulting in a filtrate. The filtrate was concentrated, and the resulting solid was purified by silica gel column chromatography (developing solvent: chloroform:hexane=1:1). The obtained fractions were concentrated to obtain 1.8 g of a brown solid which was a target substance in 76% yield. The synthetic scheme of PCBNBA is shown in the following scheme (B-2).

Figure 17A:
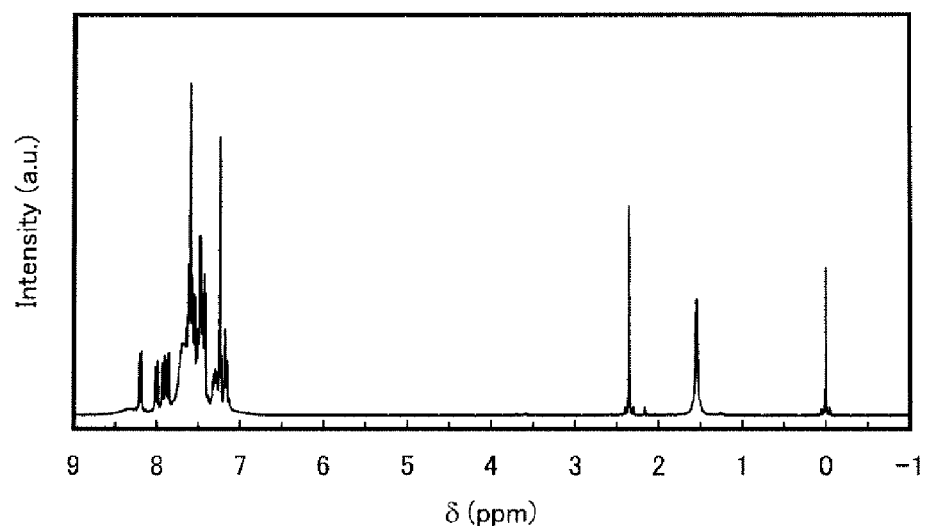
FIGS. 17A and 17B are diagrams showing $^1$H NMR charts of 4-[4-(1-naphthyl)phenyl]-4'-(9-phenyl-9H-carbazol-3-yl)diphenylamine (abbreviated to PCBNBA)
Figure 17B:
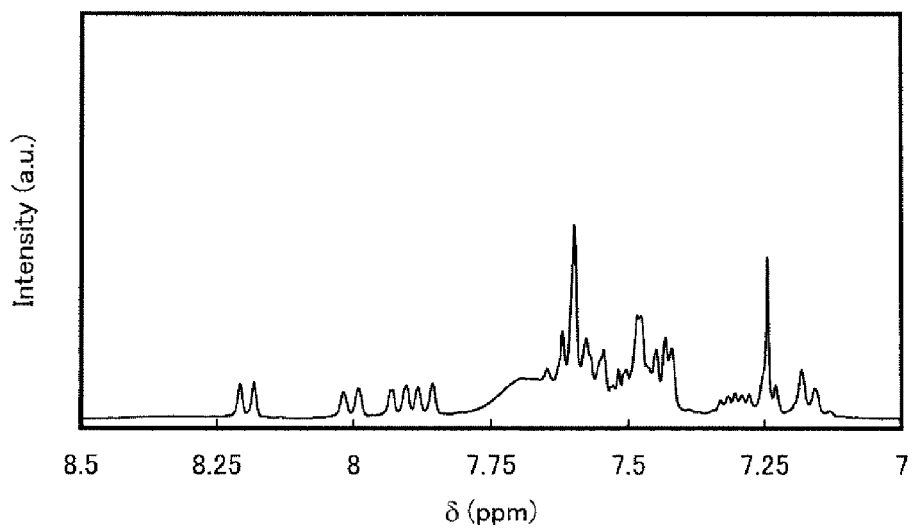

The solid obtained in the above Step 2 of Example 2 was analyzed by nuclear magnetic resonance spectroscopy (NMR). The $^1$H NMR chart is shown in FIGS. 17A and 17B. FIG. 17B is a chart in which the range of 7.0 ppm to 8.5 ppm in FIG. 17A is expanded. The measurement results reveal that PCBNBA which is represented by the above-mentioned structural formula (302), which is an organic compound of an embodiment of the present invention, and which is a starting material for an anthracene derivative of an embodiment of the present invention, PCBNBAPA, was obtained. The $^1$H NMR data are shown blow.

$^1$H NMR (CDCl$_3$, 300 MHz): δ=7.28-7.70 (m, 28H), 7.87 (d, J=7.8 Hz, 1H), 7.92 (d, J=7.8 Hz, 1H), 8.01 (d, J=7.8 Hz, 1H), 8.20 (d, J=7.8 Hz, 1H).

[Step 3: Synthesis of 4-[4-(1-naphthyl)phenyl]-4'-(10-phenyl-9-anthryl)-4"-(9-phenyl-9H-carbazol-3-yl)triphenylamine (Abbreviated to PCBNBAPA)]

To a 50 mL three-neck flask were added 0.60 g (1.5 mmol) of 9-(4-bromophenyl)-10-phenylanthracene, 0.40 g (4.4 mmol) of sodium tert-butoxide, and 0.90 g (1.5 mmol) of PCBNBA, and nitrogen substitution in the flask was carried out. To the mixture were added 10 mL of toluene and 0.10 mL of tri(tert-butyl)phosphine (a 10 wt % hexane solution). After the mixture was stirred at 60° C., 42 mg (7.3 mmol) of bis(dibenzylideneacetone)palladium(0) was added. This mixture was stirred at 80° C. for 6 hours. After the stirring, 23 mg (4.0 mmol) of bis(dibenzylideneacetone)palladium(0)

was further added, and the stirring at 95° C. was further conducted for 1 hour. After the reaction, the mixture was subjected to suction filtration through Florisil (produced by Wako Pure Chemical Industries, Ltd., Catalog No. 540-00135), Celite (produced by Wako Pure Chemical Industries, Ltd., Catalog No. 531-16855), and alumina, and the resulting filtrate was concentrated to give a solid. The solid was purified by silica gel column chromatography (developing solvent: hexane:toluene=3:7), giving a yellow solid which was a target substance. The obtained solid was recrystallized with a mixed solvent of chloroform and hexane to give 0.70 g of a pale yellow powder which was a target substance in 52% yield. The synthetic scheme of PCBNBAPA is shown in the following scheme (B-3).

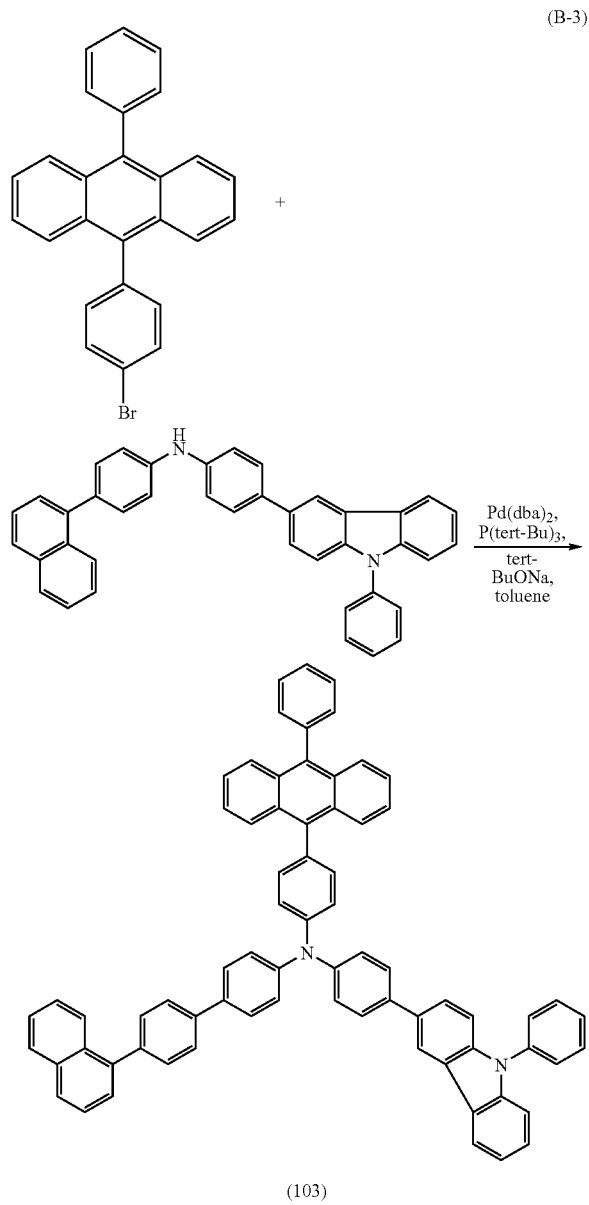

0.70 g of the obtained yellow solid was sublimated and purified by a train sublimation method. Under the sublimation conditions of the pressure of 4.2 Pa and the argon gas flow rate of 10 mL/min, the pale yellow solid was heated at 430° C. After the sublimation purification, 0.50 g of a yellow prismatic crystal which is a target substance was recovered in 68% yield.

Figure 18A:
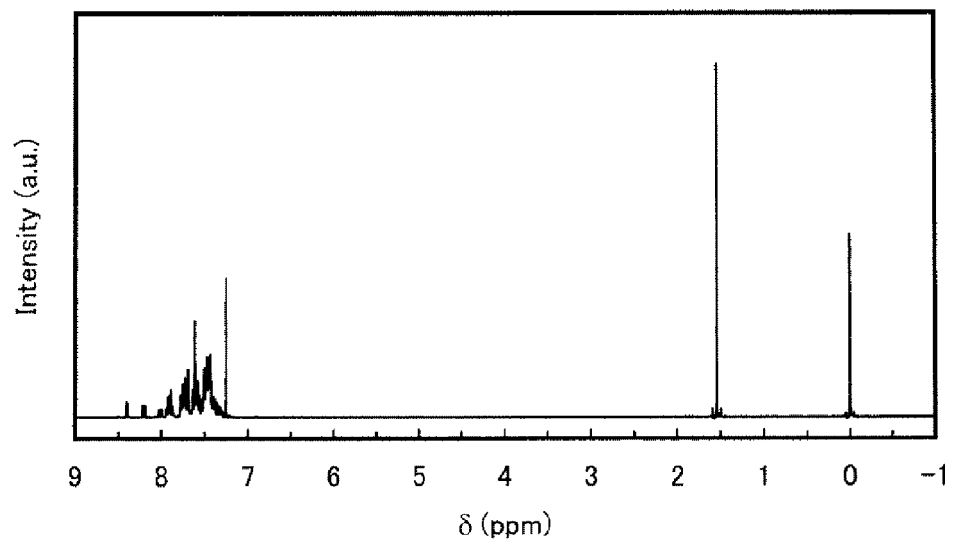
FIGS. 18A and 18B are diagrams showing $^1$H NMR charts of 4-[4-(1-naphthyl)phenyl]-4'-(10-phenyl-9-anthryl)-4''-(9-phenyl-9H-carbazol-3-yl)triphenylamine (abbreviated to PCBNBAPA)
Figure 18B:
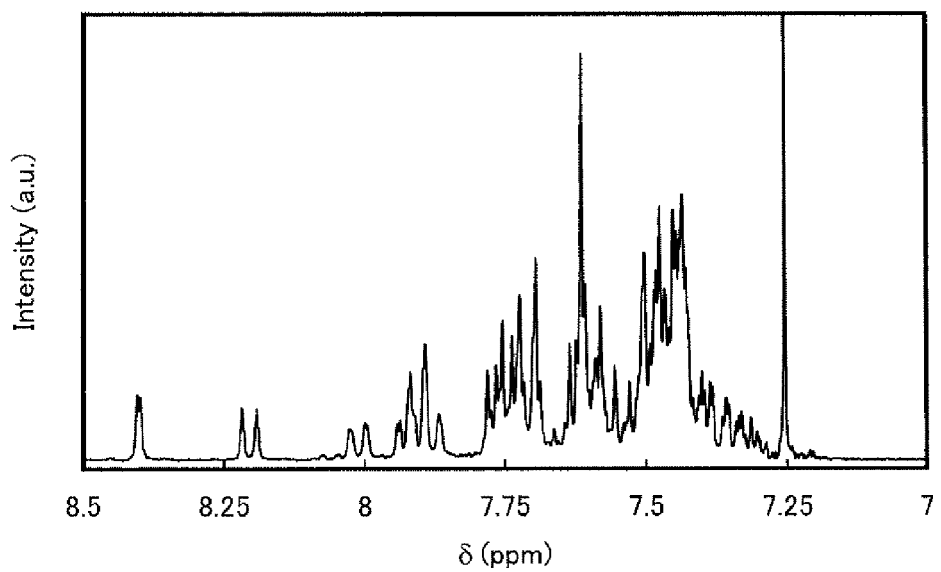

The solid obtained in the above Step 3 of Example 2 was analyzed by nuclear magnetic resonance spectroscopy (NMR). $^1$H-NMR chart is shown in FIGS. 18A and 18B. FIG. 18B is a chart in which the range of 7.0 ppm to 8.5 ppm in FIG. 18A is expanded. From the measurement results, it can be confirmed that the anthracene derivative PCBNBAPA which is an embodiment of the present invention and represented by the above structural formula (103) was obtained. The $^1$H NMR data are shown blow.

$^1$H NMR (CDCl$_3$, 300 MHz): δ=7.31-7.78 (m, 41H), 7.87-7.94 (m, 4H), 8.01 (d, J=8.1 Hz, 1H), 8.21 (d, J=7.8 Hz, 1H), 8.42 (d, J=0.9 Hz, 1H).

The thermogravimetry-differential thermal analysis (TG-DTA) of the thus obtained PCBNBAPA was carried out. The measurement was conducted by using a high vacuum differential type differential thermal balance (manufactured by Bruker AXS K.K., TG/DTA 24105A). The measurement was carried under nitrogen stream (flow rate: 200 mL/min) and a normal pressure at a temperature rising rate of 10° C./min. From the relationship between the weight change and the temperature (thermogravimetry), it was understood that a 5% weight loss temperature was higher than 500° C., which is indicative of high thermal stability.

Figure 19:
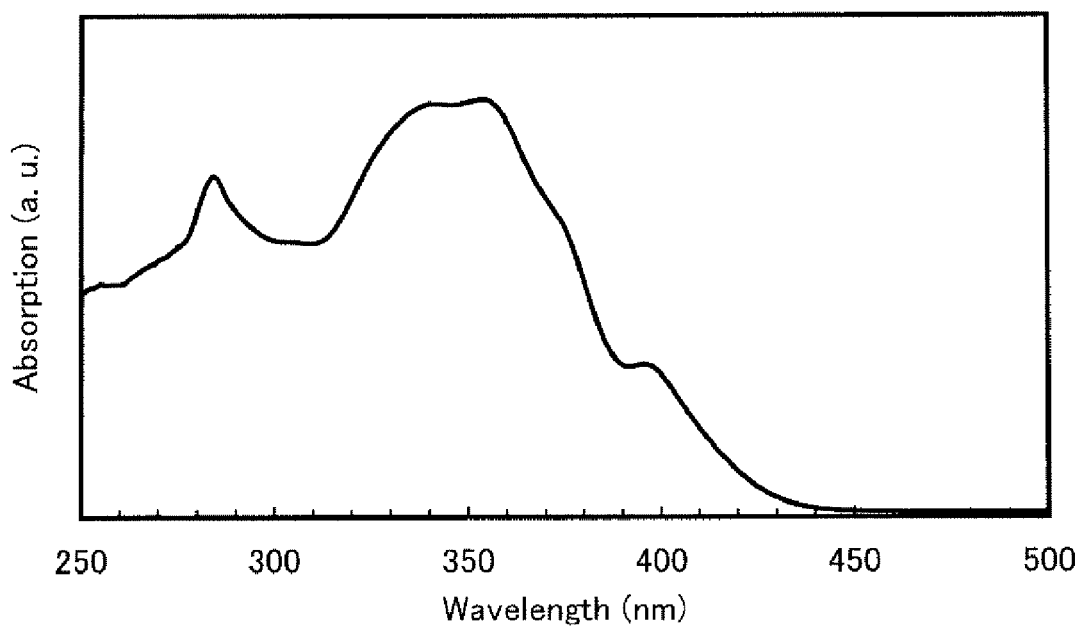
FIG. 19 is a diagram showing an absorption spectrum of a toluene solution of 4-[4-(1-naphthyl)phenyl]-4'-(10-phenyl-9-anthryl)-4''-(9-phenyl-9H-carbazol-3-yl)triphenylamine (abbreviated to PCBNBAPA)
Figure 20:
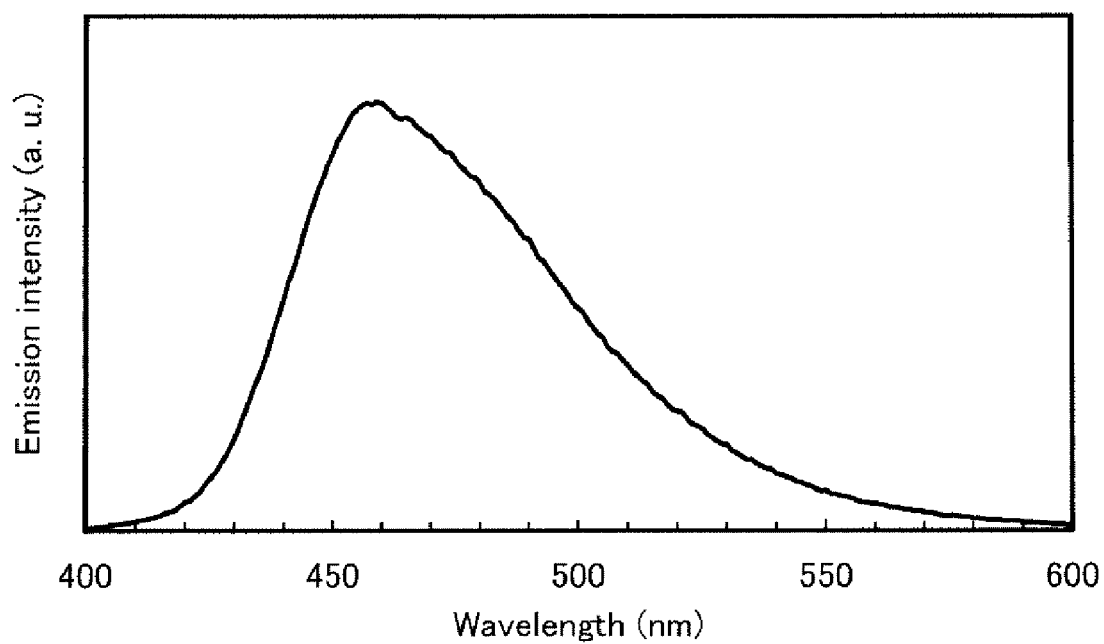
FIG. 20 is a diagram showing an emission spectrum of a toluene solution of 4-[4-(1-naphthyl)phenyl]-4'-(10-phenyl-9-anthryl)-4''-(9-phenyl-9H-carbazol-3-yl)triphenylamine (abbreviated to PCBNBAPA)

The absorption spectrum and the emission spectrum of a toluene solution of PCBNBAPA are shown in FIG. 19 and FIG. 20, respectively. An ultraviolet-visible spectrophotometer (V-550, by JASCO Corporation) was used for the measurement of the absorption spectrum of the solution in a quartz cell in measurement. The absorption spectrum was obtained after subtracting an absorption spectrum of toluene in the quartz cell. In FIG. 19, the horizontal axis shows a wavelength (nm) while the vertical axis shows absorption intensity (arbitrary unit). In FIG. 20, the horizontal axis indicates the wavelength (nm) and the vertical axis indicates the emission intensity (arbitrary unit). Absorption is observed around 353 nm and 395 nm for the toluene solution. The maximum emission wavelength of the solution was 459 nm (excitation wavelength: 370 nm).

Figure 21:
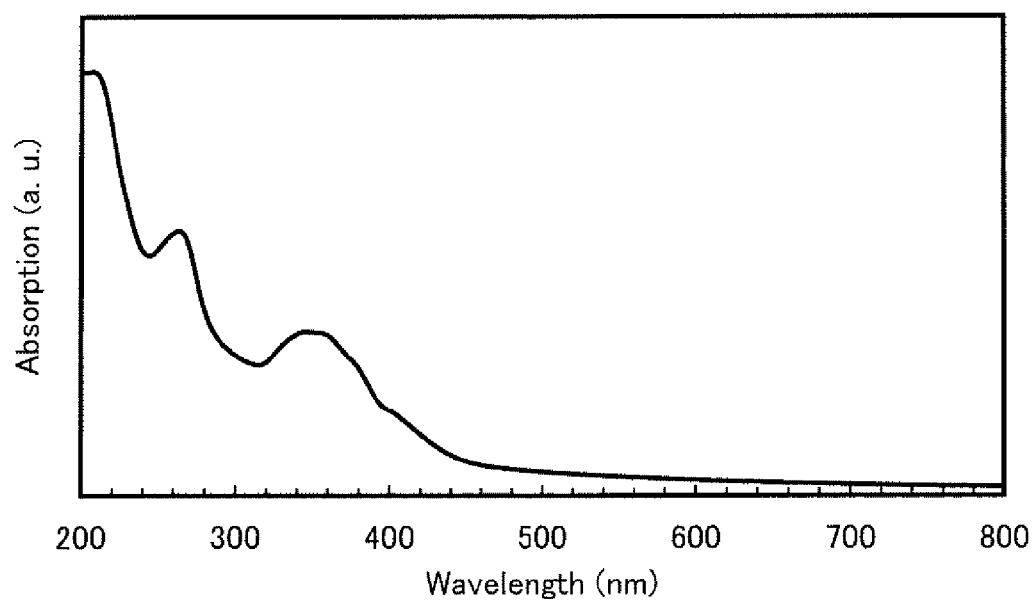
FIG. 21 is a diagram showing an absorption spectrum of a thin film of 4-[4-(1-naphthyl)phenyl]-4'-(10-phenyl-9-anthryl)-4''-(9-phenyl-9H-carbazol-3-yl)triphenylamine (abbreviated to PCBNBAPA)
Figure 22:
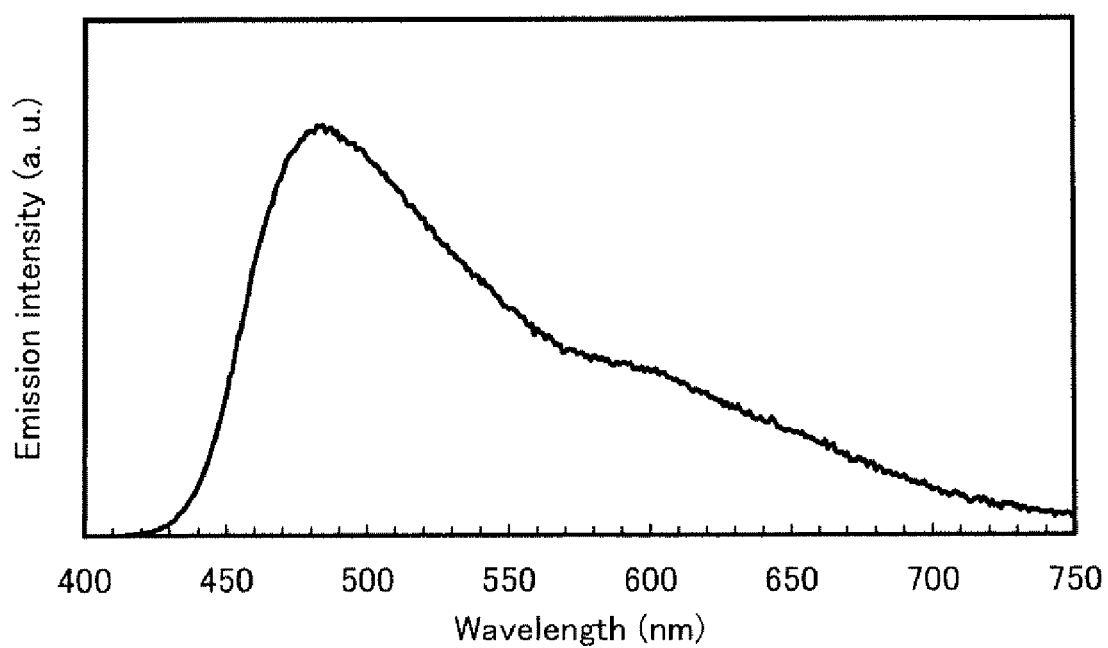
FIG. 22 is a diagram showing an emission spectrum of a thin film of 4-[4-(1-naphthyl)phenyl]-4'-(10-phenyl-9-anthryl)-4''-(9-phenyl-9H-carbazol-3-yl)triphenylamine (abbreviated to PCBNBAPA)

The absorption spectrum and the emission spectrum of a thin film of PCBNBAPA are illustrated in FIG. 21 and FIG. 22, respectively. An ultraviolet-visible spectrophotometer (V-550, by JASCO Corporation) was used for the measurement of the absorption spectrum. The sample was prepared by evaporation on a quartz substrate for measurement. The absorption spectrum illustrated was obtained after subtracting an absorption spectrum of the quartz cell. In FIG. 21, the horizontal axis indicates the wavelength (nm) and the vertical axis indicates absorption intensity (arbitrary unit). In FIG. 22, the horizontal axis indicates the wavelength (nm) and the vertical axis indicates the light emission intensity (arbitrary unit). In the case of the thin film, absorption was observed around 354 nm and 403 nm. The maximum emission wavelength was 483 nm (excitation wavelength: 400 nm) in the case of the thin film.

As discussed above, it is found that the anthracene derivative PCBNBAPA, which is represented by the structural formula (103) and is an embodiment of the present invention, exhibits blue light emission of a sufficiently short wavelength and with favorable chromaticity both in solution and in the thin film state.

The oxidation characteristic and reduction characteristic of PCBNBAPA were evaluated. The oxidation characteristic and reduction characteristic were evaluated by cyclic voltammetry (CV) measurement. An electrochemical analyzer (ALS model 600A, BAS Inc.) was used for the measurement.

The solution for the CV measurement was prepared by using dehydrated N,N-dimethylformamide (DMF) (produced by Sigma-Aldrich Corp., 99.8%, catalog number: 22705-6) as a solvent, dissolving a supporting electrolyte of tetra-n-butylammonium perchlorate (n-Bu$_4$NClO$_4$) (produced by Tokyo Chemical Industry Co., Ltd., catalog number: T0836) at a concentration of 100 mmol/L, and dissolving the sample at a concentration of 1 mmol/L. A platinum electrode (a PTE platinum electrode, BAS Inc.) was used as a work electrode, a platinum electrode (a VC-3 Pt counter electrode (5 cm), BAS Inc.) was used as an auxiliary electrode, and an Ag/Ag$^+$electrode (an RE5 non-aqueous solvent reference electrode, BAS Inc.) was used as a reference electrode. The measurement was carried out at room temperature. The scan speed at these CV measurements was set at 0.1 V/s.

The reduction characteristics of PCBNABPA were examined by 100 measurement cycles where the potential of the working electrode with respect to the reference electrode was scanned from −1.24 V to −2.35 V and then scanned from −2.35 V to −1.24 V in each of the cycles. Similarly, the oxidation characteristics were examined by 100 measurement cycles where the potential was scanned from 0.04 V to 0.58 V and then scanned from 0.58 V to 0.04 V in each of the cycles.

Figure 23A:
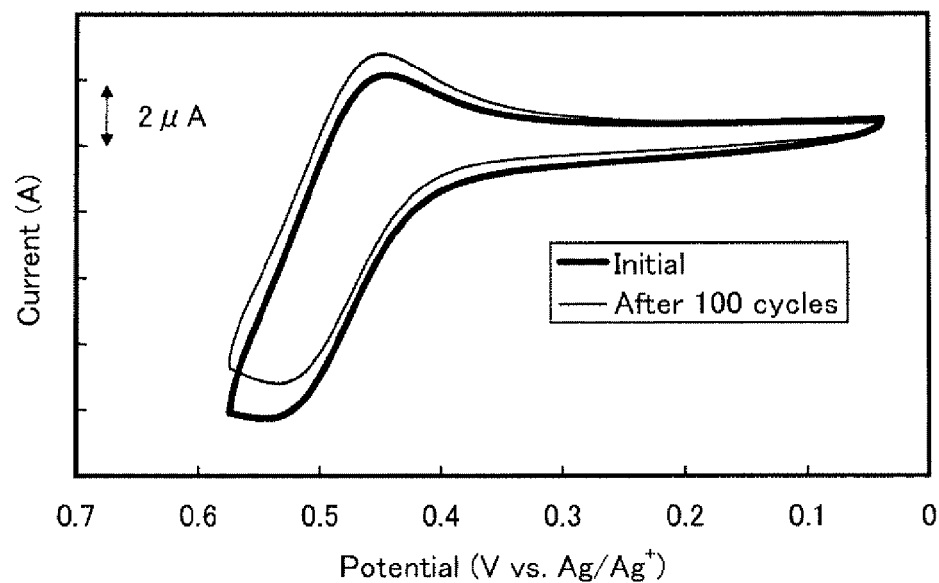
FIGS. 23A and 23B are diagrams showing a CV chart of a DMF solution of 4-[4-(1-naphthyl)phenyl]-4'-(10-phenyl-9-anthryl)-4''-(9-phenyl-9H-carbazol-3-yl)triphenylamine (abbreviated to PCBNBAPA)
Figure 23B:
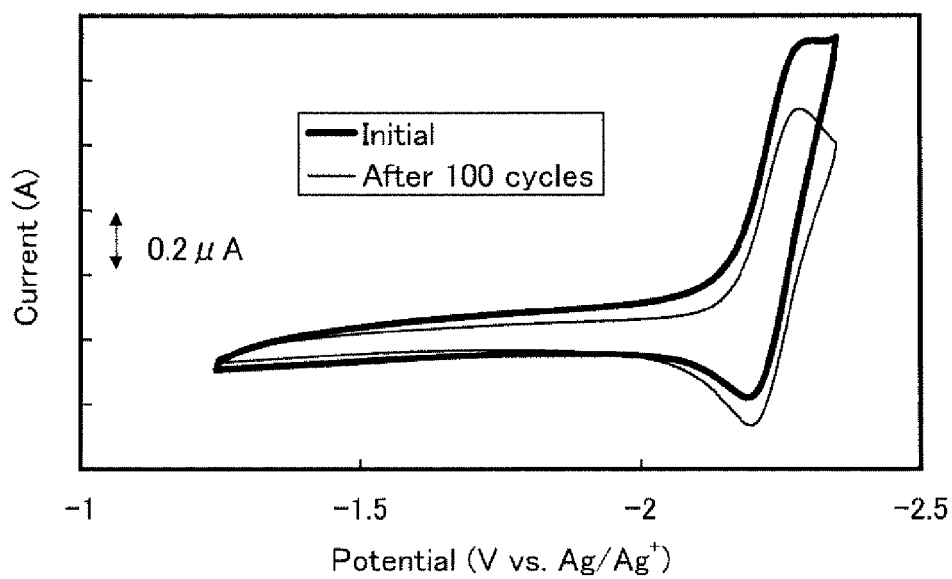

FIG. 23A shows CV measurement results on the oxidation characteristic of PCBNBAPA and FIG. 23B shows CV measurement results on the reduction characteristic of PCBNBAPA. In FIGS. 23A and 23B, the horizontal axis indicates a potential (V) of the working electrode with respect to the reference electrode, and the vertical axis indicates a current value (μA) flowing between the working electrode and the auxiliary electrode.

It can be understood from FIG. 23A that current corresponding to the oxidation is observed around 0.50 V (vs. Ag/Ag+) and from FIG. 23B that current corresponding to the reduction is observed around −2.24 V (vs. Ag/Ag+).

Although the scan was repeated as many as 100 cycles, PCBNBAPA showed no significant change in the peak position and peak intensity of the CV curves in the oxidation and the reduction. The peak intensity remained 87% of the initial state on the oxidation side and 78% of the initial state on the reduction side. Thus, it is understood that PCBNBAPA is relatively stable even when an oxidation from a neutral state to an oxidized state and a reduction from the oxidized state to the neutral state are repeated and when a reduction from the neutral state to a reduced state and an oxidation reaction from the reduced state to the neutral state are repeated.

The results of measuring the thin film of PCBNBAPA by photoelectron spectrometry (AC-2, product of Riken Keiki Co., Ltd.) under air indicated that the HOMO level of PCBNAPA is −5.43 eV. The absorption edge was obtained from Tauc plot, with an assumption of direct transition, using data on the absorption spectrum in FIG. 21, and the energy gap thereof was estimated to be 2.84 eV assuming that the absorption edge corresponds to the optical energy gap. The LUMO level was found to be −2.59 eV by calculation from the value of the energy gap and the HOMO level. As thus described, it was found that PCBNBAPA has a large energy gap of 2.84 eV.

EXAMPLE 3

Figure 9A:
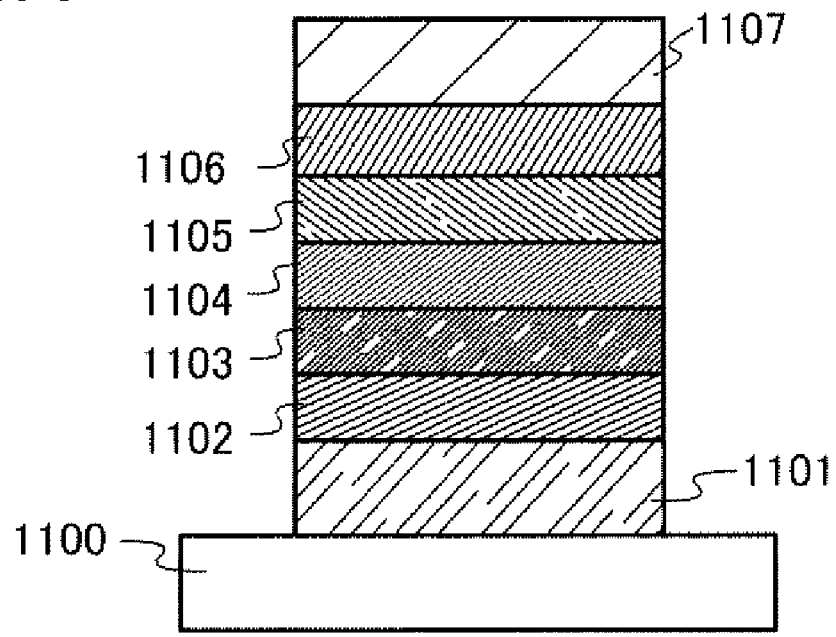
FIGS. 9A and 9B are diagrams explaining a light-emitting element according to an embodiment of the present invention.
Figure 9B:
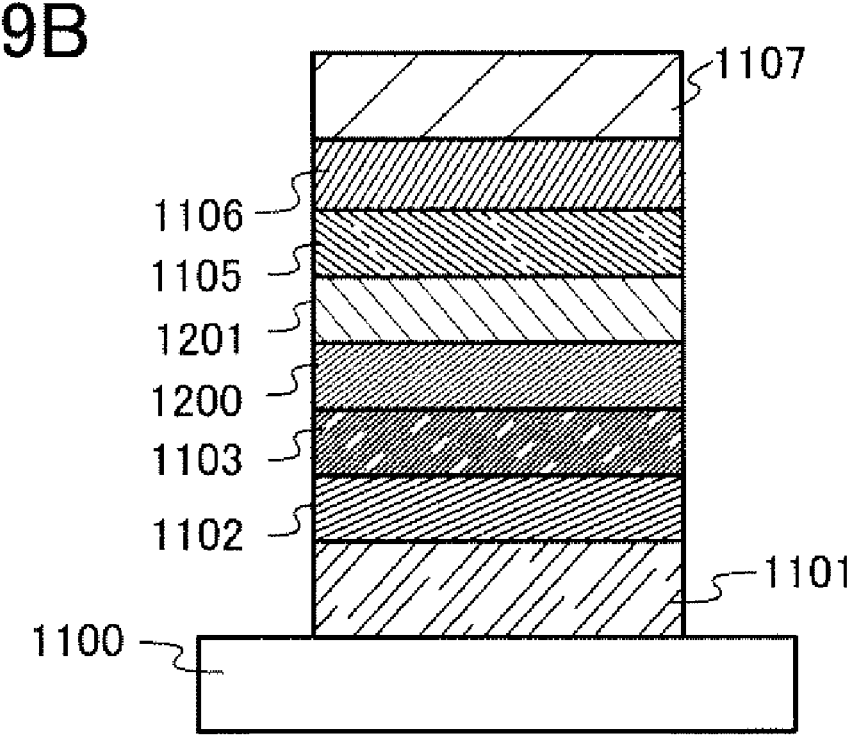

In the present example, an example of a light-emitting element of an embodiment of the present invention is described using FIGS. 9A and 9B. A chemical formulae of materials used in this example are shown below.

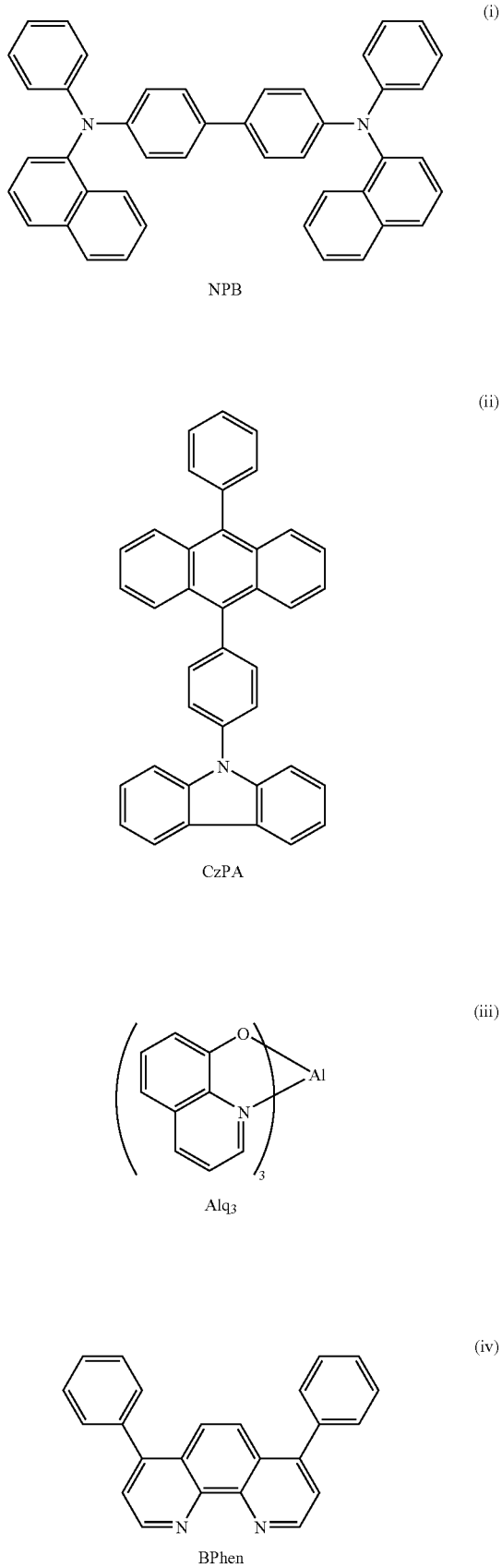

-continued (v)

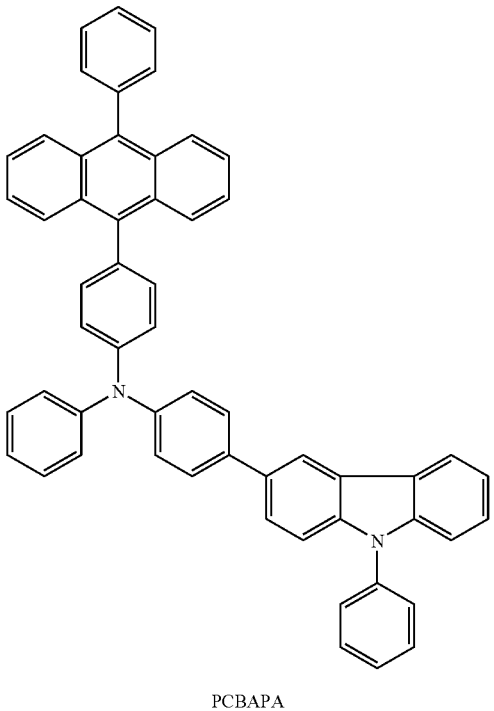

PCBAPA (Light-Emitting Element 1)

The structure of the light-emitting element 1 is explained with reference to FIG. 9A. First, indium tin oxide including silicon oxide was deposited over a glass substrate 1100 by a sputtering method to form a first electrode 1101. The thickness and the area of the first electrode 1101 were set to be 110 nm and 2 mm×2 mm, respectively.

Next, the glass substrate 1100 was fixed to a substrate holder provided in a vacuum evaporation apparatus in such a way that a surface of the glass substrate 1100, over which the first electrode 1101 was formed, faced downward, and then the pressure was reduced to about $10^{-4}$ Pa. Then, 4,4'-bis[N-(1-naphthyl)-N-phenylamino]biphenyl (abbreviated to NPB) and molybdenum(VI) oxide were co-evaporated over the first electrode 1101, whereby a layer 1102 containing a composite material of an organic compound and an inorganic compound was formed. The film thickness of the layer 1102 was set to be 50 nm, and the weight ratio between NPB and molybdenum oxide (=NPB:molybdenum oxide) was adjusted to be 4:1. Note that the co-evaporation method is an evaporation method in which evaporation of a plurality of materials is performed from a plurality of evaporation sources at the same time in one treatment chamber.

Next, NPB was deposited to a thickness of 10 nm over the layer 1102 containing the composite material by the evaporation method utilizing resistive heating, whereby a hole-transporting layer 1103 was formed.

Further, by co-evaporation of 9-[4-(10-phenyl-9-anthryl)phenyl]-9H-carbazole (abbreviated to CzPA) and PCB-NAPA, a light-emitting layer 1104 was formed over the hole-transporting layer 1103 to a thickness of 30 nm. The weight ratio of CzPA and PCBNAPA was adjusted so as to be 1:0.10 (=CzPA:PCBNAPA).

Then, tris(8-quinolinolato)aluminum(III) (abbreviated to Alq) was deposited over the light-emitting layer 1104 to a thickness of 10 nm, and bathophenanthroline (abbreviated to BPhen) was deposited over the Alq layer to a thickness of 20 nm by the evaporation method utilizing resistive heating to form an electron-transporting layer 1105 comprising Alq and BPhen.

Furthermore, lithium fluoride was deposited over the electron-transporting layer 1105 to a thickness of 1 nm, whereby an electron injection layer 1106 was formed.

Lastly, aluminum was deposited to a thickness of 200 nm over the electron injection layer 1106 by the evaporation method utilizing resistive heating to form a second electrode 1107. Accordingly, the light-emitting element 1 was fabricated.

(Comparative Light-emitting Element 1)

Next, a comparative light-emitting element 1 was prepared for comparison with the light-emitting element 1. The structure of the comparative light-emitting element 1 is explained with reference to FIG. 9A. The comparative light-emitting element 1 was prepared using 4-(10-phenyl-9-anthryl)-4'-(9-phenyl-9H-carbazolyl-3-yl)triphenylamine (abbreviated to PCBAPA) instead of PCBNAPA, which is an embodiment of the present invention, to form the light-emitting layer 1104 The weight ratio of CzPA and PCBAPA was adjusted so as to be 1:0.10 (=CzPA:PCBAPA). The structure of the comparative light-emitting element 1 is the same as that of the light-emitting element 1 with the exception of the light-emitting layer 1104.

Figure 24:
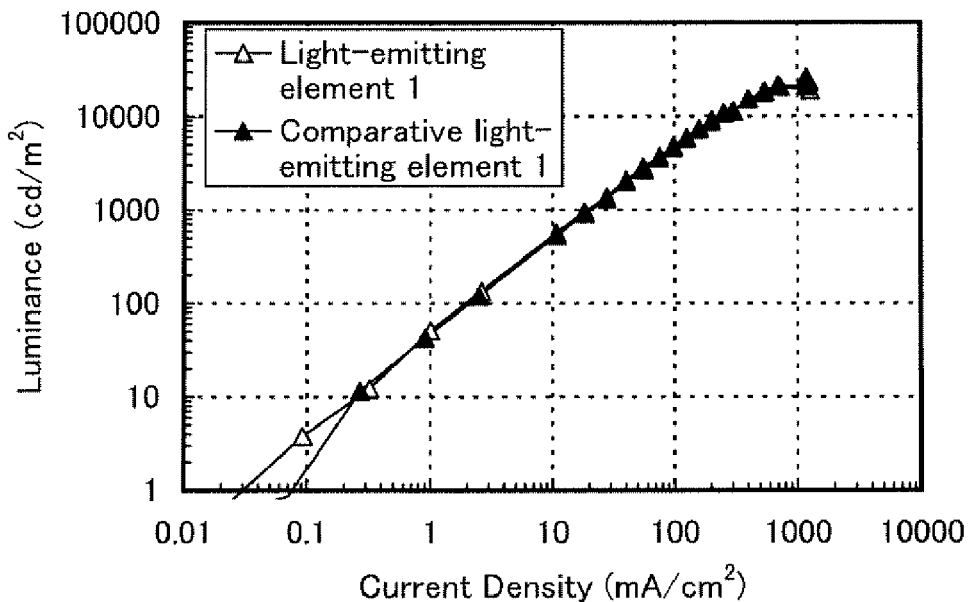
FIG. 24 is a diagram showing current density-luminance characteristics of the light-emitting elements manufactured in Example 3.
Figure 25:
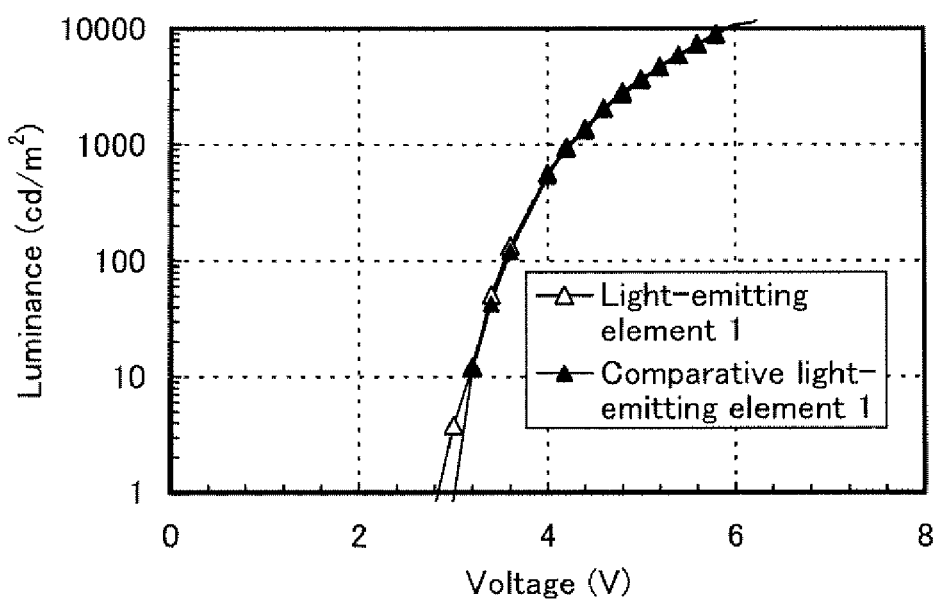
FIG. 25 is a diagram showing voltage-luminance characteristics of the light-emitting elements manufactured in Example 3.
Figure 26:
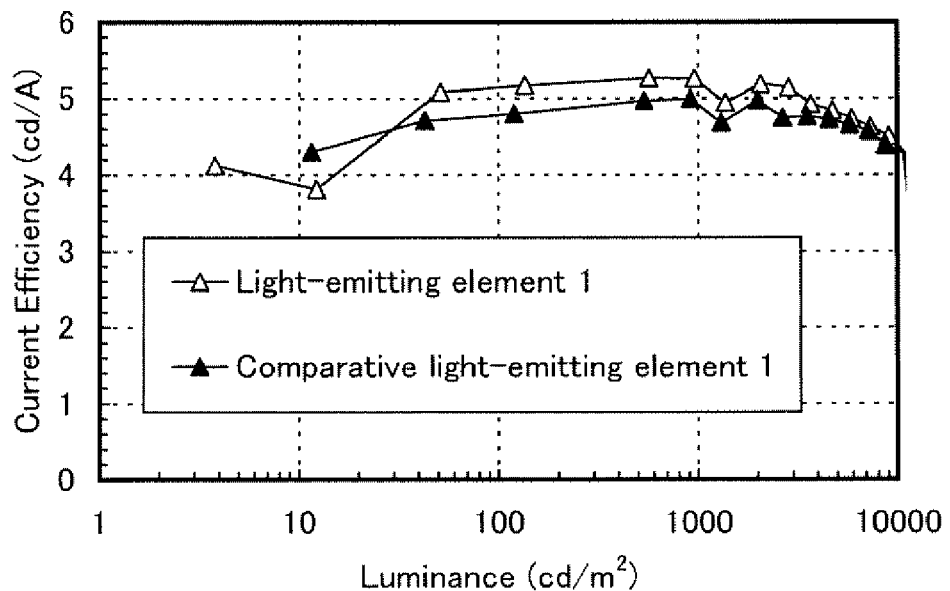
FIG. 26 is a diagram showing luminance-current efficiency characteristics of the light-emitting elements manufactured in Example 3.
Figure 27:
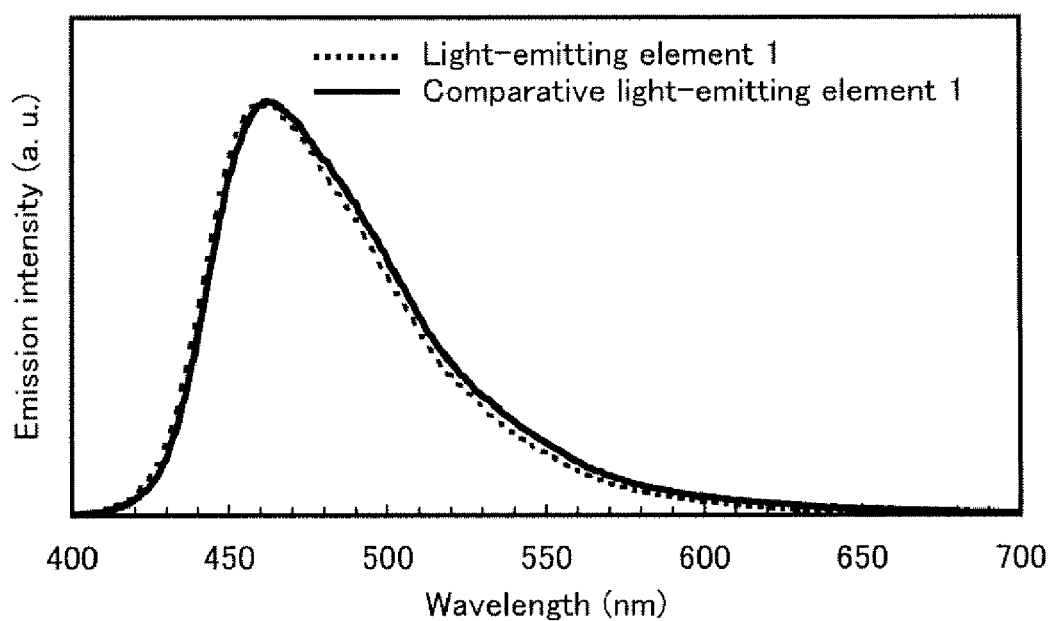
FIG. 27 is a diagram showing emission spectra of the light-emitting elements manufactured in Example 3.

FIG. 24 shows current density-luminance characteristics, FIG. 25 shows voltage-luminance characteristic, FIG. 26 shows luminance-current efficiency characteristics, and FIG. 27 shows the emission spectra measured at a current of 1 mA of the light-emitting element 1 and the comparative light-emitting element 1. From FIG. 27 shows that the light emission of the light-emitting element 1 originates from PCB-NAPA, while the light emission of the comparative light-emitting element 1 originates from PCBAPA. The CIE chromaticity coordinates of the light-emitting element 1 at a luminance of 960 cd/m² are (x, y)=(0.16, 0.20), which is indicative of blue emission with high color purity. FIG. 26 reveals that current efficiency of the light-emitting element 1 at a luminance of 960 cd/m² is 5.3 cd/A, which means that the light-emitting element 1 exhibits high current efficiency. FIG. 25 shows that the driving voltage at 960 cd/m² is 4.2 V, and power efficiency is 3.9 lm/W. From these results, it was found that a voltage required to obtain a certain luminance is low and power consumption is also low in the case of the light-emitting element 1. The CIE chromaticity coordinates of the comparative light-emitting element 1 at a luminance of 910 cd/m² are (x, y)=(0.15, 0.18), indicating that blue emission with high color purity is obtained. FIG. 26 reveals that current efficiency of the comparative light-emitting element 1 at a luminance of 910 cd/m² is 5.0 cd/A, which means that the comparative light-emitting element 1 exhibits relatively high current efficiency. FIG. 25 shows that the driving voltage at 910 cd/m² is 4.2 V, and power efficiency is 3.7 lm/W. From these results, it was found that a voltage required to obtain a certain luminance is low and power consumption is also low in the case of the comparative light-emitting element 1.

Comparison of the light-emitting element 1 with the comparative light-emitting element 1 shows that the light-emitting element 1 exhibits higher current efficiency than the comparative light-emitting element 1. The difference in structure of the emission material in the light-emitting layer between the light-emitting element 1 and the comparative light-emitting element 1 is whether an 1-naphthyl group is provided or not at the terminal of the amine skeleton which is included in the anthracene derivative as an emission material. Whether the 1-naphthyl group is provided or not results in the difference in emission efficiency between the light-emitting element 1 and the comparative light-emitting element 1. Accordingly, these results reveal that the 1-naphthyl group at the terminal of the amine skeleton of the anthracene derivative, which is an embodiment of the present invention, provides an effect to realize high emission efficiency. Further, it is found that the use of the anthracene derivative, which is an embodiment of the present invention, in a light-emitting element enables the production of a light-emitting element which can be driven at a low voltage. Moreover, it was confirmed that a light-emitting element which has high efficiency and low power consumption and is able to be driven at a low voltage can be provided.

Figure 28:
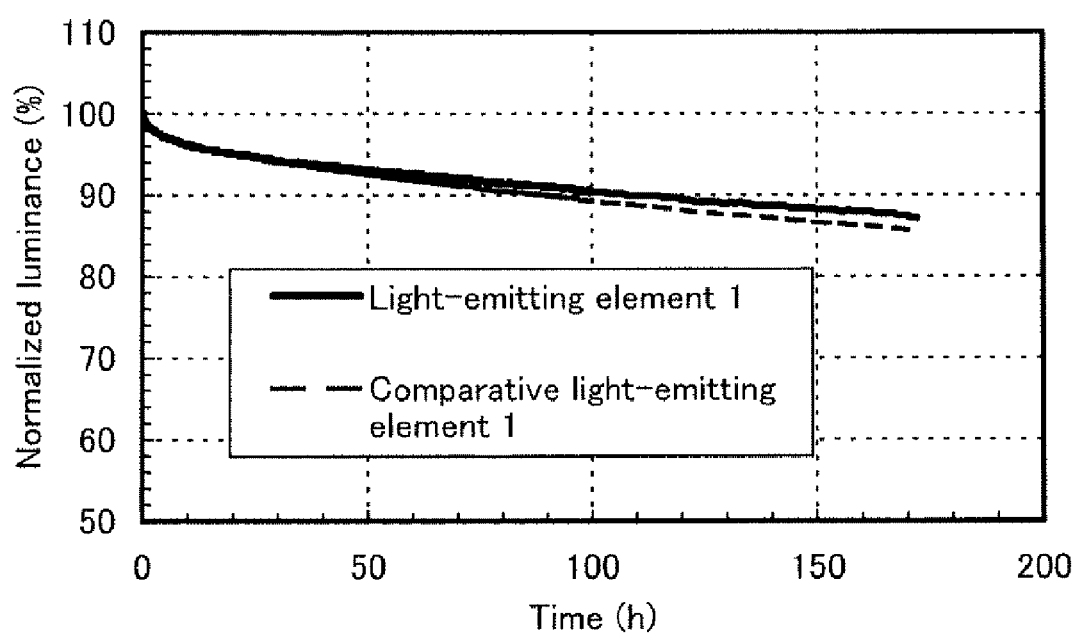
FIG. 28 is a diagram showing the results of the driving tests of the light-emitting elements manufactured in Example 3.

Next, reliability test of the light-emitting element 1 and the comparative light-emitting element 1 was carried out. Results of the reliability test are shown in FIG. 28. In FIG. 28, the vertical axis represents normalized luminance (%) on the assumption that an initial luminance is 100%, and the horizontal axis represents driving time (h) of the light-emitting elements. The reliability test was carried out by driving the light-emitting element 1 and the comparative light-emitting element 1 of this example at a constant current density under the conditions that an initial luminance is set at 1000 cd/m$^2$. FIG. 28 shows that the light-emitting element 1 keeps 88% of the initial luminance after the driving for approximately 150 hours. On the other hand, the comparative light-emitting element 1 keeps 86% of the initial luminance after the driving for approximately 150 hours. Therefore, it was confirmed that although both of the light-emitting element 1 and the comparative light-emitting element 1 exhibit high reliability, the light-emitting element 1 shows higher reliability than the comparative light-emitting element 1. Thus, it was found that the use of the anthracene derivative, which is an embodiment of the present invention, allows the production of a light-emitting element with a long lifetime. Furthermore, the results of the reliability test show that the 1-naphthyl group at the amine skeleton of the anthracene derivative, which is an embodiment of the present invention, has an effect to realize a light-emitting element with a long lifetime.

Since 4-(10-phenyl-9-anthryl)-4'-(9-phenyl-9H-carbazol-3-yl)triphenylamine (abbreviated to PCBAPA) which was used in the present example and is represented by the structural formula (v) is a novel material, the synthetic method thereof is explained.

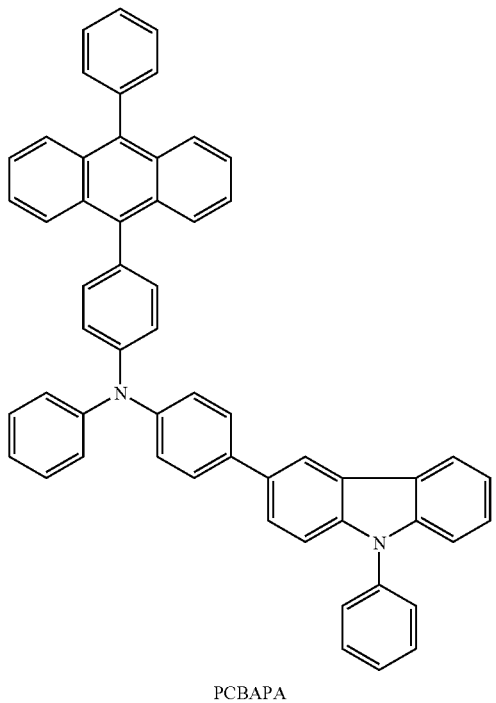

PCBAPA (v)

[Step 1: Synthesis of 3-bromo-9-phenyl-9H-carbazole]

In a 1000 mL Erlenmeyer flask, 24 g (100 mmol) of 9-phenyl-9H-carbazole, 18 g (100 mmol) of N-bromosuccinimide, 450 mL of toluene, and 200 mL of ethyl acetate were added, and the mixture was stirred at room temperature for 45 hours. After the reaction, the resulting mixture was washed with water, and the organic layer is dried with magnesium sulfate. The mixture was filtered, and the resulting filtrate was concentrated to give 32 g of the target substance 3-bromo-9-phenyl-9H-carbazole in 99% yield. The synthetic scheme of 3-bromo-9-phenyl-9H-carbazole is shown in the scheme (C-1).

(C-1)

[Step 2: Synthesis of 9-phenyl-9H-carbazole-3-boronic acid]

Into a 500 mL three-neck flask was put 10 g (31 mmol) of 3-bromo-9-phenyl-9H-carbazole, and the air in the flask was replaced with nitrogen. 150 mL of tetrahydrofuran (THF) was added into the flask to dissolve 3-bromo-9-phenyl-9H-carbazole. This solution was cooled to −80° C. Into this solution was added dropwise 20 mL (32 mmol) of n-butyllithium (a 1.58 mol/L hexane solution) with the use of a syringe. After dropping, the solution was stirred at the same temperature for 1 hour. After the stirring, 3.8 mL (34 mmol) of trimethyl borate was added to the solution, and the solution was stirred for about 15 hours while the temperature of the solution was being brought back to room temperature. After that, ca. 150 mL (1.0 mol/L) of diluted hydrochloric acid was added to the solution, and then the solution was stirred for 1 hour. After stirring, the organic layer was separated from the aqueous layer, the aqueous layer was extracted with ethyl acetate, and the extract and the organic layer were combined and washed with a saturated aqueous solution of sodium hydrogen carbonate. The organic layer was dried with magnesium sulfate, and subjected to gravity filtration. The obtained filtrate was concentrated to give an oily light brown substance. The obtained oily substance was dried under reduced pressure to give 7.5 g of a light brown solid, which was the object of the synthesis, in a yield of 86%. The synthetic scheme of 9-phenyl-9H-carbazole-3-boronic acid is shown in the scheme (C-2).

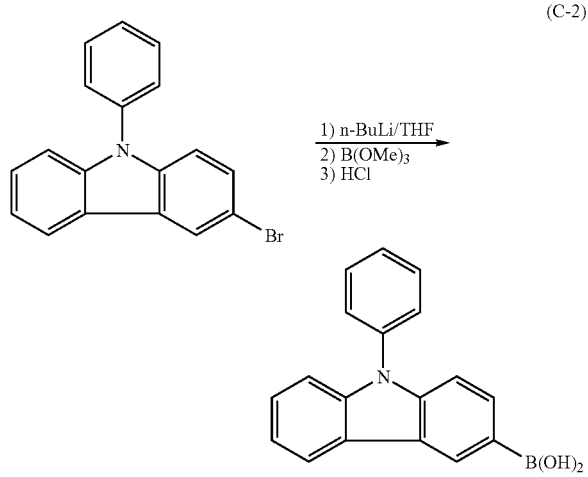

[Step 3: Synthesis of 4-bromodiphenylamine]

Into a 1 L of Erlenmeyer flask was put 51 g (0.3 mol) of diphenylamine which was then dissolved in 700 mL of ethyl acetate. To the solution was added 54 g (0.3 mol) of N-bromosuccinimide (abbreviated to NBS), and stirring was conducted for ca. 30 hours. After the reaction, the mixture was washed with water, and the organic layer was dried with magnesium sulfate. The mixture was filtered, and the filtrate was concentrated to give 70 g of a brown oily substance which is a target substance in 94% yield. The synthetic scheme of 4-bromodiphenylamine is shown in the scheme (C-3).

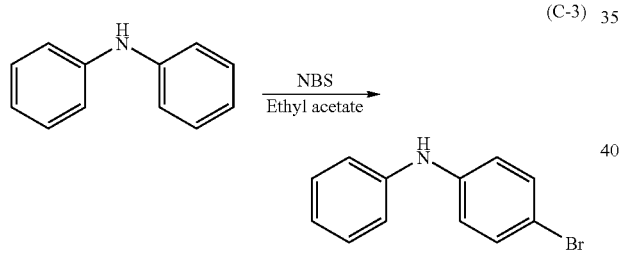

[Step 4: Synthesis of 4-(9-phenyl-9H-carbazol-3-yl)diphenylamine (Abbreviated to PCBA)

In a 500-mL three-neck flask, 6.5 g (26 mmol) of 4-bromodiphenylamine, 7.5 g (26 mmol) of 9-phenyl-9H-carbazol-3-boronic acid, and 400 mg (1.3 mmol) of tri(o-tolyl)phosphine were added, and the atmosphere in the flask was substituted by nitrogen. Then, 100 mL of toluene, 50 mL of ethanol, and 14 mL of aqueous solution of potassium carbonate (0.2 mol/L) were added to this mixture. The mixture was degassed while stirring under reduced pressure, which is followed by the addition of 67 mg (0.3 mmol) of palladium(II) acetate. This mixture was refluxed at 100° C. for 10 hours. After the reflux, the organic layer was separated from the aqueous layer, the aqueous layer was extracted with toluene, and the extract and the organic layer were combined and washed with brine. The organic layer was dried with magnesium sulfate, subjected to gravity filtration. The resulting filtrate was concentrated to give pale brown oily substance. The oily substance was purified by silica gel column chromatography (developing solvent: hexane:toluene=4:6), and a white solid obtained after the purification was recrystallized with a mixed solvent of dichloromethane and hexane to give a white solid which was a target substance. The yield was 4.9 g and 45%. The synthetic scheme of PCBA is shown in the scheme (C-4).

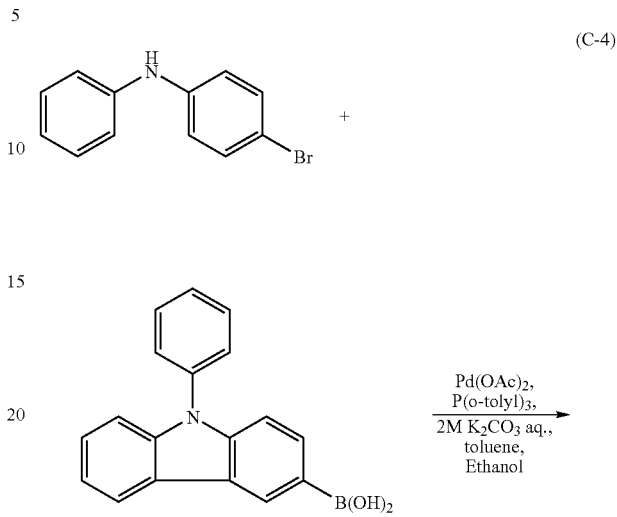

[Step 5: Synthesis of 4-(10-phenyl-9-anthryl)-4'-(9-phenyl-9H-carbazol-3-yl)triphenylamine (Abbreviated to PCBAPA)]

To a 300 mL three-neck flask were added 4.8 g (12 mmol) of 9-(4-bromophenyl)-10-phenylanthracene, 4.8 g (12 mmol) of 4-(9-phenyl-9H-carbazol-3-yl)diphenylamine (abbreviated to PCBA), and 5.2 g (52 mmol) of sodium tert-butoxide. The air in the flask was replaced with nitrogen. To the mixture were added 60 mL of toluene and 0.30 mL of tri(tert-butyl)phosphine (a 10 wt % hexane solution). Under reduced pressure, this mixture was degassed while being stirred. After the degassing, 136 mg (0.24 mmol) of bis(dibenzylideneacetone)palladium(0) were added. Then, the mixture was stirred at 100° C. for 3 hours. After the stirring, ca. 50 mL of toluene was added to this mixture, and the mixture was subjected to suction filtration through Celite (produced by Wako Pure Chemical Industries, Ltd., Catalog No. 531-16855), alumina, and Florisil (produced by Wako Pure Chemical Industries, Ltd., Catalog No. 540-00135). The obtained filtrate was concentrated to give a yellow solid. The solid was recrystallized with a mixed solvent of toluene and hexane to give 6.6 g of a light yellow solid of PCBAPA which was a target substance in a yield of 75%. The synthetic scheme of PCBAPA is shown in the scheme (C-5).

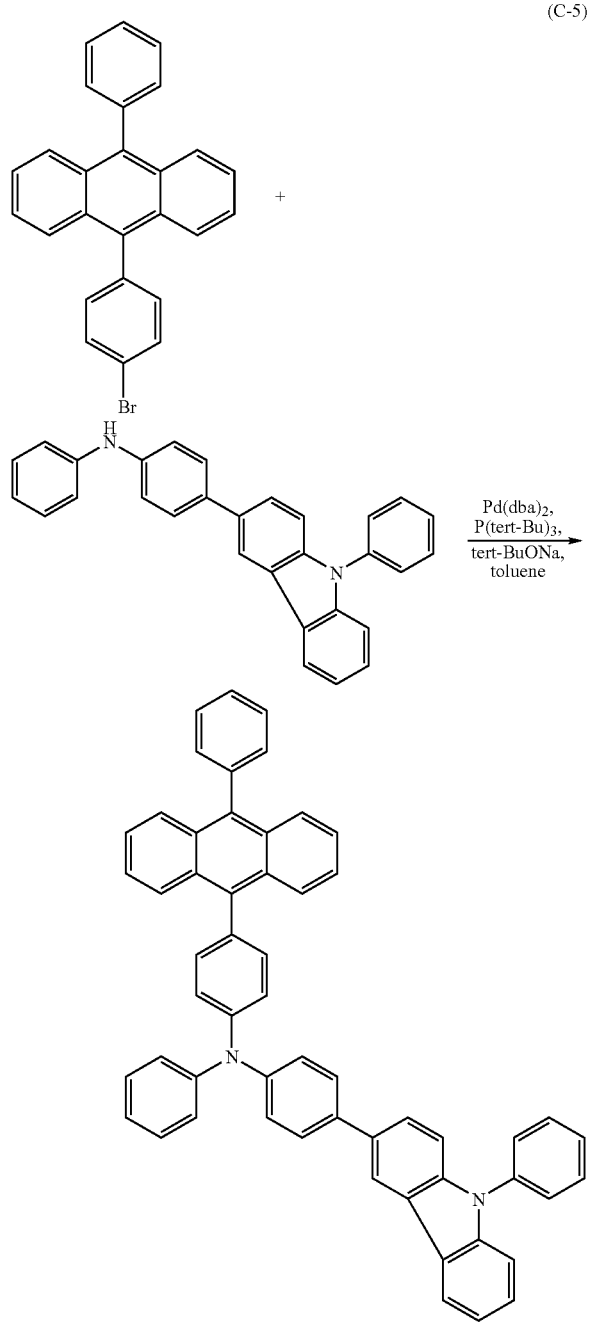

(C-5)

Then, 3.0 g of the obtained pale yellow powder was purified by train sublimation. The conditions for sublimation purification were as follows: the pressure was 8.7 Pa, the argon gas flow rate was 3.0 mL/min, and the heating temperature of PCBACPA was 350° C. After the sublimation purification, 2.7 g of a light yellow solid PCBAPA was recovered in a yield of 90%.

Figure 29A:
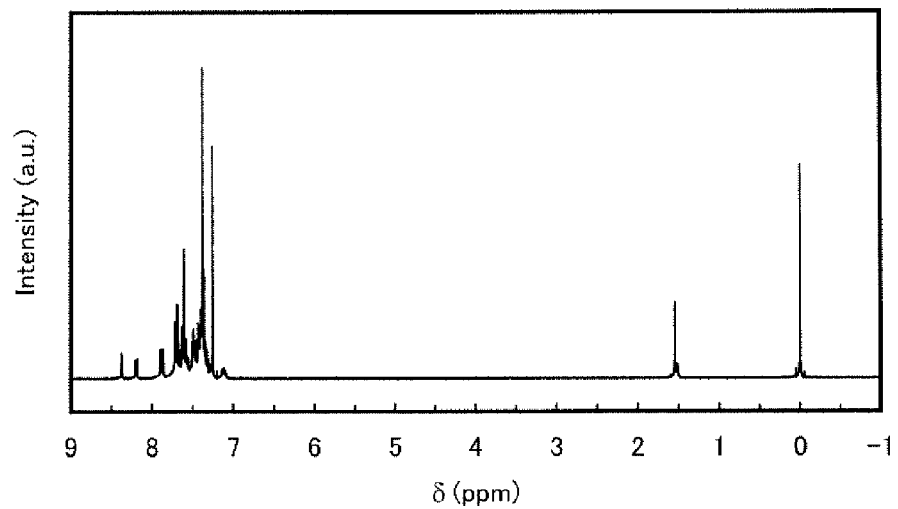
FIGS. 29A and 29B are diagrams showing $^1$H NMR charts of 4-(10-phenyl-9-anthryl)-4'-(9-phenyl-9H-carbazol-3-yl)triphenylamine (abbreviated to PCBAPA)
Figure 29B:
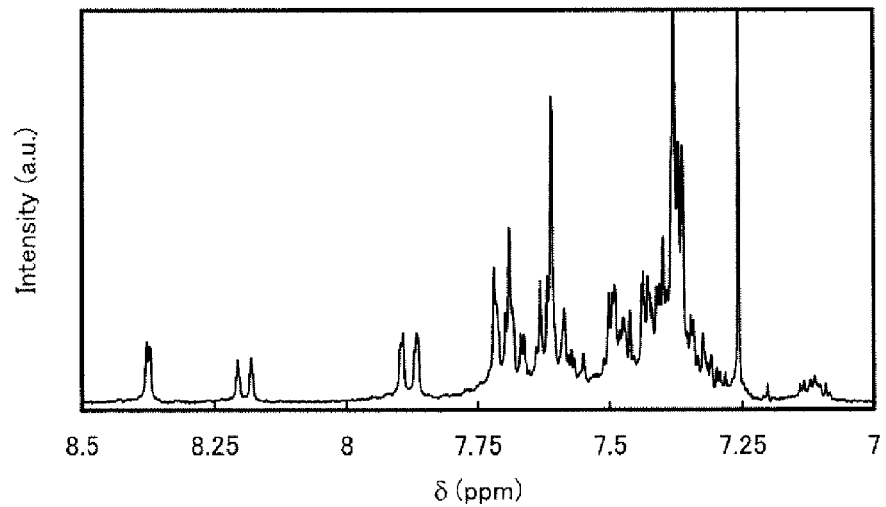

The obtained solid was analyzed by $^1$H NMR. FIGS. 29A and 29B show $^1$H NMR charts. Note that FIG. 29B is a chart in which the range of 7.0 ppm to 8.5 ppm in FIG. 29A is enlarged. From the measurement results, it can be confirmed that the anthracene derivative PCBAPA represented by the above structural formula (v) was obtained. The measurement data are described below.

$^1$H NMR 300 MHz): δ=7.09-7.14 (m, 1H), 7.28-7.72 (m, 33H), 7.88 (d, J=8.4 Hz, 2H), 8.19 (d, J=7.2 Hz, 1H), 8.37 (d, J=1.5 Hz, 1H).

EXAMPLE 4

An example of a light-emitting element of an embodiment of the present invention will be described with reference to FIG. 9B. Materials used in the present example are the same as those used in Example 3.

(Light-emitting Element 2)

First, indium tin oxide including silicon oxide was deposited over a glass substrate 1100 by a sputtering method to form a first electrode 1101. The thickness and the area of the first electrode 1101 were set to be 110 nm and 2 mm×2 mm, respectively.

Next, the glass substrate 1100 was fixed to a substrate holder provided in a vacuum evaporation apparatus in such a way that a surface of the glass substrate 1100, over which the first electrode 1101 was formed, faced downward, and then the pressure was reduced to about $10^{-4}$ Pa. Then, NPB and molybdenum(VI) oxide were co-evaporated over the first electrode 1101, whereby a layer 1102 containing a composite material of an organic compound and an inorganic compound was formed. The film thickness of the layer 1102 was set to be 50 nm, and the weight ratio between NPB and molybdenum oxide (=NPB:molybdenum oxide) was adjusted to be 4:1.

Next, NPB was deposited to a thickness of 10 nm over the layer 1102 containing the composite material by the evaporation method utilizing resistive heating, whereby a hole-transporting layer 1103 was formed.

Next, the anthracene derivative PCBNAPA which is an embodiment of the present invention was evaporated over the hole-transporting layer 1103 to a thickness of 20 nm to form a first light-emitting layer 1200.

Further, by co-evaporation of CzPA and PCBNAPA, a second light-emitting layer 1201 with a thickness of 30 nm was formed over the first light-emitting layer 1200. Here, the weight ratio of CzPA to PCBNAPA was adjusted to 1:0.05 (=CzPA:PCBNAPA).

Then, Alq was deposited over the second light-emitting layer 1201 to a thickness of 30 nm by the evaporation method utilizing resistive heating to form an electron-transporting layer 1105.

Furthermore, lithium fluoride was deposited over the electron-transporting layer 1105 to a thickness of 1 nm, whereby an electron injection layer 1106 was formed.

Lastly, aluminum was deposited to a thickness of 200 nm over the electron injection layer 1106 by the evaporation method utilizing resistive heating to form a second electrode 1107. Accordingly, the light-emitting element 2 was fabricated.

(Comparative Light-emitting Element 2)

Next, a comparative light-emitting element 2 was prepared. The structure of the comparative light-emitting element 2 is explained with reference to FIG. 9B. The comparative light-emitting element 2 was prepared using PCBAPA represented by the structural formula (v) instead of PCB-NAPA, which is an embodiment of the present invention, to form the first light-emitting layer 1200 and the second light-emitting layer 1201. Here, PCBAPA was used in the first light-emitting layer 1200, and the weight ratio of CzPA and PCBAPA in the second light-emitting layer 1201 was adjusted so as to be 1:0.05 (=CzPA:PCBAPA). The structure of the comparative light-emitting element 2 is the same as that of the light-emitting element 2 with the exception of the first light-emitting layer 1200 and the second light-emitting layer 1201.

Figure 30:
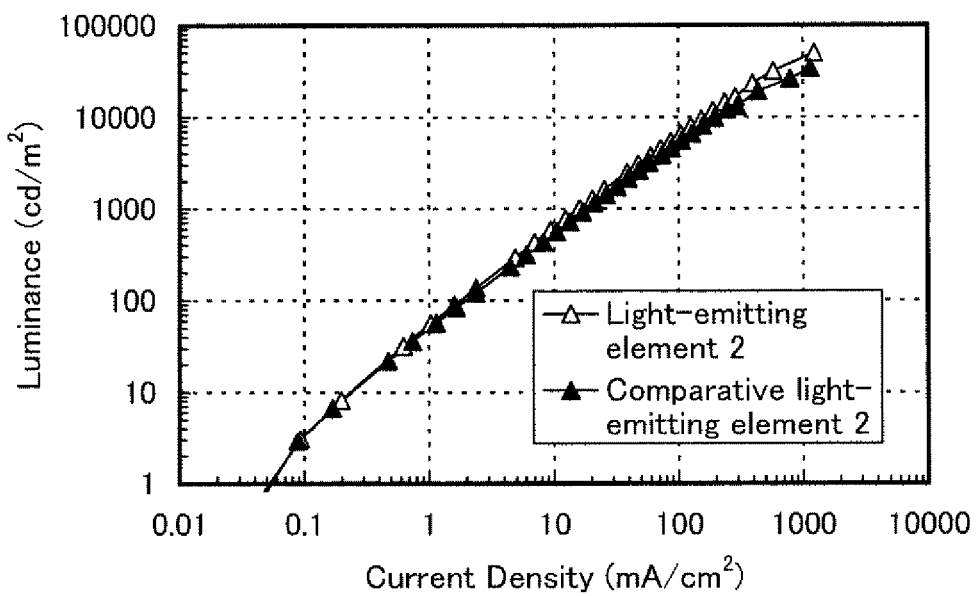
FIG. 30 is a diagram showing current density-luminance characteristics of the light-emitting elements manufactured in Example 4.
Figure 31:
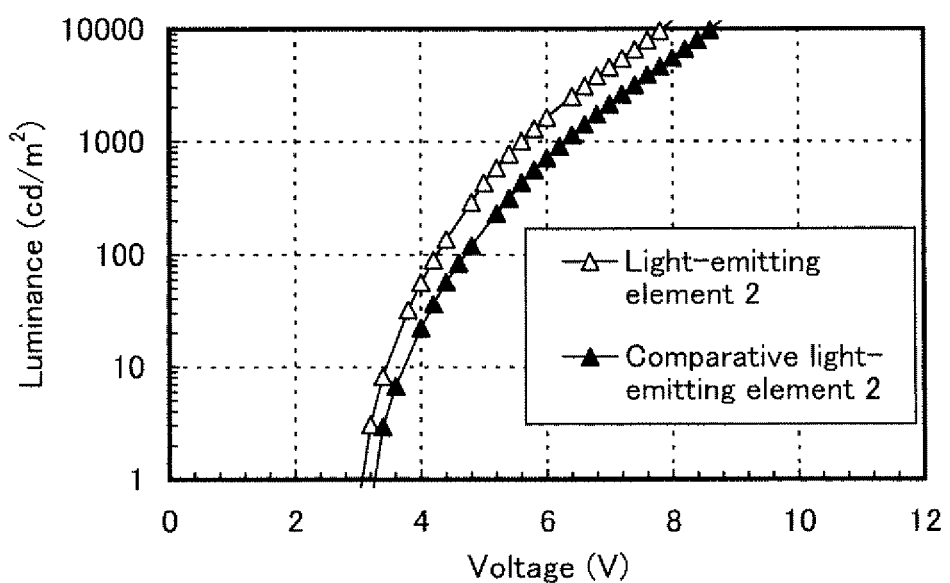
FIG. 31 is a diagram showing voltage-luminance characteristics of the light-emitting elements manufactured in Example 4.
Figure 32:
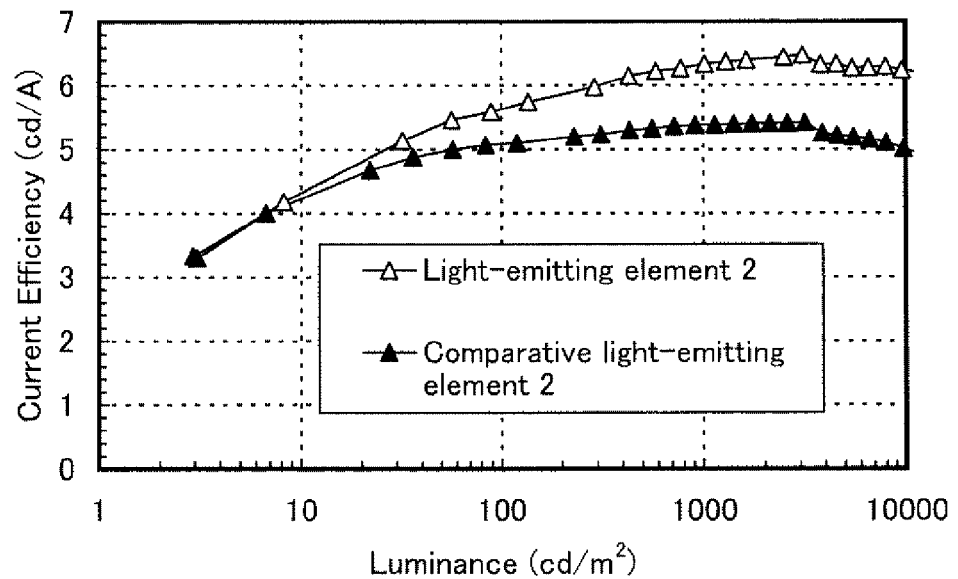
FIG. 32 is a diagram showing luminance-current efficiency characteristics of the light-emitting elements manufactured in Example 4.
Figure 33:
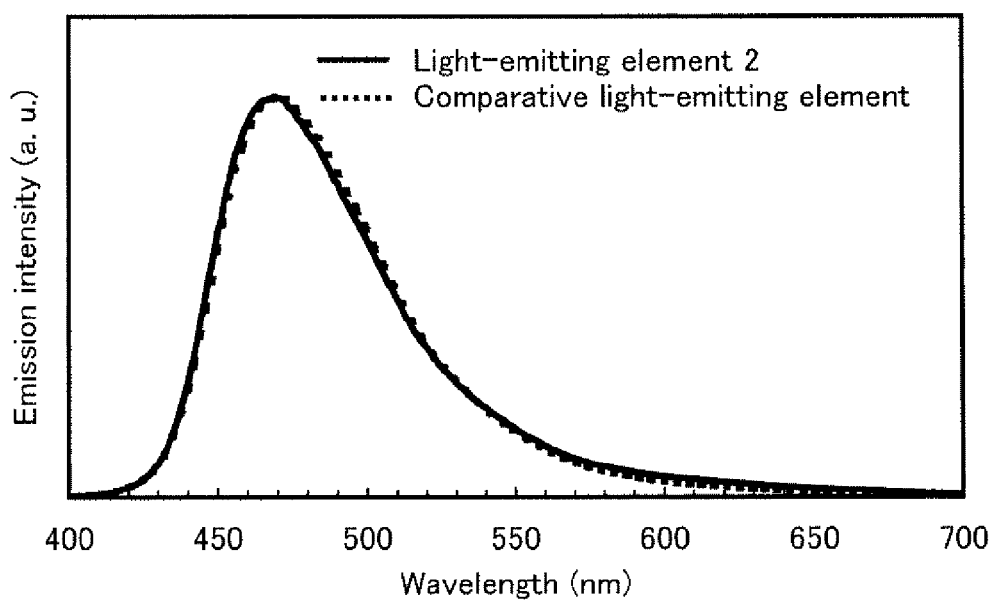
FIG. 33 is a diagram showing emission spectra of the light-emitting elements manufactured in Example 4.

FIG. 30 shows current density-luminance characteristics, FIG. 31 shows voltage-luminance characteristic, FIG. 32 shows luminance-current efficiency characteristics, and FIG. 33 shows the emission spectra measured at a current of 1 mA of the light-emitting element 2 and the comparative light-emitting element 2. From FIG. 33, it was found that the light emission of the light-emitting element 2 results from PCB-NAPA, while the light emission of the comparative light-emitting element 2 is originates from PCBAPA. The CIE chromaticity coordinates of the light-emitting element 2 at a luminance of 1010 cd/m² are (x, y)=(0.16, 0.22), which means that blue emission was obtained. FIG. 32 reveals that current efficiency of the light-emitting element 2 at a luminance of 1010 cd/m² is 6.3 cd/A, which means that the light-emitting element 2 exhibits high current efficiency. FIG. 31 shows that the driving voltage at 1010 cd/m² is 5.6 V, and power efficiency is 3.9 μm/W. From these results, it was found that a voltage required to obtain a certain luminance is low and power consumption is also low in the case of the light-emitting element 2. The CIE chromaticity coordinates of the comparative light-emitting element 2 at a luminance of 910 cd/m² are (x, y)=(0.16, 0.22), which means that t blue emission is obtained. FIG. 32 reveals that current efficiency of the comparative light-emitting element 2 at a luminance of 910 cd/m² is 5.4 cd/A, which means that the comparative light-emitting element 2 exhibits relatively high current efficiency. FIG. 31 shows that the driving voltage at 910 cd/m² is 6.2 V, and power efficiency is 3.7 μm/W. From these results, it was found that a voltage required to obtain a certain luminance is low and power consumption is also low in the ease of the comparative light-emitting element 2.

Comparison of the light-emitting element 2 with the comparative light-emitting element 2 shows that the light-emitting element 2 exhibits higher current efficiency than the comparative light-emitting element 2. The difference in structure of the emission material in the light-emitting layer between the light-emitting element 2 and the comparative light-emitting element 2 is whether or not an 1-naphthyl group is provided at the terminal of the amine skeleton which is included in the anthracene derivative as an emission material. Whether or not the 1-naphthyl group is provided results in the difference in emission efficiency between the light-emitting element 2 and the comparative light-emitting element 2. Thus, it was also demonstrated from Example 4 that the 1-naphthyl group at the amine skeleton of the anthracene derivative which is an embodiment of the present invention provides an effect to realize high emission efficiency. Further, it was found that the use of the anthracene derivative, which is an embodiment of the present invention, in a light-emitting element enables the production of a light-emitting element which can be driven at a low voltage. Moreover, it was confirmed that a light-emitting element which has high efficiency and low power consumption and is able to be operated at a low voltage can be provided.

Figure 34:
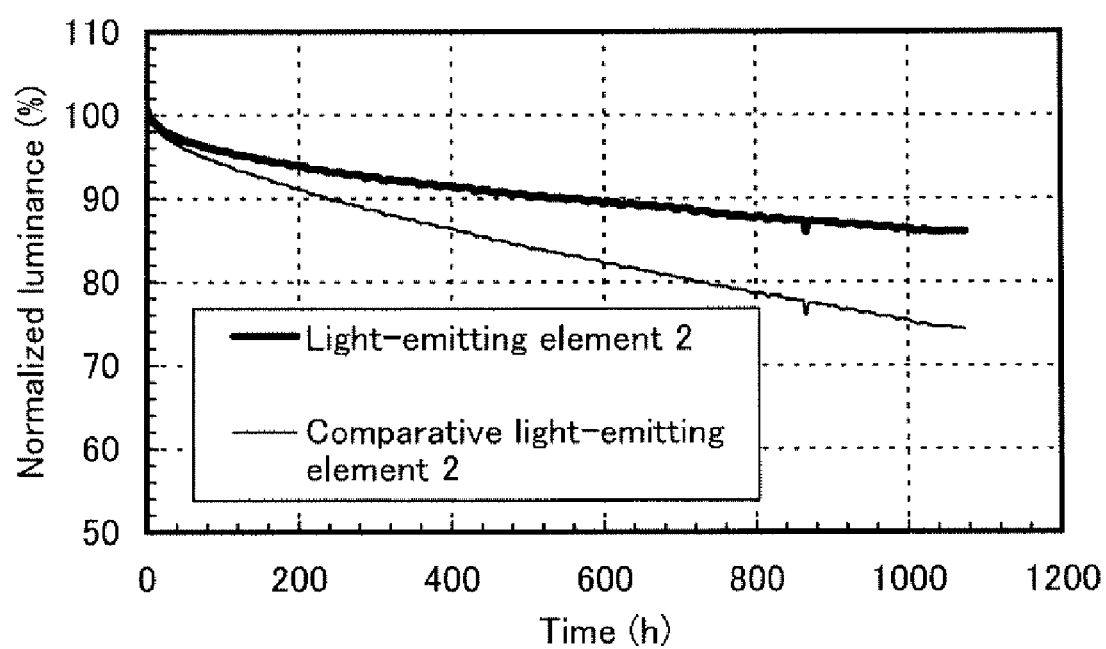
FIG. 34 is a diagram showing the driving results of the light-emitting elements manufactured in Example 4.

Next, reliability test of the light-emitting element 2 and the comparative light-emitting element 2 was carried out. Results of the reliability test are shown in FIG. 34. In FIG. 34, the vertical axis represents normalized luminance (%) on the assumption that an initial luminance is 100%, and the horizontal axis represents driving time (h) of the light-emitting elements. The reliability test was carried out by driving the light-emitting element 2 and the comparative light-emitting element 2 of this example at a constant current density under the conditions that an initial luminance is set at 1000 cd/m².

FIG. 34 shows that the light-emitting element 2 keeps 86% of the initial luminance after the driving for approximately 1000 hours. On the other hand, the comparative light-emitting element 2 keeps 75% of the initial luminance after the driving for approximately 1000 hours. Therefore, it was confirmed that although both of the light-emitting element 2 and the comparative light-emitting element 2 exhibit high reliability, the light-emitting element 2 shows higher reliability than the comparative light-emitting element 2. Thus, it was found that the use of the anthracene derivative, which is an embodiment of the present invention, allows the production of a light-emitting element with a long lifetime. Furthermore, the results of the reliability test show that the 1-naphthyl group at the amine skeleton of the anthracene derivative, which is an embodiment of the present invention, has an effect to realize a light-emitting element with a long lifetime.

This application is based on Japanese Patent Application serial no. 2008-269097 filed with Japan Patent Office on Oct. 17, 2008 and on Japanese Patent Application serial no. 2009-030140 filed with Japan Patent Office on Feb. 12, 2009, the entire contents of which are hereby incorporated by reference.

What is claimed is:
1. A light-emitting device comprising:
a first electrode over a substrate;
a light-emitting unit over the first electrode, and comprising a first light-emitting layer and a second light-emitting layer over the first electrode; and
a second electrode over the light-emitting unit,
wherein the first light-emitting layer consists of an anthracene derivative represented by General Formula (G1)

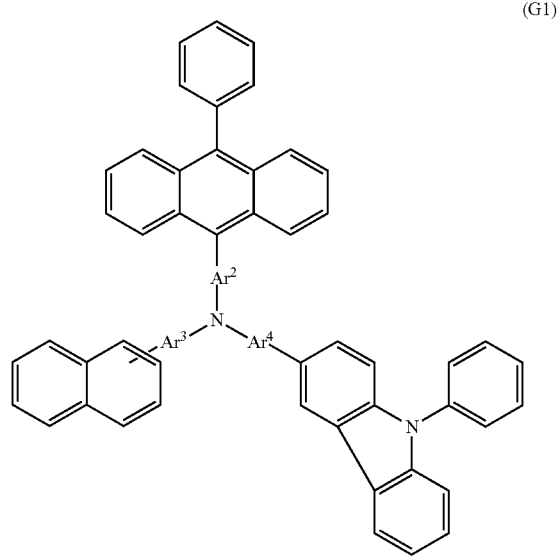

(G1)

wherein $Ar^2$, $Ar^3$, and $Ar^4$ each independently represent a phenylene group or a biphenyl-4,4'-diyl group, and
wherein the second light-emitting layer comprises the anthracene derivative and an organic compound having electron-transporting property.
2. The light-emitting device according to claim 1, wherein $Ar^4$ is a para-phenylene group.
3. The light-emitting device according to claim 1, wherein $Ar^2$ is a para-phenylene group.

4. The light-emitting device according to claim 1, wherein $Ar^3$ is a para-phenylene group.

5. The light-emitting device according to claim 1, wherein the anthracene derivative is represented by Formula (101) or (103)

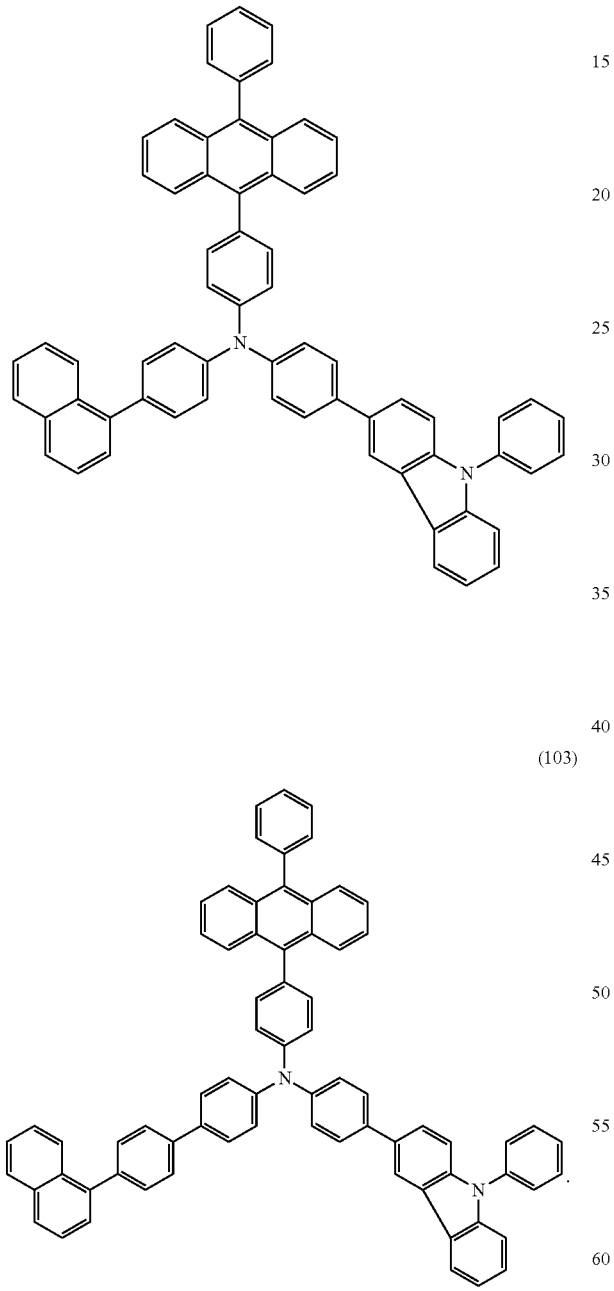

6. The light-emitting device according to claim 1, wherein the first electrode is an anode.

7. The light-emitting device according to claim 1, wherein one or both of the first electrode and the second electrode is a light-transmitting electrode.

8. The light-emitting device according to claim 1, wherein the substrate is a plastic substrate.

9. The light-emitting device according to claim 1, wherein the light-emitting device is a lighting device.

10. A light-emitting device comprising:
a first electrode over a substrate;
a first light-emitting layer over the first electrode;
a second light-emitting layer over the first light-emitting layer; and
a second electrode over the second light-emitting layer,
wherein the first light-emitting layer consists of an anthracene derivative represented by General Formula (G1)

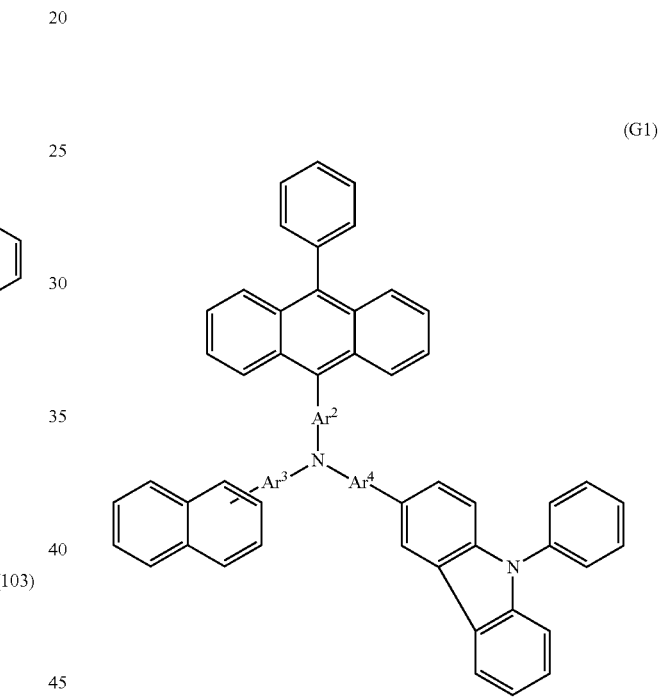

wherein $Ar^2$, $Ar^3$, and $Ar^4$ each independently represent a phenylene group or a biphenyl-4,4'-diyl group, and
wherein the second light-emitting layer comprises the anthracene derivative and an organic compound having electron-transporting property.

11. The light-emitting device according to claim 10, wherein $Ar^4$ is a para-phenylene group.

12. The light-emitting device according to claim 10, wherein $Ar^2$ is a para-phenylene group.

13. The light-emitting device according to claim 10, wherein $Ar^3$ is a para-phenylene group.

14. The light-emitting device according to claim 10, wherein the anthracene derivative is represented by Formula (101) or (103)

(101)

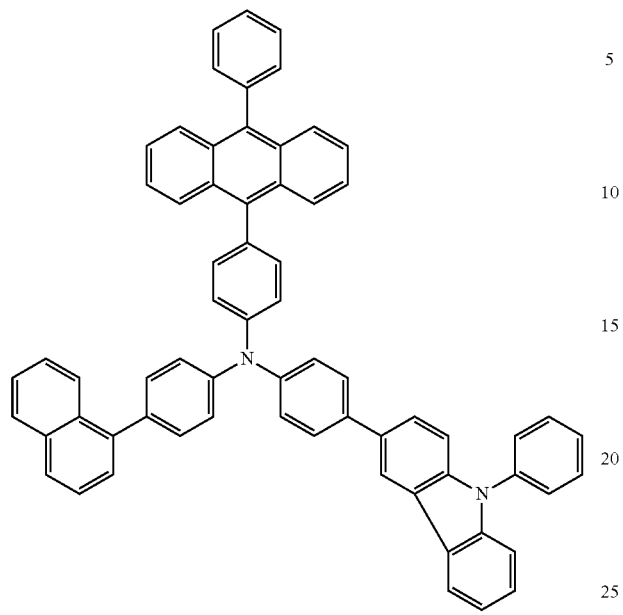

(103)

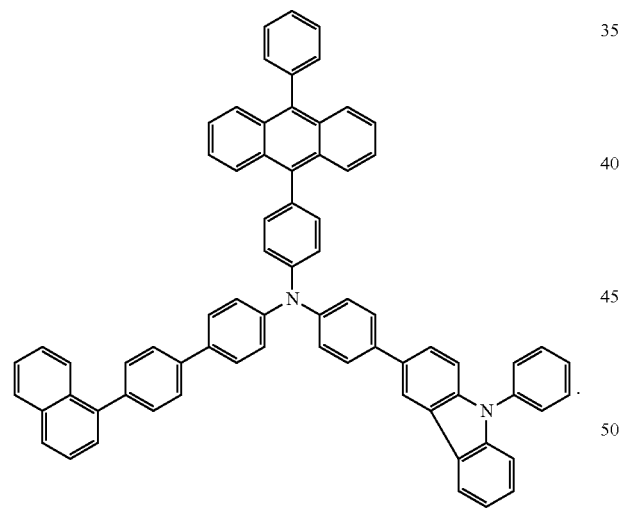

15. The light-emitting device according to claim 10, wherein the first electrode is an anode.

16. The light-emitting device according to claim 10, wherein one or both of the first electrode and the second electrode is a light-transmitting electrode.

17. The light-emitting device according to claim 10, wherein the substrate is a plastic substrate.

18. The light-emitting device according to claim 10, wherein the light-emitting device is a lighting device.

19. A light-emitting device comprising:
a first electrode over a substrate;
a first light-emitting unit over the first electrode;
a charge generation layer over the first light-emitting unit;
a second light-emitting unit over the charge generation layer; and
a second electrode over the second light-emitting unit,
wherein at least one of the first light-emitting unit and the second light-emitting unit comprises a first light-emitting layer and a second light-emitting layer, wherein the first light-emitting layer consists of an anthracene derivative represented by General Formula (G1)

(G1)

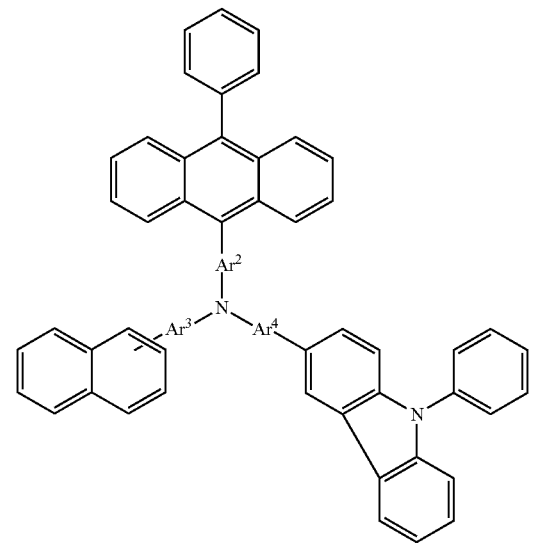

wherein $Ar^2$, $Ar^3$, and $Ar^4$ each independently represent a phenylene group or a biphenyl-4,4'-diyl group, and wherein the second light-emitting layer comprises the anthracene derivative and an organic compound having electron-transporting property.

20. The light-emitting device according to claim 19, wherein the anthracene derivative is represented by Formula (101) or (103)

(101)
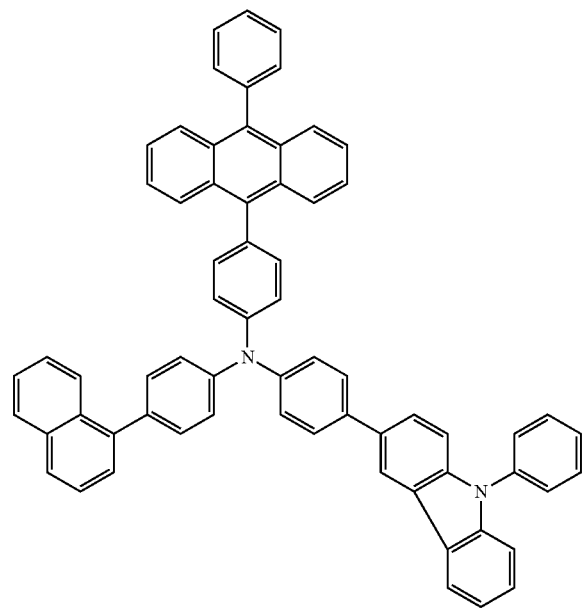
(103)
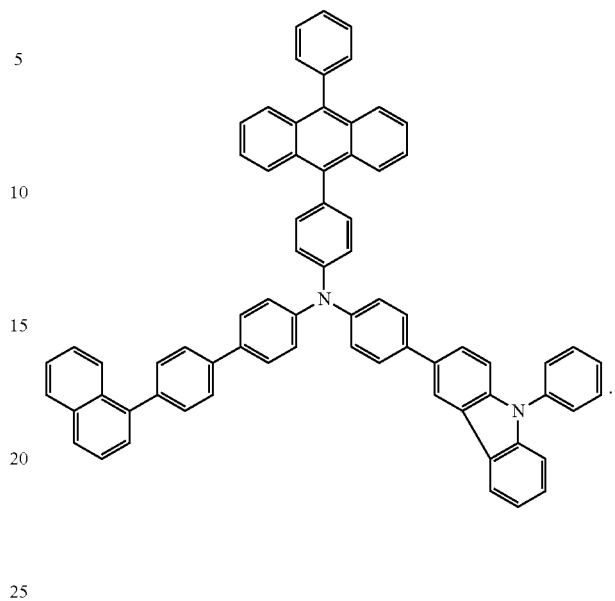
* * * * *

UNITED STATES PATENT AND TRADEMARK OFFICE
CERTIFICATE OF CORRECTION

PATENT NO.         : 7,960,566 B2
APPLICATION NO.    : 12/576016
DATED              : June 14, 2011
INVENTOR(S)        : Kaori Ogita et al.

It is certified that error appears in the above-identified patent and that said Letters Patent is hereby corrected as shown below:

Column 33, line 20, "nitrite" should read "nitrile"

Column 43, line 44, "as tong as" should read "as long as"

Column 47, line 8, "Poly-TAD" should read "Poly-TPD"

Column 50, line 10, "CzAlPA" should read "CzA1PA"

Column 50, line 42, "RANT" should read "BANT"

Column 54, line 42, "in this" should read "In this"

Column 73, a chemical formula in the synthetic scheme of PCBNBAPA shown in scheme (B-3)

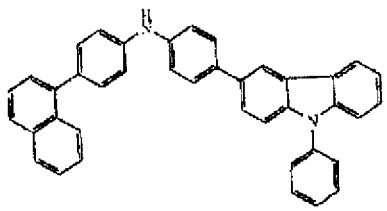

Should read

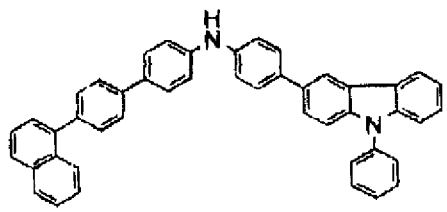

Signed and Sealed this
Tenth Day of January, 2012

David J. Kappos
*Director of the United States Patent and Trademark Office*

CERTIFICATE OF CORRECTION (continued)
U.S. Pat. No. 7,960,566 B2

Column 74, line 20, "TG/DTA 24105A" should read "TG/DTA 2410SA"

Column 85, line 20, "3.9µm/W" should read "3.9lm/W"

Column 85, line 33, "in the ease of" should read "in the case of"